US008435577B2

(12) United States Patent
Andersen et al.

(10) Patent No.: US 8,435,577 B2
(45) Date of Patent: May 7, 2013

(54) ALPHA-AMYLASES

(75) Inventors: Carsten Andersen, Vaerloese (DK); Thomas Agersten Poulsen, Ballerup (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 13/514,727

(22) PCT Filed: Jan. 4, 2011

(86) PCT No.: PCT/EP2011/050073
§ 371 (c)(1),
(2), (4) Date: Jun. 20, 2012

(87) PCT Pub. No.: WO2011/080352
PCT Pub. Date: Jul. 7, 2011

(65) Prior Publication Data
US 2012/0264176 A1     Oct. 18, 2012

Related U.S. Application Data

(60) Provisional application No. 61/304,092, filed on Feb. 12, 2010, provisional application No. 61/292,324, filed on Jan. 5, 2010, provisional application No. 61/292,327, filed on Jan. 5, 2010, provisional application No. 61/333,930, filed on May 12, 2010, provisional application No. 61/354,775, filed on Jun. 15, 2010, provisional application No. 61/354,817, filed on Jun. 15, 2010, provisional application No. 61/355,230, filed on Jun. 16, 2010, provisional application No. 61/362,536, filed on Jul. 8, 2010.

(30) Foreign Application Priority Data

Jan. 4, 2010 (EP) .................................... 10150062
Jan. 4, 2010 (EP) .................................... 10150063

(51) Int. Cl.
*A21D 2/00* (2006.01)
*A21D 2/20* (2006.01)
*C12P 7/06* (2006.01)
*C11D 3/386* (2006.01)

(52) U.S. Cl.
USPC .............. 426/18; 426/27; 435/161; 435/205; 510/226

(58) Field of Classification Search .................... 426/28, 426/13; 435/201, 202; 530/350
See application file for complete search history.

(56) References Cited

FOREIGN PATENT DOCUMENTS

| | | |
|---|---|---|
| EP | 1022334 A2 | 7/2000 |
| WO | 95/26397 A1 | 10/1995 |
| WO | 96/23873 A1 | 8/1996 |
| WO | 97/32961 A2 | 9/1997 |
| WO | 00/60060 A2 | 10/2000 |
| WO | 01/66712 A2 | 9/2001 |
| WO | 02/10355 A2 | 2/2002 |
| WO | 03/083054 A2 | 10/2003 |
| WO | 2006/002643 A2 | 1/2006 |
| WO | 2006/066596 A2 | 6/2006 |
| WO | 2009/134670 A2 | 11/2009 |
| WO | 2010/074999 A1 | 7/2010 |

OTHER PUBLICATIONS

Brzozowski et al., Biochemistry, vol. 39, pp. 9099-9107 (2000).
Conrad et al., European Journal of Biochemistry, vol. 230, No. 2, pp. 481-490 (1995).
Liu et al., Current Microbiology, vol. 60, No. 3, pp. 162-166 (2010).
MacGregor et al., Biochimica et Biophysics Acta, vol. 1546, No. 1, pp. 1-20 (2001).
Machius et al., Journal of Molecular Biology, vol. 246, pp. 545-559 (1995).
Machius et al., Structure, vol. 6, No. 3, pp. 281-293 (1998).
Marcel, UniProt Database, Accession No. Q03657 (1996).
Nielsen et al., Biochimica et Biophysica Acta, vol. 1543, pp. 253-274 (2000).
Nishizawa et al., DNA, vol. 6, No. 3, pp. 255-265 (1987).
Nonaka et al., Journal of Biological Chemistry, vol. 278, No. 27, pp. 24818-24824 (2008).
Priyadharshini et al., Biotechnology Letters, vol. 29, No. 10, pp. 1493-1499 (2007).
Richardson et al., Journal of Biological Chemistry, vol. 277, No. 29, pp. 26501-26507 (2002).
Rodenburg et al., European Journal of Biochemistry, vol. 221, No. 1, pp. 277-284 (1994).
Suvd et al., Journal of Biochemistry, vol. 129, pp. 461-468 (2001).

*Primary Examiner* — Maryam Monshipouri
(74) *Attorney, Agent, or Firm* — Elias Lambiris

(57) ABSTRACT

The present invention relates to alpha-amylases, nucleic acids encoding the alpha-amylases, methods of producing the alpha-amylases, and methods of using the alpha-amylases.

16 Claims, 4 Drawing Sheets

```
                          1                                              50
SEQ ID NO C1    (1)  -------VNGTLMQYFEWYTPNDGQHWKRLQNDAEHLSDIGITAVWIPPA
SEQ ID NO C2    (1)  ---GSVPVNGTMMQYFEWYLPDDGTLWTKVANNAQSLANLGITALWLPPA
SEQ ID NO C3    (1)  -----ANLNCTLMQYFEWYMPNDCQHWRRLQNDSAYLAEHCITAVWIPPA
SEQ ID NO C4    (1)  ----AAPFNGTMMQYFEWYLPDDGTLWTKVANEANNLSSLGITALWLPPA
SEQ ID NO C5    (1)  ---HHNGTNGTMMQYFEWYLPNDGNHWNRLRSDASNLKDKGISAVWIPPA
SEQ ID NO C6    (1)  ---HHNGTNGTMMQYFEWYLPNDGNHWNRLRDDAANLKSKGITAVWIPPA
SEQ ID NO C7    (1)  ---HHNGTNGTMMQYFEWHLPNDGNHWNRLRDDASNLRNRGITAIWIPPA
SEQ ID NO C8    (1)  ---HHNGTNGTMMQYFEWYLPNDGNHWNRLKSDASNLKSKGITAVWIPPA
SEQ ID NO C9    (1)  ---GSVPVNGTMMQYFEWYLPDDGTLWTKVANNAQSLANLGITALWLPPA
SEQ ID NO 10    (1)  ---NTAPINETMMQYFEWDLPNDGTLWTKVKNEAANLSSLGITALWLPPA
SEQ ID NO 11    (1)  ---HHNGTNGTMMQYFEWHLPNDGNHWNRLRDDAANLKSKGITAVWIPPA
SEQ ID NO 12    (1)  ---HHNGTNGTMMQYFEWYLPNDGNHWNRLRSDASNLKDKGITAVWIPPA
SEQ ID NO 13    (1)  ------KRNHTMMQFFEWHLAADGDHWKRLAEMAPELKAKGIDSVWVPPV
SEQ ID NO 14    (1)  -----DGLNGTMMQYYEWHLENDGQHWNRLHDDAEALSNAGITAIWIPPA
SEQ ID NO 15    (1)  -----DGLNGTMMQYYEWHLENDGQHWNRLHDDAAALSDAGITAIWIPPA
SEQ ID NO 16    (1)  AKYLELEEGGVIMQAFYWDVPGGGIWWDHIRSKIPEWYEAGISAIWLPPP
SEQ ID NO 29    (1)  ----AAPFNGTMMQYFEWYLPDDGTLWTKVANEANNLSSLGITALWLPPA
SEQ ID NO 30    (1)  ------ATNGTMMQYFEWYVPNDGQQWNRLRTDAPYLSSVGITAVWTPPA
SEQ ID NO 31    (1)  AKYSELEKGGVIMQAFYWDVPSGGIWWDTIRQKIPEWYDAGISAIWIPPA 51                                             100
SEQ ID NO C1   (44)  YKGLS-QSDNGYGPYDLYDLGEFQQKGTVRTKYGTKSELQDAIGSLHSRN
SEQ ID NO C2   (48)  YKGTS-SSDVGYGVYDLYDLGEFNQKGTVRTKYGTKTQYIQAIQAAHTAG
SEQ ID NO C3   (46)  YKGTS-QADVGYGAYDLYDLGEFHQKGTVRTKYGTKGELQSAIKSLHSRD
SEQ ID NO C4   (47)  YKGTS-RSDVGYGVYDLYDLGEFNQKGTVRTKYGTKAQYLQAIQAAHAAG
SEQ ID NO C5   (48)  WKGAS-QNDVGYGAYDLYDLGEFNQKGTIRTKYGTRNQLQAAVNALKSNG
SEQ ID NO C6   (48)  WKGTS-QNDVGYGAYDLYDLGEFNQKGTVRTKYGTRNQLQAAVTSLKNNG
SEQ ID NO C7   (48)  WKGTS-QNDVGYGAYDLYDLGEFNQKGTVRTKYGTRSQLESAIHALKNNG
SEQ ID NO C8   (48)  WKGAS-QNDVGYGAYDLYDLGEFNQKGTVRTKYGTRSQLQAAVTSLKNNG
SEQ ID NO C9   (48)  YKGTS-SSDVGYGVYDLYDLGEFNQKGTVRTKYGTKTQYIQAIQAAHTAG
SEQ ID NO 10   (48)  YKGTS-QSDVGYGVYDLYDLGEFNQKGTIRTKYGTKTQYIQAIQAAKAAG
SEQ ID NO 11   (48)  WKGTS-QNDVGYGAYDLYDLGEFNQKGTVRTKYGTRSQLQGAVTSLKNNG
SEQ ID NO 12   (48)  WKGAS-QNDVGYGAYDLYDLGEFNQKGTVRTKYGTRNQLQAAVTALKSNG
SEQ ID NO 13   (45)  TKAVS-AEDTGYGVYDLYDLGEFDQKGTVRTKYGTKQELVEAIAECQKNG
SEQ ID NO 14   (46)  YKGNS-QADVGYGAYDLYDLGEFNQKGTVRTKYGTKAQLERAIGSLKSND
SEQ ID NO 15   (46)  YKGNS-QADVGYGAYDLYDLGEFNQKGTVRTKYGTKAQLERAIGSLKSND
SEQ ID NO 16   (51)  SKGMSGGYSMGYDPYDYFDLGEYYQKGTVETRFGSKEELVRLIQTAHAYG
SEQ ID NO 29   (47)  YKGTS-RSDVGYGVYDLYDLGEFNQKGTVRTKYGTKAQYLQAIQAAHAAG
SEQ ID NO 30   (45)  YKGTS-QADVGYGPYDLYDLGEFNQKGTVRTKYGTKGELKSAVNTLHSNG
SEQ ID NO 31   (51)  SKGMGGAYSMGYDPYDFFDLGEYDQKGTVETRFGSKQELVNMINTAHAYG 101                                             150
SEQ ID NO C1   (93)  VQVYGDVVLNHKAGADATEDVTAVEVNPANRNQETSEEYQIKAWTDFRFP
SEQ ID NO C2   (97)  MQVYADVVFNEKAGADGTELVDAVEVNPSDRNQEISGTYQIQAWTKFDFP
SEQ ID NO C3   (95)  INVYGDVVINEKGGADATEDVTAVEVDPADRNRVISGEHLIKAWTHFHFP
SEQ ID NO C4   (96)  MQVYADVVFDEKGADGTEWVDAVEVNPSDRNQEISGTYQIQAWTKFDFP
SEQ ID NO C5   (97)  IQVYGDVVMNEKGADATEMVRAVEVNPNNRNQEVSGEYTIEAWTKFDFP
SEQ ID NO C6   (97)  IQVYGDVVMNEKGGADGTEIVNAVEVNRSNRNQETSGEYAIEAWTKFDFP
SEQ ID NO C7   (97)  VQVYGDVVMNEKGGADATENVLAVEVNPNNRNQEISGDYTIEAWTKFDFP
SEQ ID NO C8   (97)  IQVYGDVVMNEKGGADATEMVRAVEVNPNNRNQEVTGEYTIEAWTRFDFP
SEQ ID NO C9   (97)  MQVYADVVFNEKAGADGTELVDAVEVNPSDRNQEISGTYQIQAWTKFDFP
SEQ ID NO 10   (97)  MQVYADVVFNEKAGADGTEFVDAVEVDPSNRNQEISGTYQIQAWTKFDFP
SEQ ID NO 11   (97)  IQVYGDVVMNEKGGADGTEMVNAVEVNRSNRNQEISGEYTIEAWTKFDFP
SEQ ID NO 12   (97)  IQVYGDVVMNEKGGADATEWVRAVEVNPSNRNQEVSGDYTIEAWTKFDFP
SEQ ID NO 13   (94)  IAVYVDLVMNEKAGADETEVFKVIEVDPNDRTKEISEPFEIEGWTKFTFP
SEQ ID NO 14   (95)  INVYGDVVMNEKLGADFTEAVQAVQVNPSNRWQDISGVYTIDAWTGFDFP
SEQ ID NO 15   (95)  INVYGDVVMNEKMGADFTEAVQAVQVNPTNRWQDISGAYTIDAWTGFDFS
SEQ ID NO 16  (101)  IKVIADVVINERAGGDLEWNPFVGDYTWTDFSKVASGKYTANYLDFHPNE
SEQ ID NO 29   (96)  MQVYADVVFDEKGADGTEWVDAVEVNPSDRNQEISGTYQIQAWTKFDFP
SEQ ID NO 30   (94)  IQVYGDVVMNEKAGADTENVTAVEVNPSNRNQETSGEYNIQAWTGFNFP
SEQ ID NO 31  (101)  MKVIADIVINERAGGDLEWNPFVNDYTWTDFSKVASGKYTANYLDFHPNE
```

Figure 1

```
                        151                                          200
SEQ ID NO 01   (143) GRGNTYSDFKWHWYHFDGADWDESR-KISRIFKFRGEGKAWDWEVSSENG
SEQ ID NO 02   (147) GRGNTYSSFKWRWYHFDGTDWDESR-KLNRIYKFRGTKAWDWEVDTENG
SEQ ID NO 03   (145) GRGSTYSDFKWHWYHFDGTDWDESR-KLNRIYKFQG--KAWDWEVSNENG
SEQ ID NO 04   (146) GRGNTYSSFKWRWYHFDGVDWDESR-KLSRIYKFRGIGKAWDWEVDTENG
SEQ ID NO 05   (147) GRGNTHSNFKWRWYHFDGVDWDQSRKLNNRIYKFRGDGKGWDWEVDTENG
SEQ ID NO 06   (147) GRGNNHSSFKWRWYHFDGTDWDQSRQLQNKTYKFRGTKAWDWEVDTENG
SEQ ID NO 07   (147) GRGNTYSDFKWRWYHFDGVDWDQSRQFQNRIYKFRGDGKAWDWEVDSENG
SEQ ID NO 08   (147) GRGNTHSSFKWRWYHFDGVDWDQSRRLNNRIYKFRGHGKAWDWEVDTENG
SEQ ID NO 09   (147) GRGNTYSSFKWRWYHFDGTDWDESR-KLNRIYKFRGTKAWDWEVDTENG
SEQ ID NO 10   (147) GRGNTYSSFKWRWYHFDGTDWDESR-KLNRIYKFRSTGKAWDWEVDTENG
SEQ ID NO 11   (147) GRGNTHSNFKWRWYHFDGTDWDQSRQLQNKIYKFRGTGKAWDWEVDIENG
SEQ ID NO 12   (147) GRGNTHSNFKWRWYHFDGVDWDQSRQLQNRIYKFRGDGKGWDWEVDTENG
SEQ ID NO 13   (144) GRGDQYSSFKWNSEHFNGTDFDAKG-ERTGVFRIAGENKKWNENVDDEFG
SEQ ID NO 14   (145) GRNNAYSDFKWRWFHFNGVDWDQRY-QENHLFRFAN--TNWNWRVDEENG
SEQ ID NO 15   (145) GRNNAYSDFKWRWFHFNGVDWDQRY-QENHIFRFAN--TNWNWRVDEENG
SEQ ID NO 16   (151) LHCCDEGT------------------------------------------
SEQ ID NO 29   (146) CRCNTYSSFKWRWYHFDCVDWDESR-KLSRIYKFRGICKAWDWEVDTENG
SEQ ID NO 30   (144) GRGTTYSNFKWQWFHFDGTDWDQSR-SLSRIFKFRGTGKAWDWEVSSENG
SEQ ID NO 31   (151) LHACDSCT------------------------------------------

201                                          250
SEQ ID NO 01   (192) NYDYLMYADVDYDHPDVVAETK    KWGIWYANELSLDGFRIDAAKHIK
SEQ ID NO 02   (196) NYDYLMYADLDMDHPEVVSELK----NWGKWYVTTTNIDGFRLDAVKHIK
SEQ ID NO 03   (192) NYDYLMYADIDYDHPDVAAEIK----RWGTWYANELQLDGFRLDAVKHIK
SEQ ID NO 04   (195) NYDYLMYADLDMDHPEVVTELK----NWGKWYVNTTNIDGFRLDAVKHIK
SEQ ID NO 05   (197) NYDYLMYADIDMDHPEVVNELR----NWGVWYTNTLGLDGFRIDAVKHIK
SEQ ID NO 06   (197) NYDYLMYADVDMDHPEVIEELR----NWGVWYTNTLNLDGFRIDAVKHIK
SEQ ID NO 07   (197) NYDYLMYADVDMDHPEVVNELR----RWGEWYTNTLNLDGFRIDAVKHIK
SEQ ID NO 08   (197) NYDYLMYADIDMDHPEVVNELR----NWGWYTNTLGLDGFRIDAVKHIK
SEQ ID NO 09   (196) NYDYLMYADLDMDHPEVVSELK----NWGKWYVITTNIDGFRLDAVKHIK
SEQ ID NO 10   (196) NYDYLMFADLDMDHPEVVTELK----NWGTWYVNTTNIDGFRLDAVKHIK
SEQ ID NO 11   (197) NYDYLMYADIDMDHPEVINELR----NWGWYTNTLNLDGFRIDAVKHIK
SEQ ID NO 12   (197) NYDYLMYADIDMDHPEVVNELR----NWGWYTNTLGLDGFRIDAVKHIK
SEQ ID NO 13   (193) NYDYLMFANIDYNHPDVRREMI----DWGKWLIDTLQCGGFRLDAIKHIN
SEQ ID NO 14   (192) NYDYLLGSNIDFSHPEVQEELK----DWGSWFTDELDLDGYRLDAIKHIP
SEQ ID NO 15   (192) NYDYLLGSNIDFSHPEVQDELK----DWGSWFTDELDLDGYRLDAIKHIP
SEQ ID NO 16   (159) ---FGGFPDICHHKEWDQYWLWKSNESYAAYLRS-IGFDGWRFDYVKGYG
SEQ ID NO 29   (195) NYDYLMYADLDMDHPEVVTELK----NWGKWYVNTTNIDGFRLDAVKHIK
SEQ ID NO 30   (193) NYDYLMYADIDYDHPDVVNEMK----KWGVWYANEVGLDGYRLDAVKHIK
SEQ ID NO 31   (159) ---FGGYPDICHDKSWDQYWLWASQESYAAYLRS-IGIDAWRFDYVKGYA 251                                          300
SEQ ID NO 01   (238) FSFLRDWVQAVRQATGKEMFTVAEYWQNNAGKLENYLNKTSFNQSVFDVP
SEQ ID NO 02   (242) YSFFPDWLSYVRTQTQKPLFAVGEFWSYDISKLHNYITKTNGSMSLFDAP
SEQ ID NO 03   (238) FSFLRDWVNHVREKTGKEMFTVAEYWQNDLGALENYLNKTNFNHSVFDVP
SEQ ID NO 04   (241) FSFFPDWLSYVRSQTGKPLFTVGEYWSYDINKLHNYITKTNGTMSLFDAP
SEQ ID NO 05   (243) YSFTRDWINHVRSATGKNMFAVAEFWKNDLGAIENYLNKTNWNHSVFDVP
SEQ ID NO 06   (243) YSFTRDWLTHVRNTTGKPMFAVAEFWKNDLGAIENYLNKTSWNHSVFDVP
SEQ ID NO 07   (243) YSFTRDWLTHVRNATGKEMFAVAEFWKNDLGALENYLNKTNWNHSVFDVP
SEQ ID NO 08   (243) YSFTRDWINHVRSATGKNMFAVAEFWKNDLGAIENYLQKTNWNHSVFDVP
SEQ ID NO 09   (242) YSFFPDWLSYLRTQTQKPLFAVGEFWSYDINKLHNYITKTNGSMSLFDAP
SEQ ID NO 10   (242) YSFFPDWLTYVRNQTGKNLFAVGEFWSYDVNKLHNYITKTNGSMSLFDAP
SEQ ID NO 11   (243) YSYTRDWLTHVRNTTGKPMFAVAEFWKNDLAAIENYLNKTSWNHSVFDVP
SEQ ID NO 12   (243) YSFTRDWLTHVRNTTGKNMFAVAEFWKNDIGAIENYLSKTNWNHSVFDVP
SEQ ID NO 13   (239) HEFIKEFASEMIRKRGQDFYIVGEFWNSNLDACREFLDTVDYQIDLFDVS
SEQ ID NO 14   (238) FWYTSDWVRHQRSEADQDLFVVGEYWKDDVGALEFYLDEMNWEMSLFDVP
SEQ ID NO 15   (238) FWYTSDWVRHQRNEADQDLFVVGEYWKDDVGALEFYLDEMNWEMSLFDVP
SEQ ID NO 16   (205) AWVVRDWLNWNGG------WAVGEYWDTNVDALLSWAYES--GAKVFDFP
SEQ ID NO 29   (241) FSFFPDWLSYVRSQTGKPLFTVGEYWSYDINKLHNYITKTNGTMSLFDAP
SEQ ID NO 30   (239) FSFLKDWVDNARAATGKEMFTVGEYWQNDLGALNNYLAKVNYNQSLFDAP
SEQ ID NO 31   (205) PWVVKDWLNWNGG------WAVGEYWDTNVDAVLNWAYSS--GAKVFDFA
```

Figure 1 cont.

```
                    301                                            350
SEQ ID NO 01   (288) LHFNLQAASSQGGGYDMRRLLDG--TVVSRHPEKAVTFVENEDTQPGQSL
SEQ ID NO 02   (292) LHNNFYIASKSGGYFDMRTLLNN--TLMKDQPTLAVTLVDNEDTEPGQSL
SEQ ID NO 03   (288) LHYQFHAASTQGGGYDMRKLLNG--TVVSKHPLKSVTFVDNEDTQPGQSL
SEQ ID NO 04   (291) LHNKFYTASKSGGAFDMRTLMTN  TLMKDQPTLAVTFVDNEDTEPGQAL
SEQ ID NO 05   (293) LHYNLYNASKSGGNYDMRQIFNG--TVVQRHPMHAVTFVDNEDSQPEEAL
SEQ ID NO 06   (293) LHYNLYNASNSGGYYDMRNILNG--SVVQKHPTHAVTFVDNEDSQPGEAL
SEQ ID NO 07   (293) LHYNLYNASNSGGNYDMAKLLNG--TVVQKHPMHAVTFVDNEDSQPGESL
SEQ ID NO 08   (293) LHYNLYNASKSGGNYDMRNIFNG--TVVQRHPSHAVTFVDNEDSQPEEAL
SEQ ID NO 09   (292) LHNNFYIASKSGGYFDMRTLLNN--TLMKEQPTLSVTLVDNEDTEPGQSL
SEQ ID NO 10   (292) LHNNFYTASKSSGYFDMRYLLNN--TLMKDQPSLAVTLVDNEDTQPGQSL
SEQ ID NO 11   (293) LHYNLYNASNSGGYFDMRNILNG--SVVQKHPIHAVTFVDNEDSQPGEAL
SEQ ID NO 12   (293) LHYNLYNASRSGGNYDMRQIFNG--TVVQRHPTHAVTFVDNEDSQPEEAL
SEQ ID NO 13   (289) LHYKLHEASLAGRDFDLSKIFDD--TLVQTHPTHAVTFVDNEDSQPHEAL
SEQ ID NO 14   (288) LNYNFYRASKQCCSYDMRNILRC--SLVEAHPIHAVTFVDNEDTQPCESL
SEQ ID NO 15   (288) LNYNFYRASQQGGSYDMRNILRG--SLVEAHPMHAVTFVDNEDTQPGESL
SEQ ID NO 16   (247) LYYKMDEAFDNNNIPALVYALQNGQTVVSRDPFKAVTFVANEDTD-----
SEQ ID NO 29   (291) LHNKFYTASKSGGAFDMRTLMTN--TLMKDQPTLAVTFVDNEDTEPGQAL
SEQ ID NO 30   (289) LHYNFYAASTGGGYYDMRNILNN--TLVASNPTKAVTLVENEDTQPGQSL
SEQ ID NO 31   (247) LYYKMDEAFDNKNIPALVSALQNGQTVVSRDPFKAVTFVANEDTD-----

351                                            400
SEQ ID NO 01   (336) ESTVQTWFKPLAYAFILTRESGYPQVFYGDMYGTKGTSPKEIPSLKDNIE
SEQ ID NO 02   (340) QSWVEPWFKPLAYAFILTRQEGYPCVFYGDYYGIPKYN---IPALKSKLD
SEQ ID NO 03   (336) ESTVQTWFKPLAYAFILTRESGYPQVFYGDMYGTKGDSQREIPALKEKIE
SEQ ID NO 04   (339) QSWVDPWFKPLAYAFILTRQEGYPCVFYGDYYGIPQYN---IPSLKSKID
SEQ ID NO 05   (341) ESFVEEWFKPLAYALTLTREQGYPSVFYGDYYGIPTHG---VPAMKSKID
SEQ ID NO 06   (341) ESFVQQWFKPLAYALVLTREQGYPSVFYGDYYGIPTHG   VPAMKSKID
SEQ ID NO 07   (341) ESFVQEWFKPLAYALILTREQGYPSVFYGDYYGIPTHS---VPAMKAKID
SEQ ID NO 08   (341) ESFVEEWFKPLAYALTLTREQGYPSVFYGDYYGIPTHG---VPAMRSKID
SEQ ID NO 09   (340) QSWVEPWFKPLAYAFILTRQEGYPCVFYGDYYGIPKYN---IPALKSKLD
SEQ ID NO 10   (340) QSWVEPWFKPLAYAFILTRQEGYPCVFYGDYYGIPKYN---IPGLKSKID
SEQ ID NO 11   (341) ESFVQSWFKPLAYALILTREQGYPSVFYGDYYGIPTHG---VPSMKSKID
SEQ ID NO 12   (341) ESFVEEWFKPLAYALTLTRDQGYPSVFYGDYYGIPTHG---VPAMKSKID
SEQ ID NO 13   (337) ESWIGDWFKPSAYALTLLRRDGYPVVFYGDYYGIGGPEP--VDGKKEILD
SEQ ID NO 14   (336) ESWVADWFKPLAYATILTREGGYPNVFYGDYYGIPNDN---ISAKKDMID
SEQ ID NO 15   (336) ESWVADWFKPLAYATILTREGGYPNVFYGDYYGIPNDN---ISAKKDMID
SEQ ID NO 16   (292) ----IIWNKYPAYAFILTYE-CQPVIFYRDFEEWLN---------KDKLI
SEQ ID NO 29   (339) QSWVDPWFKPLAYAFILTRQEGYPCVFYGDYYGIPQYN---IPSLKSKID
SEQ ID NO 30   (337) ESTVQPWFKPLAYAFILTRSGGYPSVFYGDMYGTKGTTTREIPALKSKIE
SEQ ID NO 31   (292) ----IIWNKYPAYAFILTYE-GQPTIFYRDYEEWLN---------KDKLK 401                                            450
SEQ ID NO 01   (386) PILKARKEYAYGPQHDYIDHPDVIGWTREGDSSAAKSGLAALITDGPGGS
SEQ ID NO 02   (387) PLLIARRDYAYGTQHDYIDSADIIGWTREGVAEKANSGLAALITDGPGGS
SEQ ID NO 03   (386) PILKARKQYAYGAQHDYFDHHDIVGWTREGDSSVANSGLAALITDGPGGA
SEQ ID NO 04   (386) PLLIARRDYAYGTQHDYLDHSDIIGWTREGVTEKPGSGLAALITDGPGGS
SEQ ID NO 05   (388) PILEARQKYAYGRQNDYLDHHNIIGWTREGNTAHPNSGLATIMSDGAGGN
SEQ ID NO 06   (388) PLLQARQTFAYGTQHDYFDHHDIIGWTREGNSSHPNSGLATIMSDGPGGN
SEQ ID NO 07   (388) PILEARQNFAYGTQHDYFDHHNIIGWTREGNTTHPNSGLATIMSDGPGGE
SEQ ID NO 08   (388) PILEARQKYAYGKQNDYLDHHNIIGWTREGNTAHPNSGLATIMSDGAGGS
SEQ ID NO 09   (387) PLLIARRDYAYGTQHDYIDNADIIGWTREGVAEKANSGLAALITDGPGGS
SEQ ID NO 10   (387) PLLIARRDYAYGTQRDYIDHQDIIGWTREGIDTKPNSGLAALITDGPGGS
SEQ ID NO 11   (388) PLLQARQTYAYGTQHDYFDHHDIIGWTREGDSSHPNSGLATIMSDGPGGN
SEQ ID NO 12   (388) PILEARQKYAYGKQNDYLDHHNMIGWTREGNTAHPNSGLATIMSDGPGGN
SEQ ID NO 13   (385) ILLSARCNKAYGEQEDYFDHANTIGWVRRGVEEIEGSGCAVVISNGDDGE
SEQ ID NO 14   (383) ELLDARQNYAYGTQHDYFDHWDIVGWTREGTSSRPNSGLATIMSNGPGGS
SEQ ID NO 15   (383) ELLDARQNYAYGTQHDYFDHWDVVGWTREGSSSRPNSGLATIMSNGPGGS
SEQ ID NO 16   (328) NLIWIHDHLAGGSTTIVYYDNDELIFVRNGDSRRP--GLITYINLSPNWV
SEQ ID NO 29   (386) PLLIARRDYAYGTQHDYLDHSDIIGWTREGVTEKPGSGLAALITDGPGGS
SEQ ID NO 30   (387) PLLKARKDYAYCTQRDYIDNPDVICWTRECDSTKAKSCLATVITDCPCCS
SEQ ID NO 31   (328) NLIWIHENLAGGSTDIVYYDNDELIFVRNGYGDKP--GLITYINLGSSKA
```

Figure 1 cont.

```
                          451                                           500
SEQ ID NO 01  (436) KRMYAGLKNAGETWYDITGNRSDTVKIGSDGWGEFHVNDGSVSIYVQK--
SEQ ID NO 02  (437) KWMYVGKQHAGKTFYDLTGNRSDTVTINADGWGEFKVNGGSVSIWVPKIS
SEQ ID NO 03  (436) KRMYVGRQNAGETWHDITGNRSEPVVINSEGWGEFHVNGGSVSIYVQR--
SEQ ID NO 04  (436) KWMYVGKQHAGKVFYDLTGNRSDTVTINSDGWGEFKVNGGSVSVWVPRKT
SEQ ID NO 05  (438) KWMFVGRNKAGQVWTDITGNRAGTVTINADGWGNFSVNGGSVSIWVNK--
SEQ ID NO 06  (438) KWMYVGKNKAGQVWRDITGNRTGTVTINADGWGNFSVNGGSVSVWVKQ--
SEQ ID NO 07  (438) KWMYVGQNKAGQVWHDITGNKPGTVTTNADGWANFSVNGGSVSIWVKR--
SEQ ID NO 08  (438) KWMFVGRNKAGQVWSDITGNRTGTVTINADGWGNFSVNGGSVSIWVNK--
SEQ ID NO 09  (437) KWMYVGKQHAGKTFYDLTGNRSDTVTINADGWGEFKVNGGSVSIWVPKTS
SEQ ID NO 10  (437) KWMYVGKKHAGKVFYDLTGNRSDTVTINADGWGEFKVNGGSVSIWVAKTS
SEQ ID NO 11  (438) KWMYVGKHKAGQVWRDITGNRSGTVTINADGWGNFTVNGGAVSVWVKQ--
SEQ ID NO 12  (438) KWMYVGRNKAGQVWRDITGNRSGTVTINADGWGNFSVNGGSVSIWVNN--
SEQ ID NO 13  (435) KRMFIGEHRAGEVWVDLTKSCDDHITIEEDGWATFHVCGGGVSVWALPEQ
SEQ ID NO 14  (433) KWMYVGQQHAGQTWTDLTGNHAASVTINGDGWGEFFTNGGSVSVYVNQ--
SEQ ID NO 15  (433) KWMYVGRQNAGQTWTDLTGNNGASVTINGDGWGEFFTNGGSVSVYVNQ--
SEQ ID NO 16  (376) GRWVYVPKFAGACIHEYTGNLGGWVDKRVDSSGWVYLEAPPHDPANGYYG
SEQ ID NO 29  (436) KWMYVGKQHAGKVFYDLTGNRSDTVTINSDGWGEFKVNGGSVSVWVPRKT
SEQ ID NO 30  (437) KRMYVGTSNAGEIWYDLTGNRTDKITIGSDGYATFPVNGGSVSVWVQQ--
SEQ ID NO 31  (376) GRWVYVPKFAGACIHEYTGNLGGWVDKYVYSSGWVYLEAPAYDPANGQYG 501                                           550
SEQ ID NO 01  (484) --------------------------------------------------
SEQ ID NO 02  (487) TTSQITFTVNNATTVWGQNVYVVGNISQLGNWDPVHAVQMTPSSYPTWTV
SEQ ID NO 03  (484) --------------------------------------------------
SEQ ID NO 04  (486) TVSTIARPI---TTRPWTGEFVRWTEPRLVAWP-----------------
SEQ ID NO 05  (486) --------------------------------------------------
SEQ ID NO 06  (486) --------------------------------------------------
SEQ ID NO 07  (486) --------------------------------------------------
SEQ ID NO 08  (486) --------------------------------------------------
SEQ ID NO 09  (487) TTSQITFTVNNATTVWGQNVYVVGNISQLGNWDPVNAVQMTPSSYPTWVV
SEQ ID NO 10  (487) N---VTFTVNNATTTSGQNVYVVANIPELGNWNTANAIKMNPSSYFTWKA
SEQ ID NO 11  (486) --------------------------------------------------
SEQ ID NO 12  (486) --------------------------------------------------
SEQ ID NO 13  (485) NEDCADAE------------------------------------------
SEQ ID NO 14  (481) --------------------------------------------------
SEQ ID NO 15  (481) --------------------------------------------------
SEQ ID NO 16  (426) YSVWSYCCVC----------------------------------------
SEQ ID NO 29  (486) T-------------------------------------------------
SEQ ID NO 30  (485) --------------------------------------------------
SEQ ID NO 31  (426) YSVWSYCGVG----------------------------------------

551                                           600
SEQ ID NO 01  (484) --------------------------------------------------
SEQ ID NO 02  (537) TIPLLQGQNIQFKFIKKDSAGNVIWEDISNRTYIVPTAASGAYTASWNVP
SEQ ID NO 03  (484) --------------------------------------------------
SEQ ID NO 04  (516) --------------------------------------------------
SEQ ID NO 05  (486) --------------------------------------------------
SEQ ID NO 06  (486) --------------------------------------------------
SEQ ID NO 07  (486) --------------------------------------------------
SEQ ID NO 08  (486) --------------------------------------------------
SEQ ID NO 09  (537) TVPLPQSQNIQFKFIKKDGSGNVIWENISNRTYIVPTAASGAYTANWNVP
SEQ ID NO 10  (534) TIALPQGKAIEFKFIKKDQAGNVIWESTSNRTYIVPFSSTGSYTASWNVP
SEQ ID NO 11  (486) --------------------------------------------------
SEQ ID NO 12  (486) --------------------------------------------------
SEQ ID NO 13  (493) --------------------------------------------------
SEQ ID NO 14  (481) --------------------------------------------------
SEQ ID NO 15  (481) --------------------------------------------------
SEQ ID NO 16  (436) --------------------------------------------------
SEQ ID NO 29  (487) --------------------------------------------------
SEQ ID NO 30  (485) --------------------------------------------------
SEQ ID NO 31  (436) --------------------------------------------------
```

Figure 1 cont.

SEQUENCE LISTING

```
<160> NUMBER OF SEQ ID NOS: 34

<210> SEQ ID NO 1
<211> LENGTH: 483
<212> TYPE: PRT
<213> ORGANISM: Bacillus amyloliquefaciens

<400> SEQUENCE: 1

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Gly Leu Ser
        35                  40                  45

Gln Ser Asp Asn Gly Tyr Gly Pro Tyr Asp Leu Tyr Asp Leu Gly Glu
    50                  55                  60

Phe Gln Gln Lys Gly Thr Val Arg Thr Lys Tyr Gly Thr Lys Ser Glu
65                  70                  75                  80

Leu Gln Asp Ala Ile Gly Ser Leu His Ser Arg Asn Val Gln Val Tyr
                85                  90                  95

Gly Asp Val Val Leu Asn His Lys Ala Gly Ala Asp Ala Thr Glu Asp
            100                 105                 110

Val Thr Ala Val Glu Val Asn Pro Ala Asn Arg Asn Gln Glu Thr Ser
        115                 120                 125

Glu Glu Tyr Gln Ile Lys Ala Trp Thr Asp Phe Arg Phe Pro Gly Arg
    130                 135                 140
```

```
Gly Asn Thr Tyr Ser Asp Phe Lys Trp His Trp Tyr His Phe Asp Gly
145                 150                 155                 160

Ala Asp Trp Asp Glu Ser Arg Lys Ile Ser Arg Ile Phe Lys Phe Arg
            165                 170                 175

Gly Glu Gly Lys Ala Trp Asp Trp Glu Val Ser Ser Glu Asn Gly Asn
        180                 185                 190

Tyr Asp Tyr Leu Met Tyr Ala Asp Val Asp Tyr Asp His Pro Asp Val
            195                 200                 205

Val Ala Glu Thr Lys Lys Trp Gly Ile Trp Tyr Ala Asn Glu Leu Ser
        210                 215                 220

Leu Asp Gly Phe Arg Ile Asp Ala Ala Lys His Ile Lys Phe Ser Phe
225                 230                 235                 240

Leu Arg Asp Trp Val Gln Ala Val Arg Gln Ala Thr Gly Lys Glu Met
                245                 250                 255

Phe Thr Val Ala Glu Tyr Trp Gln Asn Asn Ala Gly Lys Leu Glu Asn
            260                 265                 270

Tyr Leu Asn Lys Thr Ser Phe Asn Gln Ser Val Phe Asp Val Pro Leu
        275                 280                 285

His Phe Asn Leu Gln Ala Ala Ser Ser Gln Gly Gly Gly Tyr Asp Met
    290                 295                 300

Arg Arg Leu Leu Asp Gly Thr Val Val Ser Arg His Pro Glu Lys Ala
305                 310                 315                 320

Val Thr Phe Val Glu Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Thr Ser Pro Lys Glu Ile Pro Ser Leu Lys Asp Asn Ile
    370                 375                 380

Glu Pro Ile Leu Lys Ala Arg Lys Glu Tyr Ala Tyr Gly Pro Gln His
385                 390                 395                 400

Asp Tyr Ile Asp His Pro Asp Val Ile Gly Trp Thr Arg Glu Gly Asp
                405                 410                 415

Ser Ser Ala Ala Lys Ser Gly Leu Ala Ala Leu Ile Thr Asp Gly Pro
            420                 425                 430

Gly Gly Ser Lys Arg Met Tyr Ala Gly Leu Lys Asn Ala Gly Glu Thr
        435                 440                 445

Trp Tyr Asp Ile Thr Gly Asn Arg Ser Asp Thr Val Lys Ile Gly Ser
    450                 455                 460

Asp Gly Trp Gly Glu Phe His Val Asn Asp Gly Ser Val Ser Ile Tyr
465                 470                 475                 480

Val Gln Lys

<210> SEQ ID NO 2
<211> LENGTH: 584
<212> TYPE: PRT
<213> ORGANISM: Bacillus flavothermus

<400> SEQUENCE: 2

Val Pro Val Asn Gly Thr Met Met Gln Tyr Phe Glu Trp Tyr Leu Pro
1               5                   10                  15

Asp Asp Gly Thr Leu Trp Thr Lys Val Ala Asn Asn Ala Gln Ser Leu
            20                  25                  30
```

-continued

```
Ala Asn Leu Gly Ile Thr Ala Leu Trp Leu Pro Pro Ala Tyr Lys Gly
             35                  40                  45

Thr Ser Ser Asp Val Gly Tyr Gly Val Tyr Asp Leu Tyr Asp Leu
 50                  55                  60

Gly Glu Phe Asn Gln Lys Gly Thr Val Arg Thr Lys Tyr Gly Thr Lys
 65                  70                  75                  80

Thr Gln Tyr Ile Gln Ala Ile Gln Ala Ala His Thr Ala Gly Met Gln
                 85                  90                  95

Val Tyr Ala Asp Val Val Phe Asn His Lys Ala Gly Ala Asp Gly Thr
            100                 105                 110

Glu Leu Val Asp Ala Val Glu Val Asn Pro Ser Asp Arg Asn Gln Glu
        115                 120                 125

Ile Ser Gly Thr Tyr Gln Ile Gln Ala Trp Thr Lys Phe Asp Phe Pro
130                 135                 140

Gly Arg Gly Asn Thr Tyr Ser Ser Phe Lys Trp Arg Trp Tyr His Phe
145                 150                 155                 160

Asp Gly Thr Asp Trp Asp Glu Ser Arg Lys Leu Asn Arg Ile Tyr Lys
                165                 170                 175

Phe Arg Gly Thr Gly Lys Ala Trp Asp Trp Glu Val Asp Thr Glu Asn
            180                 185                 190

Gly Asn Tyr Asp Tyr Leu Met Tyr Ala Asp Leu Asp Met Asp His Pro
        195                 200                 205

Glu Val Val Ser Glu Leu Lys Asn Trp Gly Lys Trp Tyr Val Thr Thr
    210                 215                 220

Thr Asn Ile Asp Gly Phe Arg Leu Asp Ala Val Lys His Ile Lys Tyr
225                 230                 235                 240

Ser Phe Phe Pro Asp Trp Leu Ser Tyr Val Arg Thr Gln Thr Gln Lys
                245                 250                 255

Pro Leu Phe Ala Val Gly Glu Phe Trp Ser Tyr Asp Ile Ser Lys Leu
            260                 265                 270

His Asn Tyr Ile Thr Lys Thr Asn Gly Ser Met Ser Leu Phe Asp Ala
        275                 280                 285

Pro Leu His Asn Asn Phe Tyr Ile Ala Ser Lys Ser Gly Gly Tyr Phe
    290                 295                 300

Asp Met Arg Thr Leu Leu Asn Asn Thr Leu Met Lys Asp Gln Pro Thr
305                 310                 315                 320

Leu Ala Val Thr Leu Val Asp Asn His Asp Thr Glu Pro Gly Gln Ser
                325                 330                 335

Leu Gln Ser Trp Val Glu Pro Trp Phe Lys Pro Leu Ala Tyr Ala Phe
            340                 345                 350

Ile Leu Thr Arg Gln Glu Gly Tyr Pro Cys Val Phe Tyr Gly Asp Tyr
        355                 360                 365

Tyr Gly Ile Pro Lys Tyr Asn Ile Pro Ala Leu Lys Ser Lys Leu Asp
    370                 375                 380

Pro Leu Leu Ile Ala Arg Arg Asp Tyr Ala Tyr Gly Thr Gln His Asp
385                 390                 395                 400

Tyr Ile Asp Ser Ala Asp Ile Ile Gly Trp Thr Arg Glu Gly Val Ala
                405                 410                 415

Glu Lys Ala Asn Ser Gly Leu Ala Ala Leu Ile Thr Asp Gly Pro Gly
            420                 425                 430

Gly Ser Lys Trp Met Tyr Val Gly Lys Gln His Ala Gly Lys Thr Phe
        435                 440                 445

Tyr Asp Leu Thr Gly Asn Arg Ser Asp Thr Val Thr Ile Asn Ala Asp
    450                 455                 460
```

```
Gly Trp Gly Glu Phe Lys Val Asn Gly Ser Val Ser Ile Trp Val
465                 470                 475                 480

Pro Lys Ile Ser Thr Thr Ser Gln Ile Thr Phe Thr Val Asn Asn Ala
            485                 490                 495

Thr Thr Val Trp Gly Gln Asn Val Tyr Val Val Gly Asn Ile Ser Gln
                500                 505                 510

Leu Gly Asn Trp Asp Pro Val His Ala Val Gln Met Thr Pro Ser Ser
            515                 520                 525

Tyr Pro Thr Trp Thr Val Thr Ile Pro Leu Leu Gln Gly Gln Asn Ile
        530                 535                 540

Gln Phe Lys Phe Ile Lys Lys Asp Ser Ala Gly Asn Val Ile Trp Glu
545                 550                 555                 560

Asp Ile Ser Asn Arg Thr Tyr Thr Val Pro Thr Ala Ala Ser Gly Ala
                565                 570                 575

Tyr Thr Ala Ser Trp Asn Val Pro
                580

<210> SEQ ID NO 3
<211> LENGTH: 483
<212> TYPE: PRT
<213> ORGANISM: Bacillus licheniformis

<400> SEQUENCE: 3

Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255
```

```
Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
            275                 280                 285

His Tyr Gln Phe His Ala Ala Ser Thr Gln Gly Gly Gly Tyr Asp Met
290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
            325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
            355                 360                 365

Thr Lys Gly Asp Ser Gln Arg Glu Ile Pro Ala Leu Lys His Lys Ile
            370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
            405                 410                 415

Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
            435                 440                 445

Trp His Asp Ile Thr Gly Asn Arg Ser Glu Pro Val Val Ile Asn Ser
450                 455                 460

Glu Gly Trp Gly Glu Phe His Val Asn Gly Gly Ser Val Ser Ile Tyr
465                 470                 475                 480

Val Gln Arg

<210> SEQ ID NO 4
<211> LENGTH: 515
<212> TYPE: PRT
<213> ORGANISM: Bacillus stearothermophilus

<400> SEQUENCE: 4

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140
```

```
Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
            165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
            245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asp Gly Thr Met Ser Leu Phe Asp
        275                 280                 285

Ala Pro Leu His Asn Lys Phe Tyr Thr Ala Ser Lys Ser Gly Gly Ala
290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
            325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Gly
            405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
            485                 490                 495

Arg Pro Trp Thr Gly Glu Phe Val Arg Trp Thr Glu Pro Arg Leu Val
            500                 505                 510

Ala Trp Pro
        515

<210> SEQ ID NO 5
<211> LENGTH: 485
<212> TYPE: PRT
<213> ORGANISM: Bacillus

<400> SEQUENCE: 5
```

-continued

```
His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
            35                  40                  45

Lys Gly Ala Ser Gln Asn Asp Val Gly Tyr Gly Ala Tyr Asp Leu Tyr
        50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
            115                 120                 125

Gln Glu Val Ser Gly Glu Tyr Thr Ile Glu Ala Trp Thr Lys Phe Asp
        130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
            245                 250                 255

Thr Gly Lys Asn Met Phe Ala Val Ala Glu Phe Trp Lys Asn Asp Leu
        260                 265                 270

Gly Ala Ile Glu Asn Tyr Leu Asn Lys Thr Asn Trp Asn His Ser Val
        275                 280                 285

Phe Asp Val Pro Leu His Tyr Asn Leu Tyr Asn Ala Ser Lys Ser Gly
290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
            325                 330                 335

Glu Glu Ala Leu Glu Ser Phe Val Glu Trp Phe Lys Pro Leu Ala
        340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Lys Ser
370                 375                 380

Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
            405                 410                 415

Gly Asn Thr Ala His Pro Asn Ser Gly Leu Ala Thr Ile Met Ser Asp
        420                 425                 430
```

```
Gly Ala Gly Gly Asn Lys Trp Met Phe Val Gly Arg Asn Lys Ala Gly
            435                 440                 445

Gln Val Trp Thr Asp Ile Thr Gly Asn Arg Ala Gly Thr Val Thr Ile
450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 6
<211> LENGTH: 484
<212> TYPE: PRT
<213> ORGANISM: Bacillus

<400> SEQUENCE: 6

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Asp Asp Ala Ala
            20                  25                  30

Asn Leu Lys Ser Lys Gly Ile Thr Ala Val Trp Ile Pro Pro Ala Trp
        35                  40                  45

Lys Gly Thr Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ser Leu Lys Asn Asn Gly
            85                  90                  95

Ile Gln Val Tyr Gly Asp Val Val Met Asn His Lys Gly Gly Ala Asp
        100                 105                 110

Gly Thr Glu Ile Val Asn Ala Val Glu Val Asn Arg Ser Asn Arg Asn
    115                 120                 125

Gln Glu Thr Ser Gly Glu Tyr Ala Ile Glu Ala Trp Thr Lys Phe Asp
130                 135                 140

Phe Pro Gly Arg Gly Asn Asn His Ser Ser Phe Lys Trp Arg Trp Tyr
145                 150                 155                 160

His Phe Asp Gly Thr Asp Trp Asp Gln Ser Arg Gln Leu Gln Asn Lys
            165                 170                 175

Ile Tyr Lys Phe Arg Gly Thr Gly Lys Ala Trp Asp Trp Glu Val Asp
        180                 185                 190

Thr Glu Asn Gly Asn Tyr Asp Tyr Leu Met Tyr Ala Asp Val Asp Met
    195                 200                 205

Asp His Pro Glu Val Ile His Glu Leu Arg Asn Trp Gly Val Trp Tyr
210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Thr
            245                 250                 255

Thr Gly Lys Pro Met Phe Ala Val Ala Glu Phe Trp Lys Asn Asp Leu
        260                 265                 270

Gly Ala Ile Glu Asn Tyr Leu Asn Lys Thr Ser Trp Asn His Ser Val
    275                 280                 285

Phe Asp Val Pro Leu His Tyr Asn Leu Tyr Asn Ala Ser Asn Ser Gly
290                 295                 300

Gly Tyr Tyr Asp Met Arg Asn Ile Leu Asn Gly Ser Val Val Gln Lys
305                 310                 315                 320
```

```
His Pro Thr His Ala Val Thr Phe Val Asp Asn His Asp Ser Gln Pro
            325                 330                 335
Gly Glu Ala Leu Glu Ser Phe Val Gln Gln Trp Phe Lys Pro Leu Ala
            340                 345                 350
Tyr Ala Leu Val Leu Thr Arg Glu Gln Gly Tyr Pro Ser Val Phe Tyr
            355                 360                 365
Gly Asp Tyr Tyr Gly Ile Pro Thr His Gly Val Pro Ala Met Lys Ser
            370                 375                 380
Lys Ile Asp Pro Leu Leu Gln Ala Arg Gln Thr Phe Ala Tyr Gly Thr
385                 390                 395                 400
Gln His Asp Tyr Phe Asp His Asp Ile Ile Gly Trp Thr Arg Glu
            405                 410                 415
Gly Asn Ser Ser His Pro Asn Ser Gly Leu Ala Thr Ile Met Ser Asp
            420                 425                 430
Gly Pro Gly Gly Asn Lys Trp Met Tyr Val Gly Lys Asn Lys Ala Gly
            435                 440                 445
Gln Val Trp Arg Asp Ile Thr Gly Asn Arg Thr Gly Thr Val Thr Ile
            450                 455                 460
Asn Ala Asp Gly Trp Gly Asn Phe Ser Val Asn Gly Gly Ser Val Ser
465                 470                 475                 480
Val Trp Val Lys

<210> SEQ ID NO 7
<211> LENGTH: 485
<212> TYPE: PRT
<213> ORGANISM: Bacillus

<400> SEQUENCE: 7

His His Asn Gly Thr Asn Gly Thr Met Met Gln Tyr Phe Glu Trp His
1               5                   10                  15
Leu Pro Asn Asp Gly Asn His Trp Asn Arg Leu Arg Asp Asp Ala Ser
            20                  25                  30
Asn Leu Arg Asn Arg Gly Ile Thr Ala Ile Trp Ile Pro Pro Ala Trp
            35                  40                  45
Lys Gly Thr Ser Gln Asn Asp Val Gly Tyr Gly Ala Tyr Asp Leu Tyr
            50                  55                  60
Asp Leu Gly Glu Phe Asn Gln Lys Gly Thr Val Arg Thr Lys Tyr Gly
65                  70                  75                  80
Thr Arg Ser Gln Leu Glu Ser Ala Ile His Ala Leu Lys Asn Asn Gly
            85                  90                  95
Val Gln Val Tyr Gly Asp Val Val Met Asn His Lys Gly Gly Ala Asp
            100                 105                 110
Ala Thr Glu Asn Val Leu Ala Val Glu Val Asn Pro Asn Asn Arg Asn
            115                 120                 125
Gln Glu Ile Ser Gly Asp Tyr Thr Ile Glu Ala Trp Thr Lys Phe Asp
            130                 135                 140
Phe Pro Gly Arg Gly Asn Thr Tyr Ser Asp Phe Lys Trp Arg Trp Tyr
145                 150                 155                 160
His Phe Asp Gly Val Asp Trp Asp Gln Ser Arg Gln Phe Gln Asn Arg
            165                 170                 175
Ile Tyr Lys Phe Arg Gly Asp Gly Lys Ala Trp Asp Trp Glu Val Asp
            180                 185                 190
Ser Glu Asn Gly Asn Tyr Asp Tyr Leu Met Tyr Ala Asp Val Asp Met
            195                 200                 205
```

Asp His Pro Glu Val Val Asn Glu Leu Arg Arg Trp Gly Glu Trp Tyr
210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
                245                 250                 255

Thr Gly Lys Glu Met Phe Ala Val Ala Glu Phe Trp Lys Asn Asp Leu
            260                 265                 270

Gly Ala Leu Glu Asn Tyr Leu Asn Lys Thr Asn Trp Asn His Ser Val
        275                 280                 285

Phe Asp Val Pro Leu His Tyr Asn Leu Tyr Asn Ala Ser Asn Ser Gly
290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
        355                 360                 365

Gly Asp Tyr Tyr Gly Ile Pro Thr His Ser Val Pro Ala Met Lys Ala
370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                405                 410                 415

Gly Asn Thr Thr His Pro Asn Ser Gly Leu Ala Thr Ile Met Ser Asp
            420                 425                 430

Gly Pro Gly Gly Glu Lys Trp Met Tyr Val Gly Gln Asn Lys Ala Gly
        435                 440                 445

Gln Val Trp His Asp Ile Thr Gly Asn Lys Pro Gly Thr Val Thr Ile
450                 455                 460

Asn Ala Asp Gly Trp Ala Asn Phe Ser Val Asn Gly Gly Ser Val Ser
465                 470                 475                 480

Ile Trp Val Lys Arg
                485

<210> SEQ ID NO 8
<211> LENGTH: 485
<212> TYPE: PRT
<213> ORGANISM: Bacillus

<400> SEQUENCE: 8

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
                20                  25                  30

Asn Leu Lys Ser Lys Gly Ile Thr Ala Val Trp Ile Pro Pro Ala Trp
            35                  40                  45

Lys Gly Ala Ser Gln Asn Asp Val Gly Tyr Gly Ala Tyr Asp Leu Tyr
        50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

```
Ile Gln Val Tyr Gly Asp Val Val Met Asn His Lys Gly Gly Ala Asp
                100                 105                 110

Ala Thr Glu Met Val Arg Ala Val Glu Val Asn Pro Asn Asn Arg Asn
            115                 120                 125

Gln Glu Val Thr Gly Glu Tyr Thr Ile Glu Ala Trp Thr Arg Phe Asp
        130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Arg Ser
    370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Ser Lys Trp Met Phe Val Gly Arg Asn Lys Ala Gly
        435                 440                 445

Gln Val Trp Ser Asp Ile Thr Gly Asn Arg Thr Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 9
<211> LENGTH: 586
<212> TYPE: PRT
<213> ORGANISM: Bacillus
```

<400> SEQUENCE: 9

Gly Ser Val Pro Val Asn Gly Thr Met Met Gln Tyr Phe Glu Trp Tyr
1               5                   10                  15

Leu Pro Asp Asp Gly Thr Leu Trp Thr Lys Val Ala Asn Asn Ala Gln
            20                  25                  30

Ser Leu Ala Asn Leu Gly Ile Thr Ala Leu Trp Leu Pro Pro Ala Tyr
        35                  40                  45

Lys Gly Thr Ser Ser Asp Val Gly Tyr Gly Val Tyr Asp Leu Tyr
    50                  55                  60

Asp Leu Gly Glu Phe Asn Gln Lys Gly Thr Val Arg Thr Lys Tyr Gly
65                  70                  75                  80

Thr Lys Thr Gln Tyr Ile Gln Ala Ile Gln Ala Ala His Thr Ala Gly
                85                  90                  95

Met Gln Val Tyr Ala Asp Val Val Phe Asn His Lys Ala Gly Ala Asp
            100                 105                 110

Gly Thr Glu Leu Val Asp Ala Val Glu Val Asn Pro Ser Asp Arg Asn
        115                 120                 125

Gln Glu Ile Ser Gly Thr Tyr Gln Ile Gln Ala Trp Thr Lys Phe Asp
130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Thr Gly Lys Ala Trp Asp Trp Glu Val Asp Thr
            180                 185                 190

Glu Asn Gly Asn Tyr Asp Tyr Leu Met Tyr Ala Asp Leu Asp Met Asp
        195                 200                 205

His Pro Glu Val Val Ser Glu Leu Lys Asn Trp Gly Lys Trp Tyr Val
210                 215                 220

Ile Thr Thr Asn Ile Asp Gly Phe Arg Leu Asp Ala Val Lys His Ile
225                 230                 235                 240

Lys Tyr Ser Phe Phe Pro Asp Trp Leu Ser Tyr Leu Arg Thr Gln Thr
                245                 250                 255

Gln Lys Pro Leu Phe Ala Val Gly Glu Phe Trp Ser Tyr Asp Ile Asn
            260                 265                 270

Lys Leu His Asn Tyr Ile Thr Lys Thr Asn Gly Ser Met Ser Leu Phe
        275                 280                 285

Asp Ala Pro Leu His Asn Asn Phe Tyr Ile Ala Ser Lys Ser Gly Gly
290                 295                 300

Tyr Phe Asp Met Arg Thr Leu Leu Asn Asn Thr Leu Met Lys Glu Gln
305                 310                 315                 320

Pro Thr Leu Ser Val Thr Leu Val Asp Asn His Asp Thr Glu Pro Gly
                325                 330                 335

Gln Ser Leu Gln Ser Trp Val Glu Pro Trp Phe Lys Pro Leu Ala Tyr
            340                 345                 350

Ala Phe Ile Leu Thr Arg Gln Glu Gly Tyr Pro Cys Val Phe Tyr Gly
        355                 360                 365

Asp Tyr Tyr Gly Ile Pro Lys Tyr Asn Ile Pro Ala Leu Lys Ser Lys
370                 375                 380

Leu Asp Pro Leu Leu Ile Ala Arg Arg Asp Tyr Ala Tyr Gly Thr Gln
385                 390                 395                 400

His Asp Tyr Ile Asp Asn Ala Asp Ile Ile Gly Trp Thr Arg Glu Gly
                405                 410                 415

```
Val Ala Glu Lys Ala Asn Ser Gly Leu Ala Ala Leu Ile Thr Asp Gly
            420                 425                 430

Pro Gly Gly Ser Lys Trp Met Tyr Val Gly Lys Gln His Ala Gly Lys
            435                 440                 445

Thr Phe Tyr Asp Leu Thr Gly Asn Arg Ser Asp Val Thr Ile Asn
450                 455                 460

Ala Asp Gly Trp Gly Glu Phe Lys Val Asn Gly Gly Ser Val Ser Ile
465                 470                 475                 480

Trp Val Pro Lys Thr Ser Thr Ser Gln Ile Thr Phe Thr Val Asn
                485                 490                 495

Asn Ala Thr Thr Val Trp Gly Gln Asn Val Tyr Val Val Gly Asn Ile
            500                 505                 510

Ser Gln Leu Gly Asn Trp Asp Pro Val Asn Ala Val Gln Met Thr Pro
            515                 520                 525

Ser Ser Tyr Pro Thr Trp Val Val Thr Val Pro Leu Pro Gln Ser Gln
            530                 535                 540

Asn Ile Gln Phe Lys Phe Ile Lys Lys Asp Gly Ser Gly Asn Val Ile
545                 550                 555                 560

Trp Glu Asn Ile Ser Asn Arg Thr Tyr Thr Val Pro Thr Ala Ala Ser
                565                 570                 575

Gly Ala Tyr Thr Ala Asn Trp Asn Val Pro
            580                 585

<210> SEQ ID NO 10
<211> LENGTH: 583
<212> TYPE: PRT
<213> ORGANISM: Bacillus

<400> SEQUENCE: 10

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
                20                  25                  30

Asn Leu Ser Ser Leu Gly Ile Thr Ala Leu Trp Leu Pro Pro Ala Tyr
            35                  40                  45

Lys Gly Thr Ser Gln Ser Asp Val Gly Tyr Gly Val Tyr Asp Leu Tyr
50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Lys Ala Ala Gly
                85                  90                  95

Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
            115                 120                 125

Gln Glu Thr Ser Gly Thr Tyr Gln Ile Gln Ala Trp Thr Lys Phe Asp
            130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Ser Thr Gly Lys Ala Trp Asp Trp Glu Val Asp Thr
            180                 185                 190

Glu Asn Gly Asn Tyr Asp Tyr Leu Met Phe Ala Asp Leu Asp Met Asp
            195                 200                 205
```

```
His Pro Glu Val Val Thr Glu Leu Lys Asn Trp Gly Thr Trp Tyr Val
    210                 215                 220

Asn Thr Thr Asn Ile Asp Gly Phe Arg Leu Asp Ala Val Lys His Ile
225                 230                 235                 240

Lys Tyr Ser Phe Phe Pro Asp Trp Leu Thr Tyr Val Arg Asn Gln Thr
                245                 250                 255

Gly Lys Asn Leu Phe Ala Val Gly Glu Phe Trp Ser Tyr Asp Val Asn
            260                 265                 270

Lys Leu His Asn Tyr Ile Thr Lys Thr Asn Gly Ser Met Ser Leu Phe
        275                 280                 285

Asp Ala Pro Leu His Asn Asn Phe Tyr Thr Ala Ser Lys Ser Ser Gly
    290                 295                 300

Tyr Phe Asp Met Arg Tyr Leu Leu Asn Asn Thr Leu Met Lys Asp Gln
305                 310                 315                 320

Pro Ser Leu Ala Val Thr Leu Val Asp Asn His Asp Thr Gln Pro Gly
                325                 330                 335

Gln Ser Leu Gln Ser Trp Val Glu Pro Trp Phe Lys Pro Leu Ala Tyr
            340                 345                 350

Ala Phe Ile Leu Thr Arg Gln Glu Gly Tyr Pro Cys Val Phe Tyr Gly
        355                 360                 365

Asp Tyr Tyr Gly Ile Pro Lys Tyr Asn Ile Pro Gly Leu Lys Ser Lys
    370                 375                 380

Ile Asp Pro Leu Leu Ile Ala Arg Arg Asp Tyr Ala Tyr Gly Thr Gln
385                 390                 395                 400

Arg Asp Tyr Ile Asp His Gln Asp Ile Ile Gly Trp Thr Arg Glu Gly
                405                 410                 415

Ile Asp Thr Lys Pro Asn Ser Gly Leu Ala Ala Leu Ile Thr Asp Gly
            420                 425                 430

Pro Gly Gly Ser Lys Trp Met Tyr Val Gly Lys Lys His Ala Gly Lys
        435                 440                 445

Val Phe Tyr Asp Leu Thr Gly Asn Arg Ser Asp Thr Val Thr Ile Asn
    450                 455                 460

Ala Asp Gly Trp Gly Glu Phe Lys Val Asn Gly Gly Ser Val Ser Ile
465                 470                 475                 480

Trp Val Ala Lys Thr Ser Asn Val Thr Phe Thr Val Asn Asn Ala Thr
                485                 490                 495

Thr Thr Ser Gly Gln Asn Val Tyr Val Val Ala Asn Ile Pro Glu Leu
            500                 505                 510

Gly Asn Trp Asn Thr Ala Asn Ala Ile Lys Met Asn Pro Ser Ser Tyr
        515                 520                 525

Pro Thr Trp Lys Ala Thr Ile Ala Leu Pro Gln Gly Lys Ala Ile Glu
    530                 535                 540

Phe Lys Phe Ile Lys Lys Asp Gln Ala Gly Asn Val Ile Trp Glu Ser
545                 550                 555                 560

Thr Ser Asn Arg Thr Tyr Thr Val Pro Phe Ser Ser Thr Gly Ser Tyr
                565                 570                 575

Thr Ala Ser Trp Asn Val Pro
            580

<210> SEQ ID NO 11
<211> LENGTH: 485
<212> TYPE: PRT
<213> ORGANISM: Bacillus

<400> SEQUENCE: 11
```

```
His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ala
            20                  25                  30

Asn Leu Lys Ser Lys Gly Ile Thr Ala Val Trp Ile Pro Pro Ala Trp
            35                  40                  45

Lys Gly Thr Ser Gln Asn Asp Val Gly Tyr Gly Ala Tyr Asp Leu Tyr
        50                  55                  60

Asp Leu Gly Glu Phe Asn Gln Lys Gly Thr Val Arg Thr Lys Tyr Gly
65                  70                  75                  80

Thr Arg Ser Gln Leu Gln Gly Ala Val Thr Ser Leu Lys Asn Asn Gly
            85                  90                  95

Ile Gln Val Tyr Gly Asp Val Val Met Asn His Lys Gly Gly Ala Asp
            100                 105                 110

Gly Thr Glu Met Val Asn Ala Val Glu Val Asn Arg Ser Asn Arg Asn
            115                 120                 125

Gln Glu Ile Ser Gly Glu Tyr Thr Ile Glu Ala Trp Thr Lys Phe Asp
        130                 135                 140

Phe Pro Gly Arg Gly Asn Thr His Ser Asn Phe Lys Trp Arg Trp Tyr
145                 150                 155                 160

His Phe Asp Gly Thr Asp Trp Asp Gln Ser Arg Gln Leu Gln Asn Lys
            165                 170                 175

Ile Tyr Lys Phe Arg Gly Thr Gly Lys Ala Trp Asp Trp Glu Val Asp
            180                 185                 190

Ile Glu Asn Gly Asn Tyr Asp Tyr Leu Met Tyr Ala Asp Ile Asp Met
            195                 200                 205

Asp His Pro Glu Val Ile Asn Glu Leu Arg Asn Trp Gly Val Trp Tyr
        210                 215                 220

Thr Asn Thr Leu Asn Leu Asp Gly Phe Arg Ile Asp Ala Val Lys His
225                 230                 235                 240

Ile Lys Tyr Ser Tyr Thr Arg Asp Trp Leu Thr His Val Arg Asn Thr
            245                 250                 255

Thr Gly Lys Pro Met Phe Ala Val Ala Glu Phe Trp Lys Asn Asp Leu
            260                 265                 270

Ala Ala Ile Glu Asn Tyr Leu Asn Lys Thr Ser Trp Asn His Ser Val
            275                 280                 285

Phe Asp Val Pro Leu His Tyr Asn Leu Tyr Asn Ala Ser Asn Ser Gly
        290                 295                 300

Gly Tyr Phe Asp Met Arg Asn Ile Leu Asn Gly Ser Val Val Gln Lys
305                 310                 315                 320

His Pro Ile His Ala Val Thr Phe Val Asp Asn His Asp Ser Gln Pro
            325                 330                 335

Gly Glu Ala Leu Glu Ser Phe Val Gln Ser Trp Phe Lys Pro Leu Ala
            340                 345                 350

Tyr Ala Leu Ile Leu Thr Arg Glu Gln Gly Tyr Pro Ser Val Phe Tyr
            355                 360                 365

Gly Asp Tyr Tyr Gly Ile Pro Thr His Gly Val Pro Ser Met Lys Ser
        370                 375                 380

Lys Ile Asp Pro Leu Leu Gln Ala Arg Gln Thr Tyr Ala Tyr Gly Thr
385                 390                 395                 400

Gln His Asp Tyr Phe Asp His His Asp Ile Ile Gly Trp Thr Arg Glu
            405                 410                 415

Gly Asp Ser Ser His Pro Asn Ser Gly Leu Ala Thr Ile Met Ser Asp
```

-continued

```
                420             425             430
Gly Pro Gly Gly Asn Lys Trp Met Tyr Val Gly Lys His Lys Ala Gly
            435                 440                 445
Gln Val Trp Arg Asp Ile Thr Gly Asn Arg Ser Gly Thr Val Thr Ile
        450                 455                 460
Asn Ala Asp Gly Trp Gly Asn Phe Thr Val Asn Gly Gly Ala Val Ser
465                 470                 475                 480
Val Trp Val Lys Gln
                485

<210> SEQ ID NO 12
<211> LENGTH: 485
<212> TYPE: PRT
<213> ORGANISM: Bacillus

<400> SEQUENCE: 12

His His Asn Gly Thr Asn Gly Thr Met Met Gln Tyr Phe Glu Trp Tyr
1               5                   10                  15
Leu Pro Asn Asp Gly Asn His Trp Asn Arg Leu Arg Ser Asp Ala Ser
            20                  25                  30
Asn Leu Lys Asp Lys Gly Ile Thr Ala Val Trp Ile Pro Pro Ala Trp
        35                  40                  45
Lys Gly Ala Ser Gln Asn Asp Val Gly Tyr Gly Ala Tyr Asp Leu Tyr
    50                  55                  60
Asp Leu Gly Glu Phe Asn Gln Lys Gly Thr Val Arg Thr Lys Tyr Gly
65                  70                  75                  80
Thr Arg Asn Gln Leu Gln Ala Ala Val Thr Ala Leu Lys Ser Asn Gly
                85                  90                  95
Ile Gln Val Tyr Gly Asp Val Val Met Asn His Lys Gly Gly Ala Asp
            100                 105                 110
Ala Thr Glu Trp Val Arg Ala Val Glu Val Asn Pro Ser Asn Arg Asn
        115                 120                 125
Gln Glu Val Ser Gly Asp Tyr Thr Ile Glu Ala Trp Thr Lys Phe Asp
    130                 135                 140
Phe Pro Gly Arg Gly Asn Thr His Ser Asn Phe Lys Trp Arg Trp Tyr
145                 150                 155                 160
His Phe Asp Gly Val Asp Trp Asp Gln Ser Arg Gln Leu Gln Asn Arg
                165                 170                 175
Ile Tyr Lys Phe Arg Gly Asp Gly Lys Gly Trp Asp Trp Glu Val Asp
            180                 185                 190
Thr Glu Asn Gly Asn Tyr Asp Tyr Leu Met Tyr Ala Asp Ile Asp Met
        195                 200                 205
Asp His Pro Glu Val Val Asn Glu Leu Arg Asn Trp Gly Val Trp Tyr
    210                 215                 220
Thr Asn Thr Leu Gly Leu Asp Gly Phe Arg Ile Gly Ala Val Lys His
225                 230                 235                 240
Ile Lys Tyr Ser Phe Thr Arg Asp Trp Leu Thr His Val Arg Asn Thr
                245                 250                 255
Thr Gly Lys Asn Met Phe Ala Val Ala Glu Phe Trp Lys Asn Asp Ile
            260                 265                 270
Gly Ala Ile Glu Asn Tyr Leu Ser Lys Thr Asn Trp Asn His Ser Val
        275                 280                 285
Phe Asp Val Pro Leu His Tyr Asn Leu Tyr Asn Ala Ser Arg Ser Gly
    290                 295                 300
Gly Asn Tyr Asp Met Arg Gln Ile Phe Asn Gly Thr Val Val Gln Arg
```

```
                305                 310                 315                 320
His Pro Thr His Ala Val Thr Phe Val Asp Asn His Asp Ser Gln Pro
                    325                 330                 335

Glu Glu Ala Leu Glu Ser Phe Val Glu Glu Trp Phe Lys Pro Leu Ala
                    340                 345                 350

Cys Ala Leu Thr Leu Thr Arg Asp Gln Gly Tyr Pro Ser Val Phe Tyr
                    355                 360                 365

Gly Asp Tyr Tyr Gly Ile Pro Thr His Gly Val Pro Ala Met Lys Ser
                370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Met Ile Gly Trp Thr Arg Glu
                    405                 410                 415

Gly Asn Thr Ala His Pro Asn Ser Gly Leu Ala Thr Ile Met Ser Asp
                    420                 425                 430

Gly Pro Gly Gly Asn Lys Trp Met Tyr Val Gly Arg Asn Lys Ala Gly
                435                 440                 445

Gln Val Trp Arg Asp Ile Thr Gly Asn Arg Ser Gly Thr Val Thr Ile
                450                 455                 460

Asn Ala Asp Gly Trp Gly Asn Phe Ser Val Asn Gly Gly Ser Val Ser
465                 470                 475                 480

Ile Trp Val Asn Asn
                485

<210> SEQ ID NO 13
<211> LENGTH: 492
<212> TYPE: PRT
<213> ORGANISM: Bacillus circulans

<400> SEQUENCE: 13

Lys Arg Asn His Thr Met Met Gln Phe Phe Glu Trp His Leu Ala Ala
1               5                   10                  15

Asp Gly Asp His Trp Lys Arg Leu Ala Glu Met Ala Pro Glu Leu Lys
                20                  25                  30

Ala Lys Gly Ile Asp Thr Val Trp Val Pro Pro Val Thr Lys Ala Val
                35                  40                  45

Ser Ala Glu Asp Thr Gly Tyr Gly Val Tyr Asp Leu Tyr Asp Leu Gly
            50                  55                  60

Glu Phe Asp Gln Lys Gly Thr Val Arg Thr Lys Tyr Gly Thr Lys Gln
65                  70                  75                  80

Glu Leu Ile Glu Ala Ile Ala Glu Cys Gln Lys Asn Gly Ile Ala Val
                85                  90                  95

Tyr Val Asp Leu Val Met Asn His Lys Ala Gly Ala Asp Glu Thr Glu
                100                 105                 110

Val Phe Lys Val Ile Glu Val Asp Pro Asn Asp Arg Thr Lys Glu Ile
                115                 120                 125

Ser Glu Pro Phe Glu Ile Glu Gly Trp Thr Lys Phe Thr Phe Pro Gly
            130                 135                 140

Arg Gly Asp Gln Tyr Ser Ser Phe Lys Trp Asn Ser Glu His Phe Asn
145                 150                 155                 160

Gly Thr Asp Phe Asp Ala Arg Glu Glu Arg Thr Gly Val Phe Arg Ile
                165                 170                 175

Ala Gly Glu Asn Lys Lys Trp Asn Glu Asn Val Asp Asp Glu Phe Gly
                180                 185                 190

Asn Tyr Asp Tyr Leu Met Phe Ala Asn Ile Asp Tyr Asn His Pro Asp
```

```
                195                 200                 205
Val Arg Arg Glu Met Ile Asp Trp Gly Lys Trp Leu Ile Asp Thr Leu
210                 215                 220

Gln Cys Gly Gly Phe Arg Leu Asp Ala Ile Lys His Ile Asn His Glu
225                 230                 235                 240

Phe Ile Lys Glu Phe Ala Ala Glu Met Ile Arg Lys Arg Gly Gln Asp
                245                 250                 255

Phe Tyr Ile Val Gly Glu Phe Trp Asn Ser Asn Leu Asp Ala Cys Arg
                260                 265                 270

Glu Phe Leu Asp Thr Val Asp Tyr Gln Ile Asp Leu Phe Asp Val Ser
                275                 280                 285

Leu His Tyr Lys Leu His Glu Ala Ser Leu Lys Gly Arg Asp Phe Asp
                290                 295                 300

Leu Ser Lys Ile Phe Asp Asp Thr Leu Val Gln Thr His Pro Thr His
305                 310                 315                 320

Ala Val Thr Phe Val Asp Asn His Asp Ser Gln Pro His Glu Ala Leu
                325                 330                 335

Glu Ser Trp Ile Gly Asp Trp Phe Lys Pro Ser Ala Tyr Ala Leu Thr
                340                 345                 350

Leu Leu Arg Arg Asp Gly Tyr Pro Val Val Phe Tyr Gly Asp Tyr Tyr
                355                 360                 365

Gly Ile Gly Gly Pro Glu Pro Val Asp Gly Lys Lys Glu Ile Leu Asp
                370                 375                 380

Ile Leu Leu Ser Ala Arg Cys Asn Lys Ala Tyr Gly Glu Gln Glu Asp
385                 390                 395                 400

Tyr Phe Asp His Ala Asn Thr Ile Gly Trp Val Arg Arg Gly Val Glu
                405                 410                 415

Glu Ile Glu Gly Ser Gly Cys Ala Val Val Ile Ser Asn Gly Asp Asp
                420                 425                 430

Gly Glu Lys Arg Met Phe Ile Gly Glu His Arg Ala Gly Glu Val Trp
                435                 440                 445

Val Asp Leu Thr Lys Ser Cys Asp Asp Gln Ile Thr Ile Glu Glu Asp
450                 455                 460

Gly Trp Ala Thr Phe His Val Cys Gly Gly Val Ser Val Trp Ala
465                 470                 475                 480

Leu Pro Glu Gln Asn Glu Asp Cys Ala Asp Ala Glu
                485                 490

<210> SEQ ID NO 14
<211> LENGTH: 480
<212> TYPE: PRT
<213> ORGANISM: Bacillus

<400> SEQUENCE: 14

Asp Gly Leu Asn Gly Thr Met Met Gln Tyr Tyr Glu Trp His Leu Glu
1               5                   10                  15

Asn Asp Gly Gln His Trp Asn Arg Leu His Asp Ala Glu Ala Leu
                20                  25                  30

Ser Asn Ala Gly Ile Thr Ala Ile Trp Ile Pro Pro Ala Tyr Lys Gly
                35                  40                  45

Asn Ser Gln Ala Asp Val Gly Tyr Gly Ala Tyr Asp Leu Tyr Asp Leu
                50                  55                  60

Gly Glu Phe Asn Gln Lys Gly Thr Val Arg Thr Lys Tyr Gly Thr Lys
65                  70                  75                  80

Ala Gln Leu Glu Arg Ala Ile Gly Ser Leu Lys Ser Asn Asp Ile Asn
```

```
                     85                  90                  95
Val Tyr Gly Asp Val Val Met Asn His Lys Leu Gly Ala Asp Phe Thr
                100                 105                 110

Glu Ala Val Gln Ala Val Gln Val Asn Pro Ser Asn Arg Trp Gln Asp
            115                 120                 125

Ile Ser Gly Val Tyr Thr Ile Asp Ala Trp Thr Gly Phe Asp Phe Pro
        130                 135                 140

Gly Arg Asn Asn Ala Tyr Ser Asp Phe Lys Trp Arg Trp Phe His Phe
145                 150                 155                 160

Asn Gly Val Asp Trp Asp Gln Arg Tyr Gln Glu Asn His Leu Phe Arg
                165                 170                 175

Phe Ala Asn Thr Asn Trp Asn Trp Arg Val Asp Glu Glu Asn Gly Asn
            180                 185                 190

Tyr Asp Tyr Leu Leu Gly Ser Asn Ile Asp Phe Ser His Pro Glu Val
        195                 200                 205

Gln Glu Glu Leu Lys Asp Trp Gly Ser Trp Phe Thr Asp Glu Leu Asp
210                 215                 220

Leu Asp Gly Tyr Arg Leu Asp Ala Ile Lys His Ile Pro Phe Trp Tyr
225                 230                 235                 240

Thr Ser Asp Trp Val Arg His Gln Arg Ser Glu Ala Asp Gln Asp Leu
                245                 250                 255

Phe Val Val Gly Glu Tyr Trp Lys Asp Val Gly Ala Leu Glu Phe
            260                 265                 270

Tyr Leu Asp Glu Met Asn Trp Glu Met Ser Leu Phe Asp Val Pro Leu
        275                 280                 285

Asn Tyr Asn Phe Tyr Arg Ala Ser Lys Gln Gly Gly Ser Tyr Asp Met
290                 295                 300

Arg Asn Ile Leu Arg Gly Ser Leu Val Glu Ala His Pro Ile His Ala
305                 310                 315                 320

Val Thr Phe Val Asp Asn His Asp Thr Gln Pro Gly Glu Ser Leu Glu
                325                 330                 335

Ser Trp Val Ala Asp Trp Phe Lys Pro Leu Ala Tyr Ala Thr Ile Leu
            340                 345                 350

Thr Arg Glu Gly Gly Tyr Pro Asn Val Phe Tyr Gly Asp Tyr Tyr Gly
        355                 360                 365

Ile Pro Asn Asp Asn Ile Ser Ala Lys Lys Asp Met Ile Asp Glu Leu
370                 375                 380

Leu Asp Ala Arg Gln Asn Tyr Ala Tyr Gly Thr Gln His Asp Tyr Phe
385                 390                 395                 400

Asp His Trp Asp Ile Val Gly Trp Thr Arg Glu Gly Thr Ser Ser Arg
                405                 410                 415

Pro Asn Ser Gly Leu Ala Thr Ile Met Ser Asn Gly Pro Gly Gly Ser
            420                 425                 430

Lys Trp Met Tyr Val Gly Gln Gln His Ala Gly Gln Thr Trp Thr Asp
        435                 440                 445

Leu Thr Gly Asn His Ala Ala Ser Val Thr Ile Asn Gly Asp Gly Trp
450                 455                 460

Gly Glu Phe Phe Thr Asn Gly Gly Ser Val Ser Val Tyr Val Asn Gln
465                 470                 475                 480

<210> SEQ ID NO 15
<211> LENGTH: 480
<212> TYPE: PRT
<213> ORGANISM: Bacillus
```

```
<400> SEQUENCE: 15

Asp Gly Leu Asn Gly Thr Met Met Gln Tyr Tyr Glu Trp His Leu Glu
1               5                   10                  15

Asn Asp Gly Gln His Trp Asn Arg Leu His Asp Ala Ala Ala Ala Leu
            20                  25                  30

Ser Asp Ala Gly Ile Thr Ala Ile Trp Ile Pro Pro Ala Tyr Lys Gly
        35                  40                  45

Asn Ser Gln Ala Asp Val Gly Tyr Gly Ala Tyr Asp Leu Tyr Asp Leu
    50                  55                  60

Gly Glu Phe Asn Gln Lys Gly Thr Val Arg Thr Lys Tyr Gly Thr Lys
65              70                  75                  80

Ala Gln Leu Glu Arg Ala Ile Gly Ser Leu Lys Ser Asn Asp Ile Asn
                85                  90                  95

Val Tyr Gly Asp Val Val Met Asn His Lys Met Gly Ala Asp Phe Thr
            100                 105                 110

Glu Ala Val Gln Ala Val Gln Val Asn Pro Thr Asn Arg Trp Gln Asp
            115                 120                 125

Ile Ser Gly Ala Tyr Thr Ile Asp Ala Trp Thr Gly Phe Asp Phe Ser
130                 135                 140

Gly Arg Asn Asn Ala Tyr Ser Asp Phe Lys Trp Arg Trp Phe His Phe
145                 150                 155                 160

Asn Gly Val Asp Trp Asp Gln Arg Tyr Gln Glu Asn His Ile Phe Arg
            165                 170                 175

Phe Ala Asn Thr Asn Trp Asn Trp Arg Val Asp Glu Glu Asn Gly Asn
            180                 185                 190

Tyr Asp Tyr Leu Leu Gly Ser Asn Ile Asp Phe Ser His Pro Glu Val
            195                 200                 205

Gln Asp Glu Leu Lys Asp Trp Gly Ser Trp Phe Thr Asp Glu Leu Asp
210                 215                 220

Leu Asp Gly Tyr Arg Leu Asp Ala Ile Lys His Ile Pro Phe Trp Tyr
225                 230                 235                 240

Thr Ser Asp Trp Val Arg His Gln Arg Asn Glu Ala Asp Gln Asp Leu
            245                 250                 255

Phe Val Val Gly Glu Tyr Trp Lys Asp Asp Val Gly Ala Leu Glu Phe
            260                 265                 270

Tyr Leu Asp Glu Met Asn Trp Glu Met Ser Leu Phe Asp Val Pro Leu
            275                 280                 285

Asn Tyr Asn Phe Tyr Arg Ala Ser Gln Gln Gly Gly Ser Tyr Asp Met
            290                 295                 300

Arg Asn Ile Leu Arg Gly Ser Leu Val Glu Ala His Pro Met His Ala
305                 310                 315                 320

Val Thr Phe Val Asp Asn His Asp Thr Gln Pro Gly Glu Ser Leu Glu
            325                 330                 335

Ser Trp Val Ala Asp Trp Phe Lys Pro Leu Ala Tyr Ala Thr Ile Leu
            340                 345                 350

Thr Arg Glu Gly Gly Tyr Pro Asn Val Phe Tyr Gly Asp Tyr Tyr Gly
            355                 360                 365

Ile Pro Asn Asp Asn Ile Ser Ala Lys Lys Asp Met Ile Asp Glu Leu
            370                 375                 380

Leu Asp Ala Arg Gln Asn Tyr Ala Tyr Gly Thr Gln His Asp Tyr Phe
385                 390                 395                 400

Asp His Trp Asp Val Val Gly Trp Thr Arg Glu Gly Ser Ser Ser Arg
            405                 410                 415
```

-continued

```
Pro Asn Ser Gly Leu Ala Thr Ile Met Ser Asn Gly Pro Gly Gly Ser
            420                 425                 430

Lys Trp Met Tyr Val Gly Arg Gln Asn Ala Gly Gln Thr Trp Thr Asp
            435                 440                 445

Leu Thr Gly Asn Asn Gly Ala Ser Val Thr Ile Asn Gly Asp Gly Trp
    450                 455                 460

Gly Glu Phe Phe Thr Asn Gly Gly Ser Val Ser Val Tyr Val Asn Gln
465                 470                 475                 480

<210> SEQ ID NO 16
<211> LENGTH: 435
<212> TYPE: PRT
<213> ORGANISM: Pyrococcus woesei

<400> SEQUENCE: 16

Ala Lys Tyr Leu Glu Leu Glu Glu Gly Gly Val Ile Met Gln Ala Phe
1               5                   10                  15

Tyr Trp Asp Val Pro Gly Gly Gly Ile Trp Trp Asp His Ile Arg Ser
            20                  25                  30

Lys Ile Pro Glu Trp Tyr Glu Ala Gly Ile Ser Ala Ile Trp Leu Pro
        35                  40                  45

Pro Pro Ser Lys Gly Met Ser Gly Gly Tyr Ser Met Gly Tyr Asp Pro
    50                  55                  60

Tyr Asp Tyr Phe Asp Leu Gly Glu Tyr Tyr Gln Lys Gly Thr Val Glu
65                  70                  75                  80

Thr Arg Phe Gly Ser Lys Glu Glu Leu Val Arg Leu Ile Gln Thr Ala
                85                  90                  95

His Ala Tyr Gly Ile Lys Val Ile Ala Asp Val Val Ile Asn His Arg
            100                 105                 110

Ala Gly Gly Asp Leu Glu Trp Asn Pro Phe Val Gly Asp Tyr Thr Trp
        115                 120                 125

Thr Asp Phe Ser Lys Val Ala Ser Gly Lys Tyr Thr Ala Asn Tyr Leu
    130                 135                 140

Asp Phe His Pro Asn Glu Leu His Cys Cys Asp Glu Gly Thr Phe Gly
145                 150                 155                 160

Gly Phe Pro Asp Ile Cys His His Lys Glu Trp Asp Gln Tyr Trp Leu
                165                 170                 175

Trp Lys Ser Asn Glu Ser Tyr Ala Ala Tyr Leu Arg Ser Ile Gly Phe
            180                 185                 190

Asp Gly Trp Arg Phe Asp Tyr Val Lys Gly Tyr Gly Ala Trp Val Val
        195                 200                 205

Arg Asp Trp Leu Asn Trp Trp Gly Gly Trp Ala Val Gly Glu Tyr Trp
    210                 215                 220

Asp Thr Asn Val Asp Ala Leu Leu Ser Trp Ala Tyr Glu Ser Gly Ala
225                 230                 235                 240

Lys Val Phe Asp Phe Pro Leu Tyr Tyr Lys Met Asp Glu Ala Phe Asp
                245                 250                 255

Asn Asn Asn Ile Pro Ala Leu Val Tyr Ala Leu Gln Asn Gly Gln Thr
            260                 265                 270

Val Val Ser Arg Asp Pro Phe Lys Ala Val Thr Phe Val Ala Asn His
        275                 280                 285

Asp Thr Asp Ile Ile Trp Asn Lys Tyr Pro Ala Tyr Ala Phe Ile Leu
    290                 295                 300

Thr Tyr Glu Gly Gln Pro Val Ile Phe Tyr Arg Asp Phe Glu Glu Trp
305                 310                 315                 320
```

```
Leu Asn Lys Asp Lys Leu Ile Asn Leu Ile Trp Ile His Asp His Leu
            325                 330                 335

Ala Gly Gly Ser Thr Thr Ile Val Tyr Tyr Asp Asn Asp Glu Leu Ile
            340                 345                 350

Phe Val Arg Asn Gly Asp Ser Arg Arg Pro Gly Leu Ile Thr Tyr Ile
            355                 360                 365

Asn Leu Ser Pro Asn Trp Val Gly Arg Trp Val Tyr Val Pro Lys Phe
            370                 375                 380

Ala Gly Ala Cys Ile His Glu Tyr Thr Gly Asn Leu Gly Gly Trp Val
385                 390                 395                 400

Asp Lys Arg Val Asp Ser Ser Gly Trp Val Tyr Leu Glu Ala Pro Pro
            405                 410                 415

His Asp Pro Ala Asn Gly Tyr Tyr Gly Tyr Ser Val Trp Ser Tyr Cys
            420                 425                 430

Gly Val Gly
        435

<210> SEQ ID NO 17
<211> LENGTH: 484
<212> TYPE: PRT
<213> ORGANISM: Artificial sequence
<220> FEATURE:
<223> OTHER INFORMATION: Synthetic construct

<400> SEQUENCE: 17

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
            20                  25                  30

Asn Leu Arg Asn Arg Gly Ile Thr Ala Ile Trp Ile Pro Pro Ala Trp
            35                  40                  45

Lys Gly Thr Ser Gln Asn Asp Val Gly Tyr Gly Ala Tyr Asp Leu Tyr
        50                  55                  60

Asp Leu Gly Glu Phe Asn Gln Lys Gly Thr Val Arg Thr Lys Tyr Gly
65              70                  75                  80

Thr Arg Ser Gln Leu Glu Ser Ala Ile His Ala Leu Lys Asn Asn Gly
            85                  90                  95

Val Gln Val Tyr Gly Asp Val Val Met Asn His Lys Ala Gly Ala Asp
            100                 105                 110

Glu Thr Glu Val Phe Lys Val Ile Glu Val Asp Pro Asn Asp Arg Thr
            115                 120                 125

Lys Glu Ile Ser Glu Pro Phe Glu Ile Glu Gly Trp Thr Lys Phe Thr
        130                 135                 140

Phe Pro Gly Arg Gly Asp Gln Tyr Ser Ser Phe Lys Trp Asn Ser Glu
145                 150                 155                 160

His Phe Asn Gly Thr Asp Phe Asp Ala Lys Gly Glu Arg Thr Gly Val
            165                 170                 175

Phe Arg Ile Ala Gly Glu Asn Lys Lys Trp Asn Glu Asn Val Asp Asp
            180                 185                 190

Glu Phe Gly Asn Tyr Asp Tyr Leu Met Phe Ala Asn Ile Asp Tyr Asn
            195                 200                 205

His Pro Asp Val Arg Arg Glu Leu Arg Arg Trp Gly Glu Trp Tyr Thr
            210                 215                 220

Asn Thr Leu Asn Leu Asp Gly Phe Arg Ile Asp Ala Val Lys His Ile
225                 230                 235                 240

Lys Tyr Ser Phe Thr Arg Asp Trp Leu Thr His Val Arg Asn Ala Thr
```

```
                        245                 250                 255
Gly Lys Glu Met Phe Ala Val Ala Glu Phe Trp Lys Asn Asp Leu Gly
                260                 265                 270

Ala Leu Glu Asn Tyr Leu Asn Lys Thr Asn Trp Asn His Ser Val Phe
            275                 280                 285

Asp Val Pro Leu His Tyr Asn Leu Tyr Asn Ala Ser Asn Ser Gly Gly
        290                 295                 300

Asn Tyr Asp Met Ala Lys Leu Leu Asn Gly Thr Val Val Gln Lys His
305                 310                 315                 320

Pro Met His Ala Val Thr Phe Val Asp Asn His Asp Ser Gln Pro Gly
                325                 330                 335

Glu Ser Leu Glu Ser Phe Val Gln Glu Trp Phe Lys Pro Leu Ala Tyr
            340                 345                 350

Ala Leu Ile Leu Thr Arg Glu Gln Gly Tyr Pro Ser Val Phe Tyr Gly
        355                 360                 365

Asp Tyr Tyr Gly Ile Pro Thr His Ser Val Pro Ala Met Lys Ala Lys
    370                 375                 380

Ile Asp Pro Ile Leu Glu Ala Arg Gln Asn Phe Ala Tyr Gly Thr Gln
385                 390                 395                 400

His Asp Tyr Phe Asp His His Asn Ile Ile Gly Trp Thr Arg Glu Gly
                405                 410                 415

Asn Thr Thr His Pro Asn Ser Gly Leu Ala Thr Ile Met Ser Asp Gly
            420                 425                 430

Pro Gly Gly Glu Lys Trp Met Tyr Val Gly Gln Asn Lys Ala Gly Gln
        435                 440                 445

Val Trp His Asp Ile Thr Gly Asn Lys Pro Gly Thr Val Thr Ile Asn
    450                 455                 460

Ala Asp Gly Trp Ala Asn Phe Ser Val Asn Gly Gly Ser Val Ser Ile
465                 470                 475                 480

Trp Val Lys Arg

<210> SEQ ID NO 18
<211> LENGTH: 482
<212> TYPE: PRT
<213> ORGANISM: Artificial sequence
<220> FEATURE:
<223> OTHER INFORMATION: Synthetic construct

<400> SEQUENCE: 18

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
            20                  25                  30

Asn Leu Arg Asn Arg Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Ala Gly Ala Asp
            100                 105                 110

Glu Thr Glu Val Phe Lys Val Ile Glu Val Asp Pro Asn Asp Arg Thr
        115                 120                 125
```

Lys Glu Ile Ser Glu Pro Phe Glu Ile Glu Gly Trp Thr Lys Phe Thr
            130                 135                 140

Phe Pro Gly Arg Gly Asp Gln Tyr Ser Ser Phe Lys Trp Asn Ser Glu
145                 150                 155                 160

His Phe Asn Gly Thr Asp Phe Asp Ala Lys Gly Glu Arg Thr Gly Val
                165                 170                 175

Phe Arg Ile Ala Gly Lys Lys Trp Asn Trp Glu Val Asp Thr Glu Phe
            180                 185                 190

Gly Asn Tyr Asp Tyr Leu Met Phe Ala Asn Ile Asp Tyr Asn His Pro
        195                 200                 205

Asp Val Arg Arg Glu Leu Arg Arg Trp Gly Trp Tyr Thr Asn Thr
210                 215                 220

Leu Asn Leu Asp Gly Phe Arg Ile Asp Ala Val Lys His Ile Lys Tyr
225                 230                 235                 240

Ser Phe Thr Arg Asp Trp Leu Thr His Val Arg Asn Ala Thr Gly Lys
                245                 250                 255

Glu Met Phe Ala Val Ala Glu Phe Trp Lys Asn Asp Leu Gly Ala Leu
            260                 265                 270

Glu Asn Tyr Leu Asn Lys Thr Asn Trp Asn His Ser Val Phe Asp Val
        275                 280                 285

Pro Leu His Tyr Asn Leu Tyr Asn Ala Ser Asn Ser Gly Gly Asn Tyr
    290                 295                 300

Asp Met Ala Lys Leu Leu Asn Gly Thr Val Val Gln Lys His Pro Met
305                 310                 315                 320

His Ala Val Thr Phe Val Asp Asn His Asp Ser Gln Pro Gly Glu Ser
                325                 330                 335

Leu Glu Ser Phe Val Gln Glu Trp Phe Lys Pro Leu Ala Tyr Ala Leu
            340                 345                 350

Ile Leu Thr Arg Glu Gln Gly Tyr Pro Ser Val Phe Tyr Gly Asp Tyr
        355                 360                 365

Tyr Gly Ile Pro Thr His Ser Val Pro Ala Met Lys Ala Lys Ile Asp
    370                 375                 380

Pro Ile Leu Glu Ala Arg Gln Asn Phe Ala Tyr Gly Thr Gln His Asp
385                 390                 395                 400

Tyr Phe Asp His His Asn Ile Ile Gly Trp Thr Arg Glu Gly Asn Thr
                405                 410                 415

Thr His Pro Asn Ser Gly Leu Ala Thr Ile Met Ser Asp Gly Pro Gly
            420                 425                 430

Gly Glu Lys Trp Met Tyr Val Gly Gln Asn Lys Ala Gly Gln Val Trp
        435                 440                 445

His Asp Ile Thr Gly Asn Lys Pro Gly Thr Val Thr Ile Asn Ala Asp
    450                 455                 460

Gly Trp Ala Asn Phe Ser Val Asn Gly Gly Ser Val Ser Ile Trp Val
465                 470                 475                 480

Lys Arg

<210> SEQ ID NO 19
<211> LENGTH: 484
<212> TYPE: PRT
<213> ORGANISM: Artificial sequence
<220> FEATURE:
<223> OTHER INFORMATION: Synthetic construct

<400> SEQUENCE: 19

His His Asn Gly Thr Asn Gly Thr Met Met Gln Tyr Phe Glu Trp His
1               5                   10                  15

```
Leu Pro Asn Asp Gly Asn His Trp Asn Arg Leu Arg Asp Ala Ser
            20                  25                  30

Asn Leu Arg Asn Arg Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Ala Gly Ala Asp
            100                 105                 110

Glu Thr Glu Val Phe Lys Val Ile Glu Val Asp Pro Asn Asp Arg Thr
            115                 120                 125

Lys Glu Ile Ser Glu Pro Phe Glu Ile Glu Gly Trp Thr Lys Phe Thr
        130                 135                 140

Phe Pro Gly Arg Gly Asp Gln Tyr Ser Ser Phe Lys Trp Asn Ser Glu
145                 150                 155                 160

His Phe Asn Gly Thr Asp Phe Asp Ala Lys Gly Glu Arg Thr Gly Val
                165                 170                 175

Phe Arg Ile Ala Gly Glu Asn Lys Lys Trp Asn Glu Asn Val Asp Asp
            180                 185                 190

Glu Phe Gly Asn Tyr Asp Tyr Leu Met Phe Ala Asn Ile Asp Tyr Asn
        195                 200                 205

His Pro Asp Val Arg Asn Glu Leu Arg Arg Trp Gly Glu Trp Tyr Thr
    210                 215                 220

Asn Thr Leu Asn Leu Asp Gly Phe Arg Ile Asp Ala Val Lys His Ile
225                 230                 235                 240

Lys Tyr Ser Phe Thr Arg Asp Trp Leu Thr His Val Arg Asn Ala Thr
                245                 250                 255

Gly Lys Glu Met Phe Ala Val Ala Glu Phe Trp Lys Asn Asp Leu Gly
            260                 265                 270

Ala Leu Glu Asn Tyr Leu Asn Lys Thr Asn Trp Asn His Ser Val Phe
        275                 280                 285

Asp Val Pro Leu His Tyr Asn Leu Tyr Asn Ala Ser Asn Ser Gly Gly
    290                 295                 300

Asn Tyr Asp Met Ala Lys Leu Leu Asn Gly Thr Val Val Gln Lys His
305                 310                 315                 320

Pro Met His Ala Val Thr Phe Val Asp Asn His Asp Ser Gln Pro Gly
                325                 330                 335

Glu Ser Leu Glu Ser Phe Val Gln Glu Trp Phe Lys Pro Leu Ala Tyr
            340                 345                 350

Ala Leu Ile Leu Thr Arg Glu Gln Gly Tyr Pro Ser Val Phe Tyr Gly
        355                 360                 365

Asp Tyr Tyr Gly Ile Pro Thr His Ser Val Pro Ala Met Lys Ala Lys
    370                 375                 380

Ile Asp Pro Ile Leu Glu Ala Arg Gln Asn Phe Ala Tyr Gly Thr Gln
385                 390                 395                 400

His Asp Tyr Phe Asp His His Asn Ile Ile Gly Trp Thr Arg Glu Gly
                405                 410                 415

Asn Thr Thr His Pro Asn Ser Gly Leu Ala Thr Ile Met Ser Asp Gly
            420                 425                 430

Pro Gly Gly Glu Lys Trp Met Tyr Val Gly Gln Asn Lys Ala Gly Gln
```

```
                  435                 440                445
Val Trp His Asp Ile Thr Gly Asn Lys Pro Gly Thr Val Thr Ile Asn
450                     455                 460

Ala Asp Gly Trp Ala Asn Phe Ser Val Asn Gly Gly Ser Val Ser Ile
465                     470                 475                 480

Trp Val Lys Arg

<210> SEQ ID NO 20
<211> LENGTH: 482
<212> TYPE: PRT
<213> ORGANISM: Artificial sequence
<220> FEATURE:
<223> OTHER INFORMATION: Synthetic construct

<400> SEQUENCE: 20

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
                20                  25                  30

Asn Leu Arg Asn Arg Gly Ile Thr Ala Ile Trp Ile Pro Pro Ala Trp
            35                  40                  45

Lys Gly Thr Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Ala Gly Ala Asp
            100                 105                 110

Glu Thr Glu Val Phe Lys Val Ile Glu Val Asp Pro Asn Asp Arg Thr
        115                 120                 125

Lys Glu Ile Ser Glu Pro Phe Glu Ile Glu Gly Trp Thr Lys Phe Thr
130                 135                 140

Phe Pro Gly Arg Gly Asp Gln Tyr Ser Ser Phe Lys Trp Asn Ser Glu
145                 150                 155                 160

His Phe Asn Gly Thr Asp Phe Asp Ala Lys Gly Glu Arg Thr Gly Val
                165                 170                 175

Phe Arg Ile Ala Gly Lys Lys Trp Asn Trp Glu Val Asp Thr Glu Phe
            180                 185                 190

Gly Asn Tyr Asp Tyr Leu Met Phe Ala Asn Ile Asp Tyr Asn His Pro
        195                 200                 205

Asp Val Arg Asn Glu Leu Arg Arg Trp Gly Glu Trp Tyr Thr Asn Thr
210                 215                 220

Leu Asn Leu Asp Gly Phe Arg Ile Asp Ala Val Lys His Ile Lys Tyr
225                 230                 235                 240

Ser Phe Thr Arg Asp Trp Leu Thr His Val Arg Asn Ala Thr Gly Lys
                245                 250                 255

Glu Met Phe Ala Val Ala Glu Phe Trp Lys Asn Asp Leu Gly Ala Leu
            260                 265                 270

Glu Asn Tyr Leu Asn Lys Thr Asn Trp Asn His Ser Val Phe Asp Val
        275                 280                 285

Pro Leu His Tyr Asn Leu Tyr Asn Ala Ser Asn Ser Gly Gly Asn Tyr
290                 295                 300

Asp Met Ala Lys Leu Leu Asn Gly Thr Val Val Gln Lys His Pro Met
305                 310                 315                 320
```

```
His Ala Val Thr Phe Val Asp Asn His Asp Ser Gln Pro Gly Glu Ser
            325                 330                 335

Leu Glu Ser Phe Val Gln Glu Trp Phe Lys Pro Leu Ala Tyr Ala Leu
            340                 345                 350

Ile Leu Thr Arg Glu Gln Gly Tyr Pro Ser Val Phe Tyr Gly Asp Tyr
            355                 360                 365

Tyr Gly Ile Pro Thr His Ser Val Pro Ala Met Lys Ala Lys Ile Asp
    370                 375                 380

Pro Ile Leu Glu Ala Arg Gln Asn Phe Ala Tyr Gly Thr Gln His Asp
385                 390                 395                 400

Tyr Phe Asp His His Asn Ile Ile Gly Trp Thr Arg Glu Gly Asn Thr
                405                 410                 415

Thr His Pro Asn Ser Gly Leu Ala Thr Ile Met Ser Asp Gly Pro Gly
            420                 425                 430

Gly Glu Lys Trp Met Tyr Val Gly Gln Asn Lys Ala Gly Gln Val Trp
            435                 440                 445

His Asp Ile Thr Gly Asn Lys Pro Gly Thr Val Thr Ile Asn Ala Asp
            450                 455                 460

Gly Trp Ala Asn Phe Ser Val Asn Gly Gly Ser Val Ser Ile Trp Val
465                 470                 475                 480

Lys Arg

<210> SEQ ID NO 21
<211> LENGTH: 484
<212> TYPE: PRT
<213> ORGANISM: Artificial sequence
<220> FEATURE:
<223> OTHER INFORMATION: Synthetic construct

<400> SEQUENCE: 21

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
            20                  25                  30

Asn Leu Arg Asn Arg Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Ala Gly Ala Asp
            100                 105                 110

Glu Thr Glu Val Phe Lys Val Ile Glu Val Asp Pro Asn Asp Arg Thr
        115                 120                 125

Lys Glu Ile Ser Glu Pro Phe Glu Ile Glu Gly Trp Thr Lys Phe Thr
    130                 135                 140

Phe Pro Gly Arg Gly Asp Gln Tyr Ser Ser Phe Lys Trp Asn Ser Glu
145                 150                 155                 160

His Phe Asn Gly Thr Asp Phe Asp Ala Lys Gly Glu Arg Thr Gly Val
                165                 170                 175

Phe Arg Ile Ala Gly Glu Asn Lys Lys Trp Asn Glu Asn Val Asp Asp
            180                 185                 190

Glu Phe Gly Asn Tyr Asp Tyr Leu Met Phe Ala Asn Ile Asp Tyr Asn
        195                 200                 205
```

His Pro Asp Val Val Asn Glu Leu Arg Arg Trp Gly Glu Trp Tyr Thr
        210                 215                 220

Asn Thr Leu Asn Leu Asp Gly Phe Arg Ile Asp Ala Val Lys His Ile
225                 230                 235                 240

Lys Tyr Ser Phe Thr Arg Asp Trp Leu Thr His Val Arg Asn Ala Thr
                245                 250                 255

Gly Lys Glu Met Phe Ala Val Ala Glu Phe Trp Lys Asn Asp Leu Gly
            260                 265                 270

Ala Leu Glu Asn Tyr Leu Asn Lys Thr Asn Trp Asn His Ser Val Phe
        275                 280                 285

Asp Val Pro Leu His Tyr Asn Leu Tyr Asn Ala Ser Asn Ser Gly Gly
    290                 295                 300

Asn Tyr Asp Met Ala Lys Leu Leu Asn Gly Thr Val Val Gln Lys His
305                 310                 315                 320

Pro Met His Ala Val Thr Phe Val Asp Asn His Asp Ser Gln Pro Gly
                325                 330                 335

Glu Ser Leu Glu Ser Phe Val Gln Gly Trp Phe Lys Pro Leu Ala Tyr
            340                 345                 350

Ala Leu Ile Leu Thr Arg Glu Gln Gly Tyr Pro Ser Val Phe Tyr Gly
        355                 360                 365

Asp Tyr Tyr Gly Ile Pro Thr His Ser Val Pro Ala Met Lys Ala Lys
    370                 375                 380

Ile Asp Pro Ile Leu Glu Ala Arg Gln Asn Phe Ala Tyr Gly Thr Gln
385                 390                 395                 400

His Asp Tyr Phe Asp His His Asn Ile Ile Gly Trp Thr Arg Glu Gly
                405                 410                 415

Asn Thr Thr His Pro Asn Ser Gly Leu Ala Thr Ile Met Ser Asp Gly
            420                 425                 430

Pro Gly Gly Glu Lys Trp Met Tyr Val Gly Gln Asn Lys Ala Gly Gln
        435                 440                 445

Val Trp His Asp Ile Thr Gly Asn Lys Pro Gly Thr Val Thr Ile Asn
    450                 455                 460

Ala Asp Gly Trp Ala Asn Phe Ser Val Asn Gly Gly Ser Val Ser Ile
465                 470                 475                 480

Trp Val Lys Arg

<210> SEQ ID NO 22
<211> LENGTH: 482
<212> TYPE: PRT
<213> ORGANISM: Artificial sequence
<220> FEATURE:
<223> OTHER INFORMATION: Synthetic construct

<400> SEQUENCE: 22

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
                20                  25                  30

Asn Leu Arg Asn Arg Gly Ile Thr Ala Ile Trp Ile Pro Pro Ala Trp
            35                  40                  45

Lys Gly Thr Ser Gln Asn Asp Val Gly Tyr Gly Ala Tyr Asp Leu Tyr
        50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly

```
                85                  90                  95
Val Gln Val Tyr Gly Asp Val Val Met Asn His Lys Ala Gly Ala Asp
            100                 105                 110
Glu Thr Glu Val Phe Lys Val Ile Glu Val Asp Pro Asn Asp Arg Thr
        115                 120                 125
Lys Glu Ile Ser Glu Pro Phe Glu Ile Glu Gly Trp Thr Lys Phe Thr
    130                 135                 140
Phe Pro Gly Arg Gly Asp Gln Tyr Ser Ser Phe Lys Trp Asn Ser Glu
145                 150                 155                 160
His Phe Asn Gly Thr Asp Phe Asp Ala Lys Gly Glu Arg Thr Gly Val
                165                 170                 175
Phe Arg Ile Ala Gly Lys Lys Trp Asn Trp Glu Val Asp Thr Glu Phe
            180                 185                 190
Gly Asn Tyr Asp Tyr Leu Met Phe Ala Asn Ile Asp Tyr Asn His Pro
        195                 200                 205
Asp Val Val Asn Glu Leu Arg Arg Trp Gly Trp Tyr Thr Asn Thr
    210                 215                 220
Leu Asn Leu Asp Gly Phe Arg Ile Asp Ala Val Lys His Ile Lys Tyr
225                 230                 235                 240
Ser Phe Thr Arg Asp Trp Leu Thr His Val Arg Asn Ala Thr Gly Lys
                245                 250                 255
Glu Met Phe Ala Val Ala Glu Phe Trp Lys Asn Asp Leu Gly Ala Leu
            260                 265                 270
Glu Asn Tyr Leu Asn Lys Thr Asn Trp Asn His Ser Val Phe Asp Val
        275                 280                 285
Pro Leu His Tyr Asn Leu Tyr Asn Ala Ser Asn Ser Gly Gly Asn Tyr
    290                 295                 300
Asp Met Ala Lys Leu Leu Asn Gly Thr Val Val Gln Lys His Pro Met
305                 310                 315                 320
His Ala Val Thr Phe Val Asp Asn His Asp Ser Gln Pro Gly Glu Ser
                325                 330                 335
Leu Glu Ser Phe Val Gln Glu Trp Phe Lys Pro Leu Ala Tyr Ala Leu
            340                 345                 350
Ile Leu Thr Arg Glu Gln Gly Tyr Pro Ser Val Phe Tyr Gly Asp Tyr
        355                 360                 365
Tyr Gly Ile Pro Thr His Ser Val Pro Ala Met Lys Ala Lys Ile Asp
    370                 375                 380
Pro Ile Leu Glu Ala Arg Gln Asn Phe Ala Tyr Gly Thr Gln His Asp
385                 390                 395                 400
Tyr Phe Asp His His Asn Ile Ile Gly Trp Thr Arg Glu Gly Asn Thr
                405                 410                 415
Thr His Pro Asn Ser Gly Leu Ala Thr Ile Met Ser Asp Gly Pro Gly
            420                 425                 430
Gly Glu Lys Trp Met Tyr Val Gly Gln Asn Lys Ala Gly Gln Val Trp
        435                 440                 445
His Asp Ile Thr Gly Asn Lys Pro Gly Thr Val Thr Ile Asn Ala Asp
    450                 455                 460
Gly Trp Ala Asn Phe Ser Val Asn Gly Gly Ser Val Ser Ile Trp Val
465                 470                 475                 480
Lys Arg

<210> SEQ ID NO 23
<211> LENGTH: 484
<212> TYPE: PRT
```

<213> ORGANISM: Artificial sequence
<220> FEATURE:
<223> OTHER INFORMATION: Synthetic construct

<400> SEQUENCE: 23

```
His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Ala Gly Ala Asp
            100                 105                 110

Glu Thr Glu Val Phe Lys Val Ile Glu Val Asp Pro Asn Asp Arg Thr
        115                 120                 125

Lys Glu Ile Ser Glu Pro Phe Glu Ile Glu Gly Trp Thr Lys Phe Thr
130                 135                 140

Phe Pro Gly Arg Gly Asp Gln Tyr Ser Ser Phe Lys Trp Asn Ser Glu
145                 150                 155                 160

His Phe Asn Gly Thr Asp Phe Asp Ala Lys Gly Glu Arg Thr Gly Val
                165                 170                 175

Phe Arg Ile Ala Gly Glu Asn Lys Lys Trp Asn Glu Asn Val Asp Asp
            180                 185                 190

Glu Phe Gly Asn Tyr Asp Tyr Leu Met Phe Ala Asn Ile Asp Tyr Asn
        195                 200                 205

His Pro Asp Val Val Asn Glu Leu Arg Asn Trp Gly Val Trp Tyr Thr
210                 215                 220

Asn Thr Leu Gly Leu Asp Gly Phe Arg Ile Asp Ala Val Lys His Ile
225                 230                 235                 240

Lys Tyr Ser Phe Thr Arg Asp Trp Ile Asn His Val Arg Ser Ala Thr
                245                 250                 255

Gly Lys Asn Met Phe Ala Val Ala Glu Phe Trp Lys Asn Asp Leu Gly
            260                 265                 270

Ala Ile Glu Asn Tyr Leu Asn Lys Thr Asn Trp Asn His Ser Val Phe
        275                 280                 285

Asp Val Pro Leu His Tyr Asn Leu Tyr Asn Ala Ser Lys Ser Gly Gly
290                 295                 300

Asn Tyr Asp Met Arg Gln Ile Phe Asn Gly Thr Val Val Gln Arg His
305                 310                 315                 320

Pro Met His Ala Val Thr Phe Val Asp Asn His Asp Ser Gln Pro Glu
                325                 330                 335

Glu Ala Leu Glu Ser Phe Val Glu Glu Trp Phe Lys Pro Leu Ala Tyr
            340                 345                 350

Ala Leu Thr Leu Thr Arg Glu Gln Gly Tyr Pro Ser Val Phe Tyr Gly
        355                 360                 365

Asp Tyr Tyr Gly Ile Pro Thr His Gly Val Pro Ala Met Lys Ser Lys
370                 375                 380

Ile Asp Pro Ile Leu Glu Ala Arg Gln Lys Tyr Ala Tyr Gly Arg Gln
385                 390                 395                 400
```

Asn Asp Tyr Leu Asp His His Asn Ile Ile Gly Trp Thr Arg Glu Gly
                405                 410                 415

Asn Thr Ala His Pro Asn Ser Gly Leu Ala Thr Ile Met Ser Asp Gly
            420                 425                 430

Ala Gly Gly Asn Lys Trp Met Phe Val Gly Arg Asn Lys Ala Gly Gln
        435                 440                 445

Val Trp Thr Asp Ile Thr Gly Asn Arg Ala Gly Thr Val Thr Ile Asn
450                 455                 460

Ala Asp Gly Trp Gly Asn Phe Ser Val Asn Gly Gly Ser Val Ser Ile
465                 470                 475                 480

Trp Val Asn Lys

<210> SEQ ID NO 24
<211> LENGTH: 482
<212> TYPE: PRT
<213> ORGANISM: Artificial sequence
<220> FEATURE:
<223> OTHER INFORMATION: Synthetic construct

<400> SEQUENCE: 24

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Ala Gly Ala Asp
            100                 105                 110

Glu Thr Glu Val Phe Lys Val Ile Glu Val Asp Pro Asn Asp Arg Thr
        115                 120                 125

Lys Glu Ile Ser Glu Pro Phe Glu Ile Glu Gly Trp Thr Lys Phe Thr
130                 135                 140

Phe Pro Gly Arg Gly Asp Gln Tyr Ser Ser Phe Lys Trp Asn Ser Glu
145                 150                 155                 160

His Phe Asn Gly Thr Asp Phe Asp Ala Lys Gly Glu Arg Thr Gly Val
                165                 170                 175

Phe Arg Ile Ala Gly Lys Lys Trp Asn Trp Glu Val Asp Thr Glu Phe
            180                 185                 190

Gly Asn Tyr Asp Tyr Leu Met Phe Ala Asn Ile Asp Tyr Asn His Pro
        195                 200                 205

Asp Val Val Asn Glu Leu Arg Asn Trp Gly Val Trp Tyr Thr Asn Thr
210                 215                 220

Leu Gly Leu Asp Gly Phe Arg Ile Asp Ala Val Lys His Ile Lys Tyr
225                 230                 235                 240

Ser Phe Thr Arg Asp Trp Ile Asn His Val Arg Ser Ala Thr Gly Lys
                245                 250                 255

Asn Met Phe Ala Val Ala Glu Phe Trp Lys Asn Asp Leu Gly Ala Ile
            260                 265                 270

Glu Asn Tyr Leu Asn Lys Thr Asn Trp Asn His Ser Val Phe Asp Val

```
                275                 280                 285
Pro Leu His Tyr Asn Leu Tyr Asn Ala Ser Lys Ser Gly Gly Asn Tyr
290                 295                 300

Asp Met Arg Gln Ile Phe Asn Gly Thr Val Val Gln Lys His Pro Met
305                 310                 315                 320

His Ala Val Thr Phe Val Asp Asn His Asp Ser Gln Pro Glu Glu Ala
                325                 330                 335

Leu Glu Ser Phe Val Glu Glu Trp Phe Lys Pro Leu Ala Tyr Ala Leu
                340                 345                 350

Thr Leu Thr Arg Glu Gln Gly Tyr Pro Ser Val Phe Tyr Gly Asp Tyr
                355                 360                 365

Tyr Gly Ile Pro Thr His Gly Val Pro Ala Met Lys Ser Lys Ile Asp
370                 375                 380

Pro Ile Leu Glu Ala Arg Gln Lys Tyr Ala Tyr Gly Arg Gln Asn Asp
385                 390                 395                 400

Tyr Leu Asp His His Asn Ile Ile Gly Trp Thr Arg Glu Gly Asn Thr
                405                 410                 415

Ala His Pro Asn Ser Gly Leu Ala Thr Ile Met Ser Asp Gly Ala Gly
                420                 425                 430

Gly Asn Lys Trp Met Phe Val Gly Arg Asn Lys Ala Gly Gln Val Trp
                435                 440                 445

Thr Asp Ile Thr Gly Asn Lys Ala Gly Thr Val Thr Ile Asn Ala Asp
                450                 455                 460

Gly Trp Gly Asn Phe Ser Val Asn Gly Gly Ser Val Ser Ile Trp Val
465                 470                 475                 480

Asn Lys

<210> SEQ ID NO 25
<211> LENGTH: 484
<212> TYPE: PRT
<213> ORGANISM: Artificial sequence
<220> FEATURE:
<223> OTHER INFORMATION: Synthetic construct

<400> SEQUENCE: 25

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
                20                  25                  30

Asn Leu Lys Ser Lys Gly Ile Thr Ala Val Trp Ile Pro Pro Ala Trp
            35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Ala Gly Ala Asp
            100                 105                 110

Glu Thr Glu Val Phe Lys Val Ile Glu Val Asp Pro Asn Asp Arg Thr
        115                 120                 125

Lys Glu Ile Ser Glu Pro Phe Glu Ile Glu Gly Trp Thr Lys Phe Thr
130                 135                 140

Phe Pro Gly Arg Gly Asp Gln Tyr Ser Ser Phe Lys Trp Asn Ser Glu
145                 150                 155                 160
```

```
His Phe Asn Gly Thr Asp Phe Asp Ala Lys Gly Glu Arg Thr Gly Val
                165                 170                 175

Phe Arg Ile Ala Gly Glu Asn Lys Lys Trp Asn Glu Asn Val Asp Asp
            180                 185                 190

Glu Phe Gly Asn Tyr Asp Tyr Leu Met Phe Ala Asn Ile Asp Tyr Asn
        195                 200                 205

His Pro Asp Val Val Asn Glu Leu Arg Asn Trp Gly Val Trp Tyr Thr
    210                 215                 220

Asn Thr Leu Gly Leu Asp Gly Phe Arg Ile Asp Ala Val Lys His Ile
225                 230                 235                 240

Lys Tyr Ser Phe Thr Arg Asp Trp Ile Asn His Val Arg Ser Ala Thr
                245                 250                 255

Gly Lys Asn Met Phe Ala Val Ala Glu Phe Trp Lys Asn Asp Leu Gly
            260                 265                 270

Ala Ile Glu Asn Tyr Leu Gln Lys Thr Asn Trp Asn His Ser Val Phe
        275                 280                 285

Asp Val Pro Leu His Tyr Asn Leu Tyr Asn Ala Ser Lys Ser Gly Gly
    290                 295                 300

Asn Tyr Asp Met Arg Asn Ile Phe Asn Gly Thr Val Val Gln Arg His
305                 310                 315                 320

Pro Ser His Ala Val Thr Phe Val Asp Asn His Asp Ser Gln Pro Glu
                325                 330                 335

Glu Ala Leu Glu Ser Phe Val Glu Glu Trp Phe Lys Pro Leu Ala Tyr
            340                 345                 350

Ala Leu Thr Leu Thr Arg Glu Gln Gly Tyr Pro Ser Val Phe Tyr Gly
        355                 360                 365

Asp Tyr Tyr Gly Ile Pro Thr His Gly Val Pro Ala Met Arg Ser Lys
    370                 375                 380

Ile Asp Pro Ile Leu Glu Ala Arg Gln Lys Tyr Ala Tyr Gly Lys Gln
385                 390                 395                 400

Asn Asp Tyr Leu Asp His His Asn Ile Ile Gly Trp Thr Arg Glu Gly
                405                 410                 415

Asn Thr Ala His Pro Asn Ser Gly Leu Ala Thr Ile Met Ser Asp Gly
            420                 425                 430

Ala Gly Gly Ser Lys Trp Met Phe Val Gly Arg Asn Lys Ala Gly Gln
        435                 440                 445

Val Trp Ser Asp Ile Thr Gly Asn Arg Thr Gly Thr Val Thr Ile Asn
    450                 455                 460

Ala Asp Gly Trp Gly Asn Phe Ser Val Asn Gly Gly Ser Val Ser Ile
465                 470                 475                 480

Trp Val Asn Lys

<210> SEQ ID NO 26
<211> LENGTH: 482
<212> TYPE: PRT
<213> ORGANISM: Artificial sequence
<220> FEATURE:
<223> OTHER INFORMATION: Synthetic construct

<400> SEQUENCE: 26

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45
```

```
Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                    85                  90                  95

Ile Gln Val Tyr Gly Asp Val Val Met Asn His Lys Ala Gly Ala Asp
                100                 105                 110

Glu Thr Glu Val Phe Lys Val Ile Glu Val Asp Pro Asn Asp Arg Thr
            115                 120                 125

Lys Glu Ile Ser Glu Pro Phe Glu Ile Glu Gly Trp Thr Lys Phe Thr
            130                 135                 140

Phe Pro Gly Arg Gly Asp Gln Tyr Ser Ser Phe Lys Trp Asn Ser Glu
145                 150                 155                 160

His Phe Asn Gly Thr Asp Phe Asp Ala Lys Gly Glu Arg Thr Gly Val
                165                 170                 175

Phe Arg Ile Ala Gly Lys Lys Trp Asn Trp Glu Val Asp Thr Glu Phe
                180                 185                 190

Gly Asn Tyr Asp Tyr Leu Met Phe Ala Asn Ile Asp Tyr Asn His Pro
            195                 200                 205

Asp Val Val Asn Glu Leu Arg Asn Trp Gly Val Trp Tyr Thr Asn Thr
    210                 215                 220

Leu Gly Leu Asp Gly Phe Arg Ile Asp Ala Val Lys His Ile Lys Tyr
225                 230                 235                 240

Ser Phe Thr Arg Asp Trp Ile Asn His Val Arg Ser Ala Thr Gly Lys
                245                 250                 255

Asn Met Phe Ala Val Ala Glu Phe Trp Lys Asn Asp Leu Gly Ala Ile
                260                 265                 270

Glu Asn Tyr Leu Gln Lys Thr Asn Trp Asn His Ser Val Phe Asp Val
            275                 280                 285

Pro Leu His Tyr Asn Leu Tyr Asn Ala Ser Lys Ser Gly Gly Asn Tyr
    290                 295                 300

Asp Met Arg Asn Ile Phe Asn Gly Thr Val Val Gln Arg His Pro Ser
305                 310                 315                 320

His Ala Val Thr Phe Val Asp Asn His Asp Ser Gln Pro Glu Glu Ala
                325                 330                 335

Leu Glu Ser Phe Val Glu Glu Trp Phe Lys Pro Leu Ala Tyr Ala Leu
                340                 345                 350

Thr Leu Thr Arg Glu Gln Gly Tyr Pro Ser Val Phe Tyr Gly Asp Tyr
            355                 360                 365

Tyr Gly Ile Pro Thr His Gly Val Pro Ala Met Arg Ser Lys Ile Asp
    370                 375                 380

Pro Ile Leu Glu Ala Arg Gln Lys Tyr Ala Tyr Gly Lys Gln Asn Asp
385                 390                 395                 400

Tyr Leu Asp His His Asn Ile Ile Gly Trp Thr Arg Glu Gly Asn Thr
                405                 410                 415

Ala His Pro Asn Ser Gly Leu Ala Thr Ile Met Ser Asp Gly Ala Gly
                420                 425                 430

Gly Ser Lys Trp Met Phe Val Gly Arg Asn Lys Ala Gly Gln Val Trp
            435                 440                 445

Ser Asp Ile Thr Gly Asn Arg Thr Gly Thr Val Thr Ile Asn Ala Asp
    450                 455                 460

Gly Trp Gly Asn Phe Ser Val Asn Gly Gly Ser Val Ser Ile Trp Val
```

465             470             475             480

Asn Lys

<210> SEQ ID NO 27
<211> LENGTH: 515
<212> TYPE: PRT
<213> ORGANISM: Artificial sequence
<220> FEATURE:
<223> OTHER INFORMATION: Synthetic construct

<400> SEQUENCE: 27

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asn His Lys Ala Gly Ala Asp Glu
            100                 105                 110

Thr Glu Val Phe Lys Val Ile Glu Val Asp Pro Asn Asp Arg Thr Lys
        115                 120                 125

Glu Ile Ser Glu Pro Phe Glu Ile Glu Gly Trp Thr Lys Phe Thr Phe
    130                 135                 140

Pro Gly Arg Gly Asp Gln Tyr Ser Ser Phe Lys Trp Asn Ser Glu His
145                 150                 155                 160

Phe Asn Gly Thr Asp Phe Asp Ala Lys Gly Glu Arg Thr Gly Val Phe
                165                 170                 175

Arg Ile Ala Gly Glu Asn Lys Lys Trp Asn Glu Asn Val Asp Asp Glu
            180                 185                 190

Phe Gly Asn Tyr Asp Tyr Leu Met Phe Ala Asn Ile Asp Tyr Asn His
        195                 200                 205

Pro Asp Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

```
Phe Ile Leu Thr Arg Gln Glu Gly Tyr Pro Cys Val Phe Tyr Gly Asp
            355                 360                 365
Tyr Tyr Gly Ile Pro Gln Tyr Asn Ile Pro Ser Leu Lys Ser Lys Ile
    370                 375                 380
Asp Pro Leu Leu Ile Ala Arg Arg Asp Tyr Ala Tyr Gly Thr Gln His
385                 390                 395                 400
Asp Tyr Leu Asp His Ser Asp Ile Ile Gly Trp Thr Arg Glu Gly Val
                405                 410                 415
Thr Glu Lys Pro Gly Ser Gly Leu Ala Ala Leu Ile Thr Asp Gly Pro
            420                 425                 430
Gly Gly Ser Lys Trp Met Tyr Val Gly Lys Gln His Ala Gly Lys Val
            435                 440                 445
Phe Tyr Asp Leu Thr Gly Asn Arg Ser Asp Thr Val Thr Ile Asn Ser
    450                 455                 460
Asp Gly Trp Gly Glu Phe Lys Val Asn Gly Gly Ser Val Ser Val Trp
465                 470                 475                 480
Val Pro Arg Lys Thr Thr Val Ser Thr Ile Ala Arg Pro Ile Thr Thr
                485                 490                 495
Arg Pro Trp Thr Gly Glu Phe Val Arg Trp Thr Glu Pro Arg Leu Val
            500                 505                 510
Ala Trp Pro
        515

<210> SEQ ID NO 28
<211> LENGTH: 491
<212> TYPE: PRT
<213> ORGANISM: Artificial sequence
<220> FEATURE:
<223> OTHER INFORMATION: Synthetic construct

<400> SEQUENCE: 28

Ala Ala Pro Phe Asn Gly Thr Met Met Gln Tyr Phe Glu Trp Tyr Leu
1               5                   10                  15
Pro Asp Asp Gly Thr Leu Trp Thr Lys Val Ala Asn Glu Ala Asn Asn
            20                  25                  30
Leu Ser Ser Leu Gly Ile Thr Ala Leu Trp Leu Pro Pro Ala Tyr Lys
        35                  40                  45
Gly Thr Ser Arg Ser Asp Val Gly Tyr Gly Val Tyr Asp Leu Tyr Asp
    50                  55                  60
Leu Gly Glu Phe Asn Gln Lys Gly Thr Val Arg Thr Lys Tyr Gly Thr
65                  70                  75                  80
Lys Ala Gln Tyr Leu Gln Ala Ile Gln Ala Ala His Ala Ala Gly Met
                85                  90                  95
Gln Val Tyr Ala Asp Val Val Phe Asn His Lys Ala Gly Ala Asp Glu
            100                 105                 110
Thr Glu Val Phe Lys Val Ile Glu Val Asp Pro Asn Asp Arg Thr Lys
        115                 120                 125
Glu Ile Ser Glu Pro Phe Glu Ile Gly Trp Thr Lys Phe Thr Phe Phe
    130                 135                 140
Pro Gly Arg Gly Asp Gln Tyr Ser Ser Phe Lys Trp Asn Ser Glu His
145                 150                 155                 160
Phe Asn Gly Thr Asp Phe Asp Ala Lys Gly Glu Arg Thr Gly Val Phe
                165                 170                 175
Arg Ile Ala Gly Lys Lys Trp Asn Trp Glu Val Asp Thr Glu Phe Gly
            180                 185                 190
Asn Tyr Asp Tyr Leu Met Phe Ala Asn Ile Asp Tyr Asn His Pro Asp
```

```
                195                 200                 205
Val Val Thr Glu Leu Lys Asn Trp Gly Lys Trp Tyr Val Asn Thr Thr
210                 215                 220

Asn Ile Asp Gly Phe Arg Leu Asp Ala Val Lys His Ile Lys Phe Ser
225                 230                 235                 240

Phe Phe Pro Asp Trp Leu Ser Tyr Val Arg Ser Gln Thr Gly Lys Pro
                245                 250                 255

Leu Phe Thr Val Gly Glu Tyr Trp Ser Tyr Asp Ile Asn Lys Leu His
                260                 265                 270

Asn Tyr Ile Thr Lys Thr Asp Gly Thr Met Ser Leu Phe Asp Ala Pro
                275                 280                 285

Leu His Asn Lys Phe Tyr Thr Ala Ser Lys Ser Gly Gly Ala Phe Asp
                290                 295                 300

Met Arg Thr Leu Met Thr Asn Thr Leu Met Lys Asp Gln Pro Thr Leu
305                 310                 315                 320

Ala Val Thr Phe Val Asp Asn His Asp Thr Glu Pro Gly Gln Ala Leu
                325                 330                 335

Gln Ser Trp Val Asp Pro Trp Phe Lys Pro Leu Ala Tyr Ala Phe Ile
                340                 345                 350

Leu Thr Arg Gln Glu Gly Tyr Pro Cys Val Phe Tyr Gly Asp Tyr Tyr
                355                 360                 365

Gly Ile Pro Gln Tyr Asn Ile Pro Ser Leu Lys Ser Lys Ile Asp Pro
                370                 375                 380

Leu Leu Ile Ala Arg Arg Asp Tyr Ala Tyr Gly Thr Gln His Asp Tyr
385                 390                 395                 400

Leu Asp His Ser Asn Ile Ile Gly Trp Thr Arg Glu Gly Gly Thr Glu
                405                 410                 415

Lys Pro Gly Ser Gly Leu Ala Ala Leu Ile Thr Asn Gly Asp Gly Gly
                420                 425                 430

Ser Lys Trp Met Tyr Val Gly Lys Gln His Ala Gly Lys Val Phe Tyr
                435                 440                 445

Asp Leu Thr Gly Asn Arg Ser Asp Thr Val Thr Ile Asn Ser Asp Gly
                450                 455                 460

Trp Gly Glu Phe Lys Val Asn Gly Gly Ser Val Ser Val Trp Val Pro
465                 470                 475                 480

Arg Lys Thr Thr Val Ser Thr Ile Ala Arg Pro
                485                 490

<210> SEQ ID NO 29
<211> LENGTH: 486
<212> TYPE: PRT
<213> ORGANISM: Bacillus stearothermophilus

<400> SEQUENCE: 29

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
                20                  25                  30

Leu Ser Ser Leu Gly Ile Thr Ala Leu Trp Leu Pro Pro Ala Tyr Lys
                35                  40                  45

Gly Thr Ser Arg Ser Asp Val Gly Tyr Gly Val Tyr Asp Leu Tyr Asp
                50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
```

```
                85                  90                  95
Gln Val Tyr Ala Asp Val Phe Asp His Lys Gly Ala Asp Gly
            100                 105                 110

Thr Glu Trp Val Asp Ala Val Glu Val Asn Pro Ser Asp Arg Asn Gln
            115                 120                 125

Glu Ile Ser Gly Thr Tyr Gln Ile Gln Ala Trp Thr Lys Phe Asp Phe
            130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
            195                 200                 205

Pro Glu Val Val Thr Glu Leu Lys Asn Trp Gly Lys Trp Tyr Val Asn
210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
            275                 280                 285

Ala Pro Leu His Asn Lys Phe Tyr Thr Ala Ser Lys Ser Gly Gly Ala
            290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
            355                 360                 365

Tyr Tyr Gly Ile Pro Gln Tyr Asn Ile Pro Ser Leu Lys Ser Lys Ile
            370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
450                 455                 460

Asp Gly Trp Gly Glu Phe Lys Val Asn Gly Gly Ser Val Ser Val Trp
465                 470                 475                 480

Val Pro Arg Lys Thr Thr
            485

<210> SEQ ID NO 30
<211> LENGTH: 485
```

```
<212> TYPE: PRT
<213> ORGANISM: Cytophaga

<400> SEQUENCE: 30

Ala Ala Thr Asn Gly Thr Met Met Gln Tyr Phe Glu Trp Tyr Val Pro
1               5                   10                  15

Asn Asp Gly Gln Gln Trp Asn Arg Leu Arg Thr Asp Ala Pro Tyr Leu
            20                  25                  30

Ser Ser Val Gly Ile Thr Ala Val Trp Thr Pro Pro Ala Tyr Lys Gly
        35                  40                  45

Thr Ser Gln Ala Asp Val Gly Tyr Gly Pro Tyr Asp Leu Tyr Asp Leu
    50                  55                  60

Gly Glu Phe Asn Gln Lys Gly Thr Val Arg Thr Lys Tyr Gly Thr Lys
65                  70                  75                  80

Gly Glu Leu Lys Ser Ala Val Asn Thr Leu His Ser Asn Gly Ile Gln
                85                  90                  95

Val Tyr Gly Asp Val Val Met Asn His Lys Ala Gly Ala Asp Tyr Thr
            100                 105                 110

Glu Asn Val Thr Ala Val Glu Val Asn Pro Ser Asn Arg Asn Gln Glu
        115                 120                 125

Thr Ser Gly Glu Tyr Asn Ile Gln Ala Trp Thr Gly Phe Asn Phe Pro
    130                 135                 140

Gly Arg Gly Thr Thr Tyr Ser Asn Phe Lys Trp Gln Trp Phe His Phe
145                 150                 155                 160

Asp Gly Thr Asp Trp Asp Gln Ser Arg Ser Leu Ser Arg Ile Phe Lys
                165                 170                 175

Phe Arg Gly Thr Gly Lys Ala Trp Asp Trp Glu Val Ser Ser Glu Asn
            180                 185                 190

Gly Asn Tyr Asp Tyr Leu Met Tyr Ala Asp Ile Asp Tyr Asp His Pro
        195                 200                 205

Asp Val Val Asn Glu Met Lys Lys Trp Gly Val Trp Tyr Ala Asn Glu
    210                 215                 220

Val Gly Leu Asp Gly Tyr Arg Leu Asp Ala Val Lys His Ile Lys Phe
225                 230                 235                 240

Ser Phe Leu Lys Asp Trp Val Asp Asn Ala Arg Ala Ala Thr Gly Lys
                245                 250                 255

Glu Met Phe Thr Val Gly Glu Tyr Trp Gln Asn Asp Leu Gly Ala Leu
            260                 265                 270

Asn Asn Tyr Leu Ala Lys Val Asn Tyr Asn Gln Ser Leu Phe Asp Ala
        275                 280                 285

Pro Leu His Tyr Asn Phe Tyr Ala Ala Ser Thr Gly Gly Gly Tyr Tyr
    290                 295                 300

Asp Met Arg Asn Ile Leu Asn Asn Thr Leu Val Ala Ser Asn Pro Thr
305                 310                 315                 320

Lys Ala Val Thr Leu Val Glu Asn His Asp Thr Gln Pro Gly Gln Ser
                325                 330                 335

Leu Glu Ser Thr Val Gln Pro Trp Phe Lys Pro Leu Ala Tyr Ala Phe
            340                 345                 350

Ile Leu Thr Arg Ser Gly Gly Tyr Pro Ser Val Phe Tyr Gly Asp Met
        355                 360                 365

Tyr Gly Thr Lys Gly Thr Thr Thr Arg Glu Ile Pro Ala Leu Lys Ser
    370                 375                 380

Lys Ile Glu Pro Leu Leu Lys Ala Arg Lys Asp Tyr Ala Tyr Gly Thr
385                 390                 395                 400
```

```
Gln Arg Asp Tyr Ile Asp Asn Pro Asp Val Ile Gly Trp Thr Arg Glu
                405                 410                 415

Gly Asp Ser Thr Lys Ala Lys Ser Gly Leu Ala Thr Val Ile Thr Asp
            420                 425                 430

Gly Pro Gly Gly Ser Lys Arg Met Tyr Val Gly Thr Ser Asn Ala Gly
        435                 440                 445

Glu Ile Trp Tyr Asp Leu Thr Gly Asn Arg Thr Asp Lys Ile Thr Ile
    450                 455                 460

Gly Ser Asp Gly Tyr Ala Thr Phe Pro Val Asn Gly Ser Val Ser
465                 470                 475                 480

Val Trp Val Gln Gln
            485

<210> SEQ ID NO 31
<211> LENGTH: 435
<212> TYPE: PRT
<213> ORGANISM: Artificial sequence
<220> FEATURE:
<223> OTHER INFORMATION: Synthetic construct

<400> SEQUENCE: 31

Ala Lys Tyr Ser Glu Leu Glu Lys Gly Gly Val Ile Met Gln Ala Phe
1               5                   10                  15

Tyr Trp Asp Val Pro Ser Gly Gly Ile Trp Trp Asp Thr Ile Arg Gln
            20                  25                  30

Lys Ile Pro Glu Trp Tyr Asp Ala Gly Ile Ser Ala Ile Trp Ile Pro
        35                  40                  45

Pro Ala Ser Lys Gly Met Gly Gly Ala Tyr Ser Met Gly Tyr Asp Pro
    50                  55                  60

Tyr Asp Phe Phe Asp Leu Gly Tyr Asp Gln Lys Gly Thr Val Glu
65                  70                  75                  80

Thr Arg Phe Gly Ser Lys Gln Glu Leu Val Asn Met Ile Asn Thr Ala
                85                  90                  95

His Ala Tyr Gly Met Lys Val Ile Ala Asp Ile Val Ile Asn His Arg
            100                 105                 110

Ala Gly Gly Asp Leu Glu Trp Asn Pro Phe Val Asn Asp Tyr Thr Trp
        115                 120                 125

Thr Asp Phe Ser Lys Val Ala Ser Gly Lys Tyr Thr Ala Asn Tyr Leu
    130                 135                 140

Asp Phe His Pro Asn Glu Leu His Ala Gly Asp Ser Gly Thr Phe Gly
145                 150                 155                 160

Gly Tyr Pro Asp Ile Cys His Asp Lys Ser Trp Asp Gln Tyr Trp Leu
                165                 170                 175

Trp Ala Ser Gln Glu Ser Tyr Ala Ala Tyr Leu Arg Ser Ile Gly Ile
            180                 185                 190

Asp Ala Trp Arg Phe Asp Tyr Val Lys Gly Tyr Ala Pro Trp Val Val
        195                 200                 205

Lys Asp Trp Leu Asn Trp Trp Gly Gly Trp Ala Val Gly Glu Tyr Trp
    210                 215                 220

Asp Thr Asn Val Asp Ala Val Leu Asn Trp Ala Tyr Ser Ser Gly Ala
225                 230                 235                 240

Lys Val Phe Asp Phe Ala Leu Tyr Tyr Lys Met Asp Glu Ala Phe Asp
                245                 250                 255

Asn Lys Asn Ile Pro Ala Leu Val Ser Ala Leu Gln Asn Gly Gln Thr
            260                 265                 270

Val Val Ser Arg Asp Pro Phe Lys Ala Val Thr Phe Val Ala Asn His
```

```
                   275                 280                 285
Asp Thr Asp Ile Ile Trp Asn Lys Tyr Pro Ala Tyr Ala Phe Ile Leu
290                 295                 300

Thr Tyr Glu Gly Gln Pro Thr Ile Phe Tyr Arg Asp Tyr Glu Glu Trp
305                 310                 315                 320

Leu Asn Lys Asp Lys Leu Lys Asn Leu Ile Trp Ile His Glu Asn Leu
                325                 330                 335

Ala Gly Gly Ser Thr Asp Ile Val Tyr Asp Asn Asp Glu Leu Ile
                340                 345                 350

Phe Val Arg Asn Gly Tyr Gly Asp Lys Pro Gly Leu Ile Thr Tyr Ile
                355                 360                 365

Asn Leu Gly Ser Ser Lys Ala Gly Arg Trp Val Tyr Val Pro Lys Phe
                370                 375                 380

Ala Gly Ala Cys Ile His Glu Tyr Thr Gly Asn Leu Gly Gly Trp Val
385                 390                 395                 400

Asp Lys Tyr Val Tyr Ser Ser Gly Trp Val Tyr Leu Glu Ala Pro Ala
                405                 410                 415

Tyr Asp Pro Ala Asn Gly Gln Tyr Gly Tyr Ser Val Trp Ser Tyr Cys
                420                 425                 430

Gly Val Gly
        435

<210> SEQ ID NO 32
<211> LENGTH: 482
<212> TYPE: PRT
<213> ORGANISM: Artificial sequence
<220> FEATURE:
<223> OTHER INFORMATION: Synthetic construct

<400> SEQUENCE: 32

His His Asn Gly Thr Asn Gly Thr Leu Met Gln Tyr Phe Glu Trp Tyr
1               5                   10                  15

Leu Pro Asn Asp Gly Asn His Trp Asn Arg Leu Arg Ser Asp Ala Ser
                20                  25                  30

Asn Leu Lys Asp Lys Gly Ile Ser Ala Val Trp Ile Pro Pro Ala Trp
            35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Ala Gly Ala Asp
            100                 105                 110

Glu Thr Glu Val Phe Lys Val Ile Glu Val Asp Pro Asn Asp Arg Thr
        115                 120                 125

Lys Glu Ile Ser Glu Pro Phe Glu Ile Glu Gly Trp Thr Lys Phe Thr
130                 135                 140

Phe Pro Gly Arg Gly Asp Gln Tyr Ser Ser Phe Lys Trp Asn Ser Glu
145                 150                 155                 160

His Phe Asn Gly Thr Asp Phe Asp Ala Lys Gly Glu Arg Thr Gly Val
                165                 170                 175

Phe Arg Ile Ala Gly Lys Lys Trp Asn Trp Glu Val Asp Thr Glu Phe
            180                 185                 190

Gly Asn Tyr Asp Tyr Leu Met Phe Ala Asn Ile Asp Tyr Asn His Pro
        195                 200                 205
```

Asp Val Val Asn Glu Leu Arg Asn Trp Gly Val Trp Tyr Thr Asn Thr
    210                 215                 220

Leu Gly Leu Asp Gly Phe Arg Ile Asp Ala Val Lys His Ile Lys Tyr
225                 230                 235                 240

Ser Phe Thr Arg Asp Trp Ile Asn His Val Arg Ser Ala Ile Gly Lys
                245                 250                 255

Asn Met Phe Ala Val Ala Glu Phe Trp Lys Asn Asp Leu Gly Ala Ile
                260                 265                 270

Glu Asn Tyr Leu Asn Lys Thr Asn Trp Asn His Ser Val Phe Asp Val
            275                 280                 285

Pro Leu His Phe Asn Leu Tyr Tyr Ala Ser Lys Ser Gly Gly Asn Tyr
        290                 295                 300

Asp Met Arg Gln Ile Phe Asn Gly Thr Val Val Gln Lys His Pro Thr
305                 310                 315                 320

His Ala Val Thr Phe Val Asp Asn His Asp Ser Gln Pro Glu Glu Ser
                325                 330                 335

Leu Glu Ser Phe Val Arg Glu Trp Phe Lys Pro Leu Ala Tyr Ala Leu
                340                 345                 350

Thr Leu Thr Arg Glu Gln Gly Tyr Pro Ser Val Phe Tyr Gly Asp Tyr
            355                 360                 365

Tyr Gly Ile Pro Thr His Gly Val Pro Ala Met Lys Ser Lys Ile Asp
        370                 375                 380

Pro Ile Leu Glu Ala Arg Gln Lys Tyr Ala Tyr Gly Arg Gln Asn Asp
385                 390                 395                 400

Tyr Leu Asp His His Asn Ile Ile Gly Trp Thr Arg Glu Gly Asn Thr
                405                 410                 415

Ala His Pro Asn Ser Gly Leu Ala Thr Ile Met Ser Asp Gly Ala Gly
                420                 425                 430

Gly Asn Lys Trp Met Phe Val Gly Arg Asn Lys Ala Gly Gln Val Trp
            435                 440                 445

Thr Asp Ile Thr Gly Asn Lys Ala Gly Thr Val Thr Ile Asn Ala Asp
        450                 455                 460

Gly Trp Gly Asn Phe Ser Val Asn Gly Gly Ser Val Ser Ile Trp Val
465                 470                 475                 480

Asn Lys

<210> SEQ ID NO 33
<211> LENGTH: 484
<212> TYPE: PRT
<213> ORGANISM: Artificial sequence
<220> FEATURE:
<223> OTHER INFORMATION: Synthetic construct

<400> SEQUENCE: 33

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
                20                  25                  30

Asn Leu Lys Ser Lys Gly Ile Thr Ala Val Trp Ile Pro Pro Ala Trp
            35                  40                  45

Lys Gly Ala Ser Gln Asn Asp Val Gly Tyr Gly Ala Tyr Asp Leu Tyr
        50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly

```
                     85                  90                  95
Ile Gln Val Tyr Gly Asp Val Val Met Asn His Lys Ala Gly Ala Asp
                100                 105                 110

Glu Thr Glu Val Phe Lys Val Ile Glu Val Asp Pro Asn Asp Arg Thr
            115                 120                 125

Lys Glu Ile Ser Glu Pro Phe Glu Ile Glu Gly Trp Thr Lys Phe Thr
        130                 135                 140

Phe Pro Gly Arg Gly Asp Gln Tyr Ser Ser Phe Lys Trp Asn Ser Glu
145                 150                 155                 160

His Phe Asn Gly Thr Asp Phe Asp Ala Lys Gly Glu Arg Thr Gly Val
                165                 170                 175

Phe Arg Ile Ala Gly Glu Asn Lys Lys Trp Asn Glu Asn Val Asp Asp
            180                 185                 190

Glu Phe Gly Asn Tyr Asp Tyr Leu Met Phe Ala Asn Ile Asp Tyr Asn
        195                 200                 205

His Pro Asp Val Val Asn Glu Leu Arg Asn Trp Gly Val Trp Tyr Thr
    210                 215                 220

Asn Thr Leu Gly Leu Asp Gly Phe Arg Ile Asp Ala Val Lys His Ile
225                 230                 235                 240

Lys Tyr Ser Phe Thr Arg Asp Trp Ile Asn His Val Arg Ser Ala Thr
                245                 250                 255

Gly Lys Asn Met Phe Ala Val Ala Glu Phe Trp Lys Asn Asp Leu Gly
            260                 265                 270

Ala Ile Glu Asn Tyr Leu Gln Lys Thr Asn Trp Asn His Ser Val Phe
        275                 280                 285

Asp Val Pro Leu His Tyr Asn Leu Tyr Asn Ala Ser Lys Ser Gly Gly
    290                 295                 300

Asn Tyr Asp Met Arg Asn Ile Phe Asn Gly Thr Val Val Gln Arg His
305                 310                 315                 320

Pro Ser His Ala Val Thr Phe Val Asp Asn His Asp Ser Gln Pro Glu
                325                 330                 335

Glu Ala Leu Glu Ser Phe Val Glu Glu Trp Phe Lys Pro Leu Ala Tyr
            340                 345                 350

Ala Leu Thr Leu Thr Arg Glu Gln Gly Tyr Pro Ser Val Phe Tyr Gly
        355                 360                 365

Asp Tyr Tyr Gly Ile Pro Thr His Gly Val Pro Ala Met Arg Ser Lys
    370                 375                 380

Ile Asp Pro Ile Leu Glu Ala Arg Gln Lys Tyr Ala Tyr Gly Lys Gln
385                 390                 395                 400

Asn Asp Tyr Leu Asp His His Asn Ile Ile Gly Trp Thr Arg Glu Gly
                405                 410                 415

Asn Thr Ala His Pro Asn Ser Gly Leu Ala Thr Ile Met Ser Asp Gly
            420                 425                 430

Ala Gly Gly Ser Lys Trp Met Phe Val Gly Arg Asn Lys Ala Gly Gln
        435                 440                 445

Val Trp Ser Asp Ile Thr Gly Asn Arg Thr Gly Thr Val Thr Ile Asn
    450                 455                 460

Ala Asp Gly Trp Gly Asn Phe Ser Val Asn Gly Gly Ser Val Ser Ile
465                 470                 475                 480

Trp Val Asn Lys

<210> SEQ ID NO 34
<211> LENGTH: 483
<212> TYPE: PRT
```

<213> ORGANISM: Artificial sequence
<220> FEATURE:
<223> OTHER INFORMATION: Synthetic construct

<400> SEQUENCE: 34

```
Ala Ala Val Asn Gly Thr Leu Met Gln Tyr Phe Glu Trp Tyr Thr Pro
1               5                   10                  15

Asn Asp Gly Gln His Trp Lys Arg Leu Gln Asn Asp Ala Glu His Leu
            20                  25                  30

Ser Asp Ile Gly Ile Thr Ala Val Trp Ile Pro Pro Ala Tyr Lys Ala
        35                  40                  45

Ile Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asp His Lys Ala Gly Ala Asp Glu Thr
            100                 105                 110

Glu Val Phe Lys Val Ile Glu Val Asp Pro Asn Asp Arg Thr Lys Glu
        115                 120                 125

Ile Ser Glu Pro Phe Glu Ile Glu Gly Trp Thr Lys Phe Thr Phe Pro
    130                 135                 140

Gly Arg Gly Asp Thr Tyr Ser Ser Phe Lys Trp Asn Ser Glu His Phe
145                 150                 155                 160

Asn Gly Val Asp Phe Asp Ala Lys Gly Glu Arg Thr Gly Val Phe Arg
                165                 170                 175

Ile Ala Gly Lys Ala Trp Asn Trp Glu Val Asp Thr Glu Phe Gly Asn
            180                 185                 190

Tyr Asp Tyr Leu Met Phe Ala Asn Ile Asp Tyr Asn His Pro Asp Val
        195                 200                 205

Val Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Ser Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Gly Tyr Asp Met
    290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Asp Ser Gln Arg Glu Ile Pro Ala Leu Lys His Lys Ile
    370                 375                 380

Glu Pro Ile Leu Lys Ala Arg Lys Gln Tyr Ala Tyr Gly Ala Gln His
385                 390                 395                 400
```

```
Asp Tyr Phe Asp His His Asp Ile Val Gly Trp Thr Arg Glu Gly Asp
            405             410                 415

Ser Ser Val Ala Asn Ser Gly Leu Ala Ala Leu Ile Thr Asp Gly Pro
            420             425             430

Gly Gly Ala Lys Arg Met Tyr Val Gly Arg Gln Asn Ala Gly Glu Thr
            435             440             445

Trp His Asp Ile Thr Gly Asn Arg Ser Glu Pro Val Val Ile Asn Ser
        450             455             460

Glu Gly Trp Gly Glu Phe His Val Asn Gly Gly Ser Val Ser Ile Tyr
465                     470             475                 480

Val Gln Arg
```

ALPHA-AMYLASES

CROSS-REFERENCE TO RELATED APPLICATIONS

This application is a 35 U.S.C. 371 national application of PCT/EP2011/050073 filed Jan. 4, 2011, which claims priority or the benefit under 35 U.S.C. 119 of European application nos. 10150063.5 and 10150062.7 filed Jan. 4, 2010 and Jan. 4, 2010, respectively, and U.S. provisional application Nos. 61/292,324, 61/292,327 61/304,092, 61/333,930, 61/354,775, 61/354,817, 61/355,230 and 61/362,536 filed Jan. 5, 2010, Jan. 5, 2010, Feb. 12, 2010, May 12, 2010, Jun. 15, 2010, Jun. 15, 2010, Jun. 16, 2010 and Jul. 8, 2010, respectively, the contents of which are fully incorporated herein by reference.

REFERENCE TO SEQUENCE LISTING

This application contains a Sequence Listing in computer readable form, which is incorporated herein by reference.

FIELD OF THE INVENTION

The present invention relates to alpha-amylases, nucleic acids encoding the alpha-amylases, methods of producing the alpha-amylases, and methods of using the alpha-amylases.

BACKGROUND OF THE INVENTION

Alpha-amylases (alpha-1,4-glucan-4-glucanohydrolases, E.C. 3.2.1.1) constitute a group of enzymes, which catalyze the hydrolysis of starch and other linear and branched 1,4-glucosidic oligo- and polysaccharides.

There is a long history of industrial use of alpha-amylases in several known applications such as detergent, baking, brewing, starch liquefaction and saccharification, e.g., in the production of high fructose syrups or ethanol. These and other applications utilize alpha-amylases derived from microorganisms, in particular bacterial alpha-amylases.

One of the first bacterial alpha-amylases to be used was an alpha-amylase from *B. licheniformis*, also known as Termamyl™, which has been extensively characterized and the crystal structure has been determined for this enzyme. Alkaline amylases, such as the alpha-amylase derived from *Bacillus* sp. strains NCIB 12289, NCIB 12512, NCIB 12513, and DSM 9375 (disclosed in WO 95/26397), form a particular group of alpha-amylases that are useful in detergents. Many of these known bacterial amylases have been modified in order to improve their functionality in a particular application.

Termamyl™ and many highly efficient alpha-amylases require calcium for activity. The crystal structure of Termamyl™ shows that three calcium atoms are bound to the alpha-amylase structure coordinated by negatively charged amino acid residues. This requirement for calcium is a disadvantage in applications where strong chelating compounds are present, such as in detergents or during ethanol production from whole grains, where the plant material comprises a large amount of natural chelators such as phytate.

Calcium-insensitive amylases are known, e.g., the alpha-amylases disclosed in EP 1022334 and WO 03/083054, and a *Bacillus circulans* alpha-amylase having the sequence disclosed in UNIPROT:Q03657.

It would therefore be beneficial to provide alpha-amylases with reduced calcium sensitivity.

SUMMARY OF THE INVENTION

The present invention relates to alpha-amylases comprising the A- and C-domains of a calcium-sensitive alpha-amylase and the B-domain or a part thereof of a calcium-insensitive alpha-amylase. The alpha-amylases have high stability and/or activity in the presence of a strong chelator and further have considerably improved performance in various industrial applications.

The invention also relates to compositions comprising the alpha-amylases of the invention, such as detergent compositions.

In addition, the invention relates to nucleic acids encoding the alpha-amylases of the invention, plasmids comprising such nucleic acids, host cells comprising such a plasmid or nucleic acid, and methods for producing the alpha-amylases.

BRIEF DESCRIPTION OF THE FIGURES

FIG. 1 shows an alignment of the alpha-amylases having the amino acid sequences of SEQ ID NOS: 1-16, 29, and 30.

DETAILED DESCRIPTION OF THE INVENTION

Definitions

A-, B- and C-domains: The structure of alpha-amylases comprises three distinct domains A, B and C, see, e.g., Machius et al., 1995, *J. Mol. Biol.* 246: 545-559. The term "domain" means a region of a polypeptide that in itself forms a distinct and independent substructure of the whole molecule. Alpha-amylases consist of a beta/alpha-8 barrel harboring the active site, which is denoted the A-domain, a rather long loop between the beta-sheet 3 and alpha-helix 3, which is denoted the B-domain, and a C-domain and in some cases also a carbohydrate binding domain (e.g., WO 2005/001064; Machius et al., supra).

The domains of an alpha-amylase can be determined by structure analysis such as by using crystallographically techniques. An alternative method for determining the domains of an alpha-amylase is by sequence alignment of the amino acid sequence of the alpha-amylase with another alpha-amylase for which the domains have been determined. The sequence that aligns with, e.g., the B-domain sequence in the alpha-amylase for which the B-domain has been determined can be considered the B-domain for the given alpha-amylase.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-Amylase (alpha-1,4-glucan-4-glucanohydrolases, E.C. 3.2.1.1) constitute a group of enzymes, which catalyze the hydrolysis of starch and other linear and branched 1,4-glucosidic oligo- and polysaccharides. Alpha-amylases derived from a wide selection of organisms including bacteria, such as from species of the genus *Bacillus*, e.g., *Bacillus licheniformis*; from species of fungi, such as *Aspergillus oryzae* (TAKA-amylase) or *Aspergillus niger*, from plants such as barley and from mammals, are known.

Calcium-insensitive amylase means an alpha-amylase that does not require the presence of calcium for optimal activity and/or for maintaining the active conformation/structure.

Calcium-sensitive amylase means an alpha-amylase that requires the presence of calcium to retain its structure and/or to have full enzymatic activity. For some calcium-sensitive amylases it has been shown that they contain a calcium atom coordinated to acidic amino acid residues in the active conformation. A large number of calcium-sensitive alpha-amylases are known and have been used industrially because of their beneficial properties. Calcium-sensitive alpha-amylases are generally sensitive towards conditions that lead to loss of the calcium atom coordinated in their structure such as detergent compositions and fuel mass.

Calcium sensitivity is determined by incubating a given alpha-amylase in the presence of a strong chelator and analyzing the impact of this incubation on the activity or stability of the alpha-amylase. A calcium-sensitive alpha-amylase will be less stable in the presence of a chelator or lose a major part or all of its activity by such incubation whereas a calcium-insensitive alpha-amylase will not lose activity or will only lose a minor part of the activity during incubation. Chelator strength may be evaluated using methods known in the art such as the methods disclosed in Nielsen et al., 2003, *Anal. Biochem.* 314: 227-234; and Nagarajan and Paine, 1984, *J. Am. Oil Chem. Soc.* 61(9): 1475-1478, which are incorporated herein by reference. Examples of strong chelators that may be used for such an assay are EGTA (ethylene glycol tetraacetic acid), EDTA (ethylene diamine tetraacetic acid), DTPA (diethylene triamine pentaacetic acid), DTMPA (diethylene triamine-penta-methylene phosphonic acid) and HEDP (1-hydroxyethan-1,1-diylbis(phosphonic acid)). Other strong chelators may be used to determine the calcium sensitivity of an alpha-amylase. Persons of ordinary skill in the art would be able to determine the temperature, pH and calcium concentration to use for determining calcium sensitivity. Typically, one uses a temperature which is about 5-10 degrees greater than the temperature optimum.

Coding sequence: The term "coding sequence" means a polynucleotide, which directly specifies the amino acid sequence of its polypeptide product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

Control sequence: The term "control sequence" means all components necessary for the expression of a polynucleotide encoding an alpha-amylase of the present invention. Each control sequence may be native or foreign to the polynucleotide encoding the alpha-amylase or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding an alpha-amylase.

Expression: The term "expression" includes any step involved in the production of the polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide of the present invention and is operably linked to additional nucleotides that provide for its expression.

Host cell: The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with an alpha-amylase that is improved compared to other alpha-amylases. Such improved properties include, but are not limited to, altered temperature-dependent activity profile, thermostability, pH activity, pH stability, substrate specificity, product specificity, and chemical stability.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence.

Operably linked: The term "operably linked" means a configuration in which a control sequence is placed at an appropriate position relative to the coding sequence of the polynucleotide sequence such that the control sequence directs the expression of the coding sequence of a polypeptide.

Parent Enzyme: The term "parent" alpha-amylase means an alpha-amylase to which modifications are made to produce an alpha-amylase of the present invention. The parent may be a naturally occurring (wild-type) polypeptide, or a variant thereof, prepared by any suitable means. For instance, the parent protein may be a variant of a naturally occurring polypeptide which has a modified or altered amino acid sequence. A parent may also be an allelic variant.

Polypeptide fragment: The term "polypeptide fragment" means a polypeptide having one or more (several) amino acids deleted from the amino and/or carboxyl terminus of a mature polypeptide; wherein the fragment has alpha-amylase activity. In one aspect, a fragment contains at least 481 amino acid residues, e.g., at least 483, at least 486, and at least 493 amino acid residues.

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$(\text{Identical Residues} \times 100)/(\text{Length of Alignment} - \text{Total Number of Gaps in Alignment})$$

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment)

Subsequence: The term "subsequence" means a polynucleotide sequence having one or more (several) nucleotides deleted from the 5' and/or 3' end of a mature polypeptide coding sequence; wherein the subsequence encodes a polypeptide fragment having alpha-amylase activity.

Variant: The term "variant" means a polypeptide having alpha-amylase activity comprising an alteration, i.e., a substitution, insertion, and/or deletion, of one or more (several) amino acid residues at one or more (several) positions. A substitution means a replacement of an amino acid occupying a position with a different amino acid; a deletion means removal of an amino acid occupying a position; and an insertion means adding amino acids, e.g., 1-5 amino acids, adjacent to and following an amino acid occupying a position.

Wild-Type: The term "wild-type" alpha-amylase denotes an alpha-amylase expressed by a naturally occurring microorganism, such as a bacterium, yeast or filamentous fungus found in nature.

Conventions for Designation of Variants

For purposes of the present invention, unless indicated otherwise, the hybrid polypeptide disclosed in SEQ ID NO: 27 (which has the sequence of amino acids 1-104 of *Bacillus stearothermophilus* alpha-amylase (SEQ ID NO: 4), followed by amino acids 103-208 of *Bacillus circulans* alpha-amylase (SEQ ID NO: 13), followed by amino acids 211-515 of *Bacillus stearothermophilus* alpha-amylase (SEQ ID NO: 4)) is used to determine the corresponding amino acid residue in another alpha-amylase. The amino acid sequence of another alpha-amylase is aligned with the mature polypeptide disclosed in SEQ ID NO: 27, and based on the alignment, the amino acid position number corresponding to any amino acid residue in the mature polypeptide disclosed in SEQ ID NO: 27 can be determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later.

Identification of the corresponding amino acid residue in another alpha-amylase can be confirmed by an alignment of multiple polypeptide sequences using "ClustalW" (Larkin et al., 2007, *Bioinformatics* 23: 2947-2948).

When the other enzyme has diverged from the mature polypeptide of SEQ ID NO: 27 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more (several) representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Eng.* 11: 739-747), and implementations of these algorithms can additionally be utilized to query structure databases with a structure of interest in order to discover possible structural homologs (e.g., Holm and Park, 2000, *Bioinformatics* 16: 566-567). These structural alignments can be used to predict the structurally and functionally corresponding amino acid residues in proteins within the same structural superfamily. This information, along with information derived from homology modeling and profile searches, can be used to predict which residues to mutate when moving mutations of interest from one protein to a close or remote homolog.

In describing the alpha-amylase variants of the present invention, the nomenclature described below is adapted for ease of reference. In all cases, the accepted IUPAC single letter or triple letter amino acid abbreviation is employed.

Substitutions.

For an amino acid substitution, the following nomenclature is used: original amino acid, position, substituted amino acid. Accordingly, the substitution of threonine with alanine at position 226 is designated as "Thr226Ala" or "T226A". Multiple mutations are separated by addition marks ("+"), e.g., "Gly205Arg+Ser411Phe" or "G205R+S411F", represents a substitution of glycine (G) with arginine (R) and of serine (S) with phenylalanine (F) at positions 205 and 411, respectively.

Deletions.

For an amino acid deletion, the following nomenclature is used: original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions.

For an amino acid insertion, the following nomenclature is used: original amino acid, position, original amino acid, new inserted amino acid. Accordingly the insertion of lysine after glycine at position 195 is designated "Gly195GlyLys" or "G195GK". Multiple insertions of amino acids are designated [Original amino acid, position, original amino acid, new inserted amino acid #1, new inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example the sequence would thus be:

| Parent: | Variant: |
|---------|----------|
| 195     | 195 195a 195b |
| G       | G-K-A    |

Multiple Alterations.

Variants comprising multiple alterations are separated by addition marks ("+"), e.g., "Arg170Tyr+Gly195Glu" or "R170Y+G195E" representing a substitution of tyrosine and glutamic acid for arginine and glycine at positions 170 and 195, respectively.

Different Alterations.

Where different alterations can be introduced at a position, the different alterations are separated by a comma, e.g., "Arg170Tyr,Glu" represents a substitution of arginge with tyrosine or glutamic acid at position 170. Thus, "Tyr167Gly,Ala+Arg170Gly,Ala" designates the following variants: Tyr167Gly+Arg170Gly, Tyr167Gly+Arg170Ala, Tyr167Ala+Arg170Gly, and Tyr167Ala+Arg170Ala.

Alpha-Amylases

The alpha-amylases of the present invention comprise an A-domain of a calcium-sensitive alpha-amylase, a B-domain of a calcium-insensitive alpha-amylase, and a C-domain of a calcium-sensitive alpha-amylase. The parent alpha-amylase may further comprise a carbohydrate-binding module.

Calcium-Sensitive Alpha-Amylases

Examples of calcium-sensitive alpha-amylases include the following alpha-amylases:

1. *Bacillus amyloliquefaciens* alpha-amylase having the amino acid sequence of SEQ ID NO: 1;
2. *Bacillus flavothermus* amylase, AMY1048 described in WO 2005/001064, having the amino acid sequence of SEQ ID NO: 2;
3. *Bacillus licheniformis* alpha-amylase having the amino acid sequence of SEQ ID NO: 3,
4. *Bacillus stearothermophilus* alpha-amylase having the amino acid sequence of SEQ ID NO: 4;
5. Alpha-amylase AA560 derived from *Bacillus* sp. DSM 12649 described in WO 00/60060, having the amino acid sequence of SEQ ID NO: 5;
6. Alpha-amylase derived from *Bacillus* sp. strain NCIB 12512 described in WO 95/26397, having the amino acid sequence of SEQ ID NO: 6;
7. Alpha-amylase derived from *Bacillus* sp. strain NCIB 12513 described in WO 95/26397, having the amino acid sequence of SEQ ID NO: 7;
8. Alpha-amylase SP707 described by Tsukamoto et al., 1988, *Biochem. Biophys. Res. Comm.* 151: 25-31, having the amino acid sequence of SEQ ID NO: 8;
9. Alpha-amylase TS-22 having the amino acid sequence of SEQ ID NO: 9;
10. Alpha-amylase TS-23 described in *J. Appl. Microbiology,* 1997, 82: 325-334 (SWALL:q59222), having the amino acid sequence of SEQ ID NO: 10;
11. Alpha-amylase derived from *Bacillus* sp. KSM-AP1378 (FERM BP-3048) described in WO 97/00324, having the amino acid sequence of SEQ ID NO: 11;
12. Alpha-amylase derived from *Bacillus* sp. A 7-7 described in WO 02/10356, having the amino acid sequence of SEQ ID NO: 12;
13. Alpha-amylase derived from *Bacillus stearothermophilus* (Spezyme Xtra), having the amino acid sequence of SEQ ID NO: 29.
14. Cytophaga alpha-amylase described in Jeang et al., 2002, *Appl. Environ. Microbiol.* 68:3651-3654, having the amino acid sequence of SEQ ID NO: 30; as well as hybrids and variants of any of these calcium-sensitive alpha-amylases.

Other calcium-sensitive alpha-amylases include the alpha-amylase produced by the *B. licheniformis* strain described in EP 0252666 (ATCC 27811) and the alpha-amylases disclosed in WO 91/00353 and WO 94/18314.

The calcium-sensitive alpha-amylase may be a hybrid of two or more calcium-sensitive alpha-amylases, such as a hybrid between *Bacillus amyloliquefaciens* alpha-amylase and *Bacillus licheniformis* alpha-amylase.

Commercially-available calcium-sensitive alpha-amylases are the products sold under the following tradenames: Optitherm™ and Takatherm™ (available from Danisco); Maxamyl™ (available from Danisco), Spezym AA™, Spezyme Delta AA™, Spezyme Fred and Spezyme Xtra (available from Danisco), and Keistase™ (available from Daiwa), PURASTAR™ ST 5000E, and PURASTAR™ HPAM L (from Genencor Int.).

The A-, B-, C-, and carbohydrate binding domains of these calcium-sensitive alpha-amylases are provided in the following table:

| Alpha-Amylase | A-Domain (A1 and A2 Domains) | B-Domain | C-Domain | C-terminal extension or Carbohydrate Binding Module |
|---|---|---|---|---|
| *Bacillus amyloliquefaciens* (SEQ ID NO: 1) | 1-101 + 208-396 | 102-207 | 397-483 | |
| *Bacillus flavothermus* (SEQ ID NO: 2) | 1-105 + 212-398 | 106-211 | 399-484 | 485-586 |
| *Bacillus licheniformis* (SEQ ID NO: 3) | 1-103 + 208-396 | 104-207 | 397-483 | |
| *Bacillus stearothermophilus* (SEQ ID NO: 4) | 1-104 + 211-396 | 105-210 | 397-483 | 484-515 |
| *Bacillus* sp. (SEQ ID NO: 5) | 1-105 + 213-398 | 106-212 | 399-485 | |
| *Bacillus* sp. NCIB 12512 (SEQ ID NO: 6) | 1-105 + 213-398 | 106-212 | 399-485 | |
| *Bacillus* sp. NCIB 12513 (SEQ ID NO: 7) | 1-105 + 213-398 | 106-212 | 399-485 | |

| Alpha-Amylase | A-Domain (A1 and A2 Domains) | B-Domain | C-Domain | C-terminal extension or Carbohydrate Binding Module |
|---|---|---|---|---|
| SP707 (SEQ ID NO: 8) | 1-105 + 213-398 | 106-212 | 399-485 | |
| TS-22 (SEQ ID NO: 9) | 1-105 + 213-398 | 106-212 | 399-484 | 485-586 |
| TS-23 (SEQ ID NO: 10) | 1-105 + 213-398 | 106-212 | 399-484 | 485-583 |
| *Bacillus* sp. KSM-AP1378 (SEQ ID NO: 11) | 1-105 + 213-398 | 106-212 | 399-485 | |
| *Bacillus* sp. SP7-7 (SEQ ID NO: 12) | 1-105 + 213-398 | 106-212 | 399-485 | |
| *Bacillus stearothermophilus* alpha-amylase (Spezyme Xtra, SEQ ID NO: 29) | 1-104 + 211-396 | 105-210 | 397-483 | 484-486 |
| *Cytophaga* alpha-amylase (SEQ ID NO: 30) | 1-102 + 209-397 | 103-208 | 398-484 | |

Calcium-Insensitive Alpha-Amylases

Examples of calcium-insensitive alpha-amylases include the following:
1. *Bacillus circulans* alpha-amylase having the sequence shown in SEQ ID NO: 13;
2. KSM K-36 alpha-amylase having the sequence disclosed in SEQ ID NO: 14;
3. KSM K-38 alpha-amylase having the sequence disclosed in SEQ ID NO: 15;
4. *Pyrococcus woesei* alpha-amylase having the amino acid sequence of SEQ ID NO: 16;
5. *Pyrococcus hybrid* alpha-amylase described in WO 03/083054 having the amino acid sequence of SEQ ID NO: 31;
as well as hybrids and variants of any of these alpha-amylases.

The A-, B-, C-, and carbohydrate binding domains of these calcium-insensitive alpha-amylases are provided in the following table:

| Alpha-Amylase | A-Domain (A1 and A2 Domains) | B-Domain | C-Domain | C-terminal extension or Carbohydrate Binding Module |
|---|---|---|---|---|
| *Bacillus circulans* (SEQ ID NO: 13) | 1-102 + 209-395 | 103-208 | 396-482 | 483-492 |
| KSM K-36 (SEQ ID NO: 14) | 1-103 + 208-393 | 104-207 | 394-480 | |
| KSM K-38 (SEQ ID NO: 15) | 1-103 + 208-393 | 104-207 | 394-480 | |
| *Pyrococcus woesei* (SEQ ID NO: 16) | 1-109 + 172-338 | 110-171 | 339-435 | |
| *Pyrococcus* hybrid alpha-amylase (SEQ ID NO: 31) | 1-109 + 172-338 | 110-171 | 339-435 | |

Alpha-Amylases of the Invention

The alpha-amylases of the present invention comprise an A-domain of a calcium-sensitive alpha-amylase, a B-domain of a calcium-insensitive alpha-amylase, and a C-domain of a calcium-sensitive alpha-amylase.

In an embodiment, the A-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the A-domain of SEQ ID NO: 1.

In an embodiment, the A-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the A-domain of SEQ ID NO: 2.

In an embodiment, the A-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the A-domain of SEQ ID NO: 3.

In an embodiment, the A-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the A-domain of SEQ ID NO: 4.

In an embodiment, the A-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the A-domain of SEQ ID NO: 5.

In an embodiment, the A-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the A-domain of SEQ ID NO: 6.

In an embodiment, the A-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the A-domain of SEQ ID NO: 7.

In an embodiment, the A-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the A-domain of SEQ ID NO: 8.

In an embodiment, the A-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the A-domain of SEQ ID NO: 9.

In an embodiment, the A-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the A-domain of SEQ ID NO: 10.

In an embodiment, the A-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the A-domain of SEQ ID NO: 11.

In an embodiment, the A-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the A-domain of SEQ ID NO: 12.

In an embodiment, the A-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the A-domain of SEQ ID NO: 29.

In an embodiment, the A-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the A-domain of SEQ ID NO: 30.

In an embodiment, the B-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the B-domain of SEQ ID NO: 13.

In an embodiment, the B-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the B-domain of SEQ ID NO: 14.

In an embodiment, the B-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the B-domain of SEQ ID NO: 15.

In an embodiment, the B-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the B-domain of SEQ ID NO: 16.

In an embodiment, the B-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the B-domain of SEQ ID NO: 31.

In an embodiment, the C-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the C-domain of SEQ ID NO: 1.

In an embodiment, the C-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the C-domain of SEQ ID NO: 2.

In an embodiment, the C-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the C-domain of SEQ ID NO: 3.

In an embodiment, the C-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the C-domain of SEQ ID NO: 4.

In an embodiment, the C-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the C-domain of SEQ ID NO: 5.

In an embodiment, the C-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the C-domain of SEQ ID NO: 6.

In an embodiment, the C-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the C-domain of SEQ ID NO: 7.

In an embodiment, the C-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the C-domain of SEQ ID NO: 8.

In an embodiment, the C-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the C-domain of SEQ ID NO: 9.

In an embodiment, the C-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the C-domain of SEQ ID NO: 10.

In an embodiment, the C-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the C-domain of SEQ ID NO: 11.

In an embodiment, the C-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the C-domain of SEQ ID NO: 12.

In an embodiment, the C-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the C-domain of SEQ ID NO: 29.

In an embodiment, the C-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the C-domain of SEQ ID NO: 30.

The alpha-amylases may be produced by substituting the B-domain or a portion thereof of a calcium-sensitive alpha-amylase with the B-domain or a portion thereof of a calcium-insensitive alpha-amylase. The alpha-amylases also may be produced by substituting the A- and C-domains or a portion thereof of a calcium-insensitive alpha-amylase with the A- and C-domains or a portion thereof of a calcium-sensitive alpha-amylase. When producing a hybrid alpha-amylase, no amino acids should be deleted or inserted in the two splicing sites, i.e., the two sites where the sequence of the calcium-sensitive alpha-amylase is combined with the sequence of the calcium-insensitive alpha-amylase.

The boundaries of the A-, B- and C-domains of calcium-sensitive and calcium-insensitive amylases provided in the tables above are flexible, and some liberty regarding the sequences is permitted. Thus, in general it is possible to deviate from the exact boundaries for the domains by up to 20 amino acids, e.g., less than 20 amino acids, less than 10 amino acids, less than 6 amino acids, and less than 3 amino acids. In other words, the sequence of the calcium-sensitive alpha-amylase to be replaced with the sequence of a calcium-insensitive alpha-amylase may be within 20 amino acids of the boundaries of the B-domain, e.g., less than 10 amino acids, within 6 amino acids, and within 3 amino acids. For example, the boundaries differ by one amino acid, two amino acids, three amino acids, four amino acids, five amino acids, six amino acids, seven amino acids, eight amino acids, nine amino acids, or ten amino acids.

For example, for the *B. amyloliquefaciens* alpha-amylase (SEQ ID NO: 1) where the B-domain has been determined as amino acid residues 102-207, the sequence to be replaced by the corresponding sequence of a calcium-insensitive alpha-amylase starts at a position in the range of positions 92-112 and ending at a position in the range of positions 197-217, e.g., starting at a position in the range of positions 96-108 and ending at a position in the range of positions 198-213 or starting at a position in the range of positions 99-105 and ending at a position in the range of positions 204-210. The A and C-domains of the *B. amyloliquefaciens* alpha-amylase were determined to be amino acid residues 1-101 (A1)+208-396 (A2) and 397-483, respectively. The alpha-amylases of the present invention may comprise an A1-domain starting at a position in the range of positions 1-5 and ending a position in the range of positions 91-111, e.g., starting at a position in the range of positions 1-3 and ending at a position in the range of positions 96-101 or starting at a position in the range of positions 1-3 and ending at a position in the range of positions 101-106. The alpha-amylases of the present invention may comprise A2 and C-domains starting at a position in the range of positions 198-218 and ending at a position in the range of positions 478-483, e.g., starting at a position in the range of positions 203-208 and ending at a position in the range of positions 480-483 or starting at a position in the range of positions 208-213 and ending at a position in the range of positions 480-483.

For the *B. flavothermus* alpha-amylase (SEQ ID NO: 2) where the B-domain has been determined as amino acid residues 106-211, the sequence to be replaced by the corresponding sequence of a calcium-insensitive alpha-amylase starts at a position in the range of positions 96-116 and ending at a position in the range of positions 198-218, e.g., starting at a position in the range of positions 100-112 and ending at a position in the range of positions 202-214 or starting at a position in the range of positions 103-109 and ending at a position in the range of positions 205-212. The A and C-domains of the *B. flavothermus* alpha-amylase were determined to be amino acid residues 1-105 (A1)+212-398 (A2) and 399-484, respectively. The alpha-amylases of the present invention may comprise an A1-domain starting at a position in the range of positions 1-5 and ending a position in the range of positions 95-115, e.g., starting at a position in the range of positions 1-3 and ending at a position in the range of positions 100-105 or starting at a position in the range of positions 1-3 and ending at a position in the range of positions 105-110. The alpha-amylases of the present invention may comprise A2 and C-domains starting at a position in the range of positions 202-222 and ending at a position in the range of positions 479-484, e.g., starting at a position in the range of positions 207-212 and ending at a position in the range of positions 481-484 or starting at a position in the range of positions 212-217 and ending at a position in the range of positions 481-484. The *B. flavothermus* alpha-amylase further has a carbohydrate binding domain of amino acid residues 485-586. The carbohydrate binding domain is not required for the amylase activity and might be fully or partially deleted.

For the *B. licheniformis* alpha-amylase (SEQ ID NO: 3) where the B-domain has been determined as amino acid residues 104-207, the sequence of *B. licheniformis* alpha-amylase to be replaced by the corresponding sequence of a calcium-insensitive alpha-amylase starts at a position in the range of positions 94-114 and ending at a position in the range of positions 194-214, e.g., starting at a position in the range of positions 98-110 and ending at a position in the range of positions 198-210 or starting at a position in the range of positions 101-107 and ending at a position in the range of positions 201-207. The A and C-domains of the *B. licheniformis* alpha-amylase were determined to be amino acid residues 1-103 (A1)+208-396 (A2) and 397-483, respectively. The alpha-amylases of the present invention may comprise an A1-domain starting at a position in the range of positions 1-5 and ending a position in the range of positions 93-113, e.g., starting at a position in the range of positions 1-3 and ending at a position in the range of positions 98-103 or starting at a position in the range of positions 1-3 and ending at a position in the range of positions 103-108. The alpha-amylases of the present invention may comprise A2 and C-domains starting at a position in the range of positions 198-218 and ending at a position in the range of positions 478-483, e.g., starting at a position in the range of positions 203-208 and ending at a position in the range of positions 480-483 or starting at a position in the range of positions 208-213 and ending at a position in the range of positions 480-483.

For the *B. stearothermophilus* alpha-amylase (SEQ ID NO: 4) where the B-domain has been determined as amino acid residues 105-210, the sequence to be replaced by the corresponding sequence of a calcium-insensitive alpha-amylase starts at a position in the range of positions 95-115 and ending at a position in the range of positions 197-213, e.g., starting at a position in the range of positions 99-111 and ending at a position in the range of positions 201-213 or starting at a position in the range of positions 102-108 and ending at a position in the range of positions 204-210. The A and C-domains of the *B. stearothermophilus* alpha-amylase were determined to be amino acid residues 1-104 (A1)+211-396 (A2) and 397-483, respectively. The alpha-amylases of the present invention may comprise an A1-domain starting at a position in the range of positions 1-5 and ending a position in the range of positions 94-114, e.g., starting at a position in the range of positions 1-3 and ending at a position in the range of positions 99-104 or starting at a position in the range of positions 1-3 and ending at a position in the range of positions 104-109. The alpha-amylases of the present invention may comprise A2 and C-domains starting at a position in the range of positions 201-221 and ending at a position in the range of positions 478-483, e.g., starting at a position in the range of positions 206-211 and ending at a position in the range of positions 480-483 or starting at a position in the range of positions 211-216 and ending at a position in the range of positions 480-483. The *B. stearothermophilus* alpha-amylase further has a C-terminal extension of amino acid residues 484-586. The C-terminal extension is not required for the amylase activity and might be fully or partially deleted.

For the *Bacillus* alpha-amylase (SEQ ID NO: 5) where the B-domain has been determined as amino acid residues 106-212, the sequence to be replaced by the corresponding sequence of a calcium-insensitive alpha-amylase starts at a position in the range of positions 96-116 and ending at a position in the range of positions 199-219, e.g., starting at a position in the range of positions 100-112 and ending at a position in the range of positions 203-215 or starting at a position in the range of positions 103-109 and ending at a position in the range of positions 206-212. The A and C-domains of the *Bacillus* alpha-amylase were determined to be amino acid residues 1-105 (A1)+213-396 (A2) and 399-485, respectively. The alpha-amylases of the present invention may comprise an A1-domain starting at a position in the range of positions 1-5 and ending a position in the range of positions 95-115, e.g., starting at a position in the range of positions 1-3 and ending at a position in the range of positions 100-105 or starting at a position in the range of positions 1-3 and ending at a position in the range of positions 105-110. The alpha-amylases of the present invention may comprise A2 and C-domains starting at a position in the range of positions 203-223 and ending at a position in the range of positions 482-485, e.g., starting at a position in the range of positions 208-213 and ending at a position in the range of positions 482-485 or starting at a position in the range of positions 213-218 and ending at a position in the range of positions 482-485.

For the *Bacillus* alpha-amylase (SEQ ID NO: 6) where the B-domain has been determined as amino acid residues 106-212, the sequence to be replaced by the corresponding sequence of a calcium-insensitive alpha-amylase starts at a position in the range of positions 96-116 and ending at a position in the range of positions 199-219, e.g., starting at a position in the range of positions 100-112 and ending at a position in the range of positions 203-215 or starting at a position in the range of positions 103-109 and ending at a position in the range of positions 206-212. The A and C-domains of the *Bacillus* alpha-amylase were determined to be amino acid residues 1-105 (A1)+213-398 (A2) and 399-485, respectively. The alpha-amylases of the present invention may comprise an A1-domain starting at a position in the range of positions 1-5 and ending a position in the range of positions 95-115, e.g., starting at a position in the range of positions 1-3 and ending at a position in the range of positions 100-105 or starting at a position in the range of positions 1-3 and ending at a position in the range of positions 105-110. The alpha-amylases of the present invention may comprise A2 and C-domains starting at a position in the range of positions 203-223 and ending at a position in the range of positions 482-485, e.g., starting at a position in the range of positions 208-213 and ending at a position in the range of positions 482-485 or starting at a position in the range of positions 213-218 and ending at a position in the range of positions 482-485.

For the *Bacillus* alpha-amylase (SEQ ID NO: 7) where the B-domain has been determined as amino acid residues 106-212, the sequence to be replaced by the corresponding sequence of a calcium-insensitive alpha-amylase starts at a position in the range of positions 96-116 and ending at a position in the range of positions 199-219, e.g., starting at a position in the range of positions 100-112 and ending at a position in the range of positions 203-215 or starting at a position in the range of positions 103-109 and ending at a position in the range of positions 206-212. The A and C-domains of the *Bacillus* alpha-amylase were determined to be amino acid residues 1-105 (A1)+213-398 (A2) and 399-485, respectively. The alpha-amylases of the present invention may comprise an A1-domain starting at a position in the range of positions 1-5 and ending a position in the range of positions 95-115, e.g., starting at a position in the range of positions 1-3 and ending at a position in the range of positions 100-105 or starting at a position in the range of positions 1-3 and ending at a position in the range of positions 105-110. The alpha-amylases of the present invention may comprise A2 and C-domains starting at a position in the range of positions 203-223 and ending at a position in the range of positions 482-485, e.g., starting at a position in the range of positions 208-213 and ending at a position in the range of positions 482-485 or starting at a position in the range of positions 213-218 and ending at a position in the range of positions 482-485.

For the SP707 alpha-amylase (SEQ ID NO: 8) where the B-domain has been determined as amino acid residues 106-212, the sequence to be replaced by the corresponding sequence of a calcium-insensitive alpha-amylase starts at a position in the range of positions 96-116 and ending at a position in the range of positions 199-219, e.g., starting at a position in the range of positions 100-112 and ending at a position in the range of positions 203-215 or starting at a position in the range of positions 103-109 and ending at a position in the range of positions 206-212. The A and C-domains of the SP707 alpha-amylase were determined to be amino acid residues 1-105 (A1)+213-398 (A2) and 399-485, respectively. The alpha-amylases of the present invention may comprise an A1-domain starting at a position in the range of positions 1-5 and ending a position in the range of positions 95-115, e.g., starting at a position in the range of positions 1-3 and ending at a position in the range of positions 100-105 or starting at a position in the range of positions 1-3 and ending at a position in the range of positions 105-110. The alpha-amylases of the present invention may comprise A2 and C-domains starting at a position in the range of positions 203-223 and ending at a position in the range of positions 482-485, e.g., starting at a position in the range of positions 208-213 and ending at a position in the range of positions 482-485 or starting at a position in the range of positions 213-218 and ending at a position in the range of positions 482-485.

For the TS-22 alpha-amylase (SEQ ID NO: 9) where the B-domain has been determined as amino acid residues 106-212, the sequence to be replaced by the corresponding sequence of a calcium-insensitive alpha-amylase starts at a position in the range of positions 96-116 and ending at a position in the range of positions 199-219, e.g., starting at a position in the range of positions 100-112 and ending at a position in the range of positions 203-215 or starting at a position in the range of positions 103-109 and ending at a position in the range of positions 206-212. The A and C-domains of the TS-22 alpha-amylase were determined to be amino acid residues 1-105 (A1)+213-398 (A2) and 399-484, respectively. The alpha-amylases of the present invention may comprise an A1-domain starting at a position in the range of positions 1-5 and ending a position in the range of positions 95-115, e.g., starting at a position in the range of positions 1-3 and ending at a position in the range of positions 100-105 or starting at a position in the range of positions 1-3 and ending at a position in the range of positions 105-110. The alpha-amylases of the present invention may comprise A2 and C-domains starting at a position in the range of positions 203-223 and ending at a position in the range of positions 481-484, e.g., starting at a position in the range of positions 208-213 and ending at a position in the range of positions 482-484 or starting at a position in the range of positions 213-218 and ending at a position in the range of positions 482-484. The TS-22 alpha-amylase further has a carbohydrate binding domain of amino acid residues 485-586. The carbohydrate binding domain is not required for the amylase activity and might be fully or partially deleted.

For the TS-23 alpha-amylase (SEQ ID NO: 10) where the B-domain has been determined as amino acid residues 106-212, the sequence to be replaced by the corresponding sequence of a calcium-insensitive alpha-amylase starts at a position in the range of positions 96-116 and ending at a position in the range of positions 199-219, e.g., starting at a position in the range of positions 100-112 and ending at a position in the range of positions 203-215 or starting at a position in the range of positions 103-109 and ending at a position in the range of positions 206-212. The A and C-domains of the TS-23 alpha-amylase were determined to be amino acid residues 1-105 (A1)+213-398 (A2) and 399-484, respectively. The alpha-amylases of the present invention may comprise an A1-domain starting at a position in the range of positions 1-5 and ending a position in the range of positions 95-115, e.g., starting at a position in the range of positions 1-3 and ending at a position in the range of positions 100-105 or starting at a position in the range of positions 1-3 and ending at a position in the range of positions 105-110. The alpha-amylases of the present invention may comprise A2 and C-domains starting at a position in the range of positions 203-223 and ending at a position in the range of positions 482-484, e.g., starting at a position in the range of positions 208-213 and ending at a position in the range of positions 482-484 or starting at a position in the range of positions 213-218 and ending at a position in the range of positions 482-484. The TS-23 alpha-amylase further has a carbohydrate binding domain of amino acid residues 485-583. The carbohydrate binding domain is not required for the amylase activity and might be fully or partially deleted.

For the KSM-AP1378 alpha-amylase (SEQ ID NO: 11) where the B-domain has been determined as amino acid residues 106-212, the sequence to be replaced by the corresponding sequence of a calcium-insensitive alpha-amylase starts at a position in the range of positions 96-116 and ending at a position in the range of positions 199-219, e.g., starting at a position in the range of positions 100-112 and ending at a position in the range of positions 203-215 or starting at a position in the range of positions 103-109 and ending at a position in the range of positions 206-212. The A and C-domains of the KSM-AP1378 alpha-amylase were determined to be amino acid residues 1-105 (A1)+213-398 (A2) and 399-485, respectively. The alpha-amylases of the present invention may comprise an A1-domain starting at a position in the range of positions 1-5 and ending a position in the range of positions 95-115, e.g., starting at a position in the range of positions 1-3 and ending at a position in the range of positions 100-105 or starting at a position in the range of positions 1-3 and ending at a position in the range of positions 105-110. The alpha-amylases of the present invention may comprise A2 and C-domains starting at a position in the range of positions 203-223 and ending at a position in the range of positions 482-485, e.g., starting at a position in the range of positions 208-213 and ending at a position in the range of positions 482-485 or starting at a position in the range of positions 213-218 and ending at a position in the range of positions 482-485.

For the *Bacillus* SP7-7 alpha-amylase (SEQ ID NO: 12) where the B-domain has been determined as amino acid residues 106-212, the sequence to be replaced by the corresponding sequence of a calcium-insensitive alpha-amylase starts at a position in the range of positions 96-116 and ending at a position in the range of positions 199-219, e.g., starting at a position in the range of positions 100-112 and ending at a position in the range of positions 203-215 or starting at a position in the range of positions 103-109 and ending at a position in the range of positions 206-212. The A and C-domains of the *Bacillus* SP7-7 alpha-amylase were determined to be amino acid residues 1-105 (A1)+213-398 (A2) and 399-485, respectively. The alpha-amylases of the present invention may comprise an A1-domain starting at a position in the range of positions 1-5 and ending a position in the range of positions 95-115, e.g., starting at a position in the range of positions 1-3 and ending at a position in the range of positions 100-105 or starting at a position in the range of positions 1-3 and ending at a position in the range of positions 105-110. The alpha-amylases of the present invention may comprise A2 and C-domains starting at a position in the range of positions 203-223 and ending at a position in the range of positions 482-485, e.g., starting at a position in the range of positions 208-213 and ending at a position in the range of positions 482-485 or starting at a position in the range of positions 213-218 and ending at a position in the range of positions 482-485.

For the *B. stearothermophilus* alpha-amylase (SEQ ID NO: 29) where the B-domain has been determined as amino acid residues 105-210, the sequence to be replaced by the corresponding sequence of a calcium-insensitive alpha-amylase starts at a position in the range of positions 95-115 and ending at a position in the range of positions 197-213, e.g., starting at a position in the range of positions 99-111 and ending at a position in the range of positions 201-213 or starting at a position in the range of positions 102-108 and ending at a position in the range of positions 204-210. The A and C-domains of the *B. stearothermophilus* alpha-amylase were determined to be amino acid residues 1-104 (A1)+211-396 (A2) and 397-483, respectively. The alpha-amylases of the present invention may comprise an A1-domain starting at a position in the range of positions 1-5 and ending a position in the range of positions 94-114, e.g., starting at a position in the range of positions 1-3 and ending at a position in the range of positions 99-104 or starting at a position in the range of positions 1-3 and ending at a position in the range of positions 104-109. The alpha-amylases of the present invention may comprise A2 and C-domains starting at a position in the range of positions 201-221 and ending at a position in the range of positions 478-483, e.g., starting at a position in the range of positions 206-211 and ending at a position in the range of positions 480-483 or starting at a position in the range of positions 211-216 and ending at a position in the range of positions 480-483. The *B. stearothermophilus* alpha-amylase further has a C-terminal extension of amino acid residues 484-486. The C-terminal extension is not required for the amylase activity and might be fully or partially deleted.

For the Cytophagus alpha-amylase (SEQ ID NO: 30) where the B-domain has been determined as amino acid residues 103-208, the sequence to be replaced by the corresponding sequence of a calcium-insensitive alpha-amylase starts at a position in the range of positions 93-113 and ending at a position in the range of positions 195-215, e.g., starting at a position in the range of positions 97-109 and ending at a position in the range of positions 199-211 or starting at a position in the range of positions 100-106 and ending at a position in the range of positions 202-208. The A and C-domains of the Cytophagus alpha-amylase were determined to be amino acid residues 1-102 (A1)+209-397 (A2) and 398-484, respectively. The alpha-amylases of the present invention may comprise an A1-domain starting at a position in the range of positions 1-5 and ending a position in the range of positions 92-112, e.g., starting at a position in the range of positions 1-3 and ending at a position in the range of positions 97-102 or starting at a position in the range of positions 1-3 and ending at a position in the range of positions 102-107. The alpha-amylases of the present invention may comprise A2 and C-domains starting at a position in the range of positions 199-219 and ending at a position in the range of positions 479-484, e.g., starting at a position in the range of positions 204-209 and ending at a position in the range of positions 481-484 or starting at a position in the range of positions 209-214 and ending at a position in the range of positions 481-484.

For the *Bacillus circulans* alpha-amylase (SEQ ID NO: 13), the B-domain has been determined as amino acid residues 103-208. The alpha-amylases of the present invention may comprise a B-domain starting at a position in the range of positions 93-113 and ending at a position in the range of positions 195-215, e.g., starting at a position in the range of positions 97-109 and ending at a position in the range of positions 199-211 or starting at a position in the range of positions 100-106 and ending at a position in the range of positions 202-208. The A and C-domains of the *Bacillus circulans* alpha-amylase were determined to be amino acid residues 1-102 (A1)+209-395 (A2) and 396-482, respectively. The A1-domain which can be replaced by the corresponding sequence of a calcium-sensitive alpha-amylase starts at a position in the range of positions 1-5 and ending at a position in the range of positions 92-112, e.g., starting at a position in the range of positions 1-3 and ending at a position in the range of positions 97-102 or starting at a position in the range of positions 1-3 and ending at a position in the range of positions 102-107. The A2-domain which can be replaced by the corresponding sequence of a calcium-sensitive alpha-amylase starts at a position in the range of positions 199-219 and ending at a position in the range of positions 385-405, e.g., starting at a position in the range of positions 204-209 and ending at a position in the range of positions 390-395 or starting at a position in the range of positions 209-214 and ending at a position in the range of positions 395-400. The A1 and A2 domains are preferably replaced simultaneously by the corresponding sequence of a calcium-sensitive alpha-amylase. The C-domain which can be replaced by the corresponding sequence of a calcium-sensitive alpha-amylase starts at a position in the range of positions 386-406 and ending at a position in the range of positions 477-482, e.g., starting at a position in the range of positions 391-396 and ending at a position in the range of positions 479-482 or starting at a position in the range of positions 396-401 and ending at a position in the range of positions 479-482. The *Bacillus circulans* alpha-amylase further has a C-terminal extension of amino acid residues 483-492. The extension is not required for the amylase activity and might be fully or partially deleted.

For the KSM-K36 alpha-amylase (SEQ ID NO: 14), the B-domain has been determined as amino acid residues 104-207. The alpha-amylases of the present invention may comprise a B-domain starting at a position in the range of positions 93-113 and ending at a position in the range of positions 195-215, e.g., starting at a position in the range of positions 97-109 and ending at a position in the range of positions 199-211 or starting at a position in the range of positions 100-106 and ending at a position in the range of positions 202-208. The A and C-domains of the *Bacillus circulans* alpha-amylase were determined to be amino acid residues 1-103 (A1)+208-393 (A2) and 394-480, respectively. The A1-domain which can be replaced by the corresponding sequence of a calcium-sensitive alpha-amylase starts at a position in the range of positions 1-5 and ending at a position in the range of positions 93-113, e.g., starting at a position in the range of positions 1-3 and ending at a position in the range of positions 98-103 or starting at a position in the range of positions 1-3 and ending at a position in the range of positions 103-108. The A2-domain which can be replaced by the corresponding sequence of a calcium-sensitive alpha-amylase starts at a position in the range of positions 198-218 and ending at a position in the range of positions 383-403, e.g., starting at a position in the range of positions 203-208 and ending at a position in the range of positions 388-393 or starting at a position in the range of positions 208-213 and ending at a position in the range of positions 393-398. The A1 and A2 domains are preferably replaced simultaneously by the corresponding sequence of a calcium-sensitive alpha-amylase. The C-domain which can be replaced by the corresponding sequence of a calcium-sensitive alpha-amylase starts at a position in the range of positions 384-404 and ending at a position in the range of positions 475-480, e.g., starting at a position in the range of positions 389-394 and ending at a position in the range of positions 477-480 or starting at a position in the range of positions 394-399 and ending at a position in the range of positions 477-480.

For the KSM-K38 alpha-amylase (SEQ ID NO: 15), the B-domain has been determined as amino acid residues 104-207. The alpha-amylases of the present invention may comprise a B-domain starting at a position in the range of positions 93-113 and ending at a position in the range of positions 195-215, e.g., starting at a position in the range of positions 97-109 and ending at a position in the range of positions 199-211 or starting at a position in the range of positions 100-106 and ending at a position in the range of positions 202-208. The A and C-domains of the *Bacillus circulans* alpha-amylase were determined to be amino acid residues 1-103 (A1)+208-393 (A2) and 394-480, respectively. The A1-domain which can be replaced by the corresponding sequence of a calcium-sensitive alpha-amylase starts at a position in the range of positions 1-5 and ending at a position in the range of positions 93-113, e.g., starting at a position in the range of positions 1-3 and ending at a position in the range of positions 98-103 or starting at a position in the range of positions 1-3 and ending at a position in the range of positions 103-108. The A2-domain which can be replaced by the corresponding sequence of a calcium-sensitive alpha-amylase starts at a position in the range of positions 198-218 and ending at a position in the range of positions 383-403, e.g., starting at a position in the range of positions 203-208 and ending at a position in the range of positions 388-393 or starting at a position in the range of positions 208-213 and ending at a position in the range of positions 393-398. The A1 and A2 domains are preferably replaced simultaneously by the corresponding sequence of a calcium-sensitive alpha-amylase. The C-domain which can be replaced by the corresponding sequence of a calcium-sensitive alpha-amylase starts at a position in the range of positions 384-404 and ending at a position in the range of positions 475-480, e.g., starting at a position in the range of positions 389-394 and ending at a position in the range of positions 477-480 or starting at a position in the range of positions 394-399 and ending at a position in the range of positions 477-480.

For the *Pyrococcus woesei* alpha-amylase (SEQ ID NO: 16), the B-domain has been determined as amino acid residues 110-171. The alpha-amylases of the present invention may comprise a B-domain starting at a position in the range of positions 100-120 and ending at a position in the range of positions 161-181, e.g., starting at a position in the range of positions 105-115 and ending at a position in the range of positions 166-171 or starting at a position in the range of positions 107-113 and ending at a position in the range of positions 171-176. The A and C-domains of the *Bacillus circulans* alpha-amylase were determined to be amino acid residues 1-109 (A1)+172-338 (A2) and 339-435, respectively. The A1-domain which can be replaced by the corresponding sequence of a calcium-sensitive alpha-amylase starts at a position in the range of positions 1-5 and ending at a position in the range of positions 99-119, e.g., starting at a position in the range of positions 1-3 and ending at a position in the range of positions 104-109 or starting at a position in the range of positions 1-3 and ending at a position in the range of positions 109-114. The A2-domain which can be replaced by the corresponding sequence of a calcium-sensitive alpha-amylase starts at a position in the range of positions 161-181 and ending at a position in the range of positions 328-348, e.g., starting at a position in the range of positions 167-172 and ending at a position in the range of positions 333-338 or starting at a position in the range of positions 172-177 and ending at a position in the range of positions 338-343. The A1 and A2 domains are preferably replaced simultaneously by the corresponding sequence of a calcium-sensitive alpha-amylase. The C-domain which can be replaced by the corresponding sequence of a calcium-sensitive alpha-amylase starts at a position in the range of positions 329-349 and ending at a position in the range of positions 430-435, e.g., starting at a position in the range of positions 324-329 and ending at a position in the range of positions 432-435 or starting at a position in the range of positions 329-344 and ending at a position in the range of positions 432-435.

For the *Pyrococcus* hybrid alpha-amylase (SEQ ID NO: 31), the B-domain has been determined as amino acid residues 110-171. The alpha-amylases of the present invention may comprise a B-domain starting at a position in the range of positions 100-120 and ending at a position in the range of positions 161-181, e.g., starting at a position in the range of positions 105-115 and ending at a position in the range of positions 166-171 or starting at a position in the range of positions 107-113 and ending at a position in the range of positions 171-176. The A and C-domains of the *Bacillus circulans* alpha-amylase were determined to be amino acid residues 1-109 (A1)+172-338 (A2) and 339-435, respectively. The A1-domain which can be replaced by the corresponding sequence of a calcium-sensitive alpha-amylase starts at a position in the range of positions 1-5 and ending at a position in the range of positions 99-119, e.g., starting at a position in the range of positions 1-3 and ending at a position in the range of positions 104-109 or starting at a position in the range of positions 1-3 and ending at a position in the range of positions 109-114. The A2-domain which can be replaced by the corresponding sequence of a calcium-sensitive alpha-amylase starts at a position in the range of positions 161-181 and ending at a position in the range of positions 328-348, e.g., starting at a position in the range of positions 167-172 and ending at a position in the range of positions 333-338 or starting at a position in the range of positions 172-177 and ending at a position in the range of positions 338-343. The A1 and A2 domains are preferably replaced simultaneously by the corresponding sequence of a calcium-sensitive alpha-amylase. The C-domain which can be replaced by the corresponding sequence of a calcium-sensitive alpha-amylase starts at a position in the range of positions 329-349 and ending at a position in the range of positions 430-435, e.g., starting at a position in the range of positions 334-339 and ending at a position in the range of positions 432-435 or starting at a position in the range of positions 339-344 and ending at a position in the range of positions 432-435.

In an embodiment, the alpha-amylase has a ratio of activity measured by the Phadebas activity to the activity measured by the G7-pNG assay greater than 0.1, preferably of more than 0.25, even more preferred more than 0.5 and most preferred more than 1.

The Phadebas assay is an assay for determining alpha-amylase activity using a cross-linked insoluble blue-colored starch polymer (Phadebas® Amylase Test, supplied by Magle Life Sciences, Lund, Sweden).

The G7-pNG assay is an assay for determining alpha-amylase activity using a soluble chromogen compound, p-nitrophenyl-alpha-D-maltoheptaoside. Kits containing PNP-G7 substrate and alpha-Glucosidase is manufactured by Boehringer-Mannheim (cat. no. 1054635).

In order to determine the alpha-amylase activity using the Phadebas and the G7-pNG assays, a reference amylase with known activity must be included in the assay and the activity is determined relative to the reference alpha-amylase. For purposes of the present invention, the reference alpha-amylase, which is considered to have the same activity when measured by the Phadebas and the G7-pNG assays, is the *Bacillus licheniformis* alpha-amylase sold by Novozymes A/S under the tradename Termamyl®, which has the sequence of SEQ ID NO: 3. Thus, the reference alpha-amylase has a ratio of 1 when measuring the activity by the Phadebas assay relative to the activity measured by the G7-pNP assay.

The ratio of activity on insoluble substrate to activity on soluble substrate is determined by measuring the activities on the two particular selected substrates and calculation of the ratio. Preferably the ratio is at least 1.5 fold higher than for the parent calcium-insensitive alpha-amylase, e.g., at least 2 fold higher, at least 2.5 fold higher and at least 3 fold higher.

Using the methods disclosed below for determining the ratio of activity by the Phadebas assay to the activity of the G7pNG assay, the *B. circulans* alpha-amylase having the amino acid sequence of SEQ ID NO: 13 was found to have a ratio of approximately 0.014.

The inventors have discovered that the calcium sensitivity to a significant degree can be assigned to the B-domain of an calcium-sensitive alpha-amylase and that it is possible to retain all or at least some of the beneficial good properties of a calcium-sensitive alpha-amylase by exchanging the complete B-domain or a part of the B-domain of said calcium-sensitive alpha-amylase with the B-domain or a part of the B-domain derived from a calcium-insensitive alpha-amylase. Preferably, the complete B-domain of a calcium-sensitive alpha-amylase is exchanged with the complete B-domain of a calcium-insensitive alpha-amylase.

The alpha-amylases of the present invention have the benefit of being less sensitive toward calcium depletion than their parent calcium-sensitive alpha-amylase but at the same time they maintain the performance properties of the parent calcium-sensitive alpha-amylase. Calcium sensitivity is manifested in the activity and/or stability of the particular alpha-amylase in calcium depleted environments and/or under acidic conditions. Calcium depleted environments occurs in many known applications of alpha-amylases, such as in the presence of strong chelators binding metal ions in particular calcium ions, e.g., in detergents where it is common to include strong chelators because of the beneficial effect of the laundering process, or in conditions where plant material including natural chelators such as phytates or citrates is present. Such strong chelators will compete with the calcium-sensitive alpha-amylases for the calcium ions and will to some extent be able to deprive the calcium-sensitive alpha-amylases for the calcium ions bound to their structure with the consequence that the stability or activity of the calcium-sensitive is reduced.

Acidic conditions also may affect the stability or activity of calcium-sensitive alpha-amylases. It is believed that low pH may lead to a protonation of the amino acid residues that coordinate the calcium ions in calcium-sensitive alpha-amylases with the result that they no longer are capable of binding the calcium and the result is a loss of stability and/or activity. An example of an application where alpha-amylases are exposed to acidic conditions is the use of alpha-amylases in the treatment of digestive disorders such as disclosed in WO 2006/136161 and the use in feed.

Thus, the alpha-amylases have improved stability and/or activity in the presence of strong chelators and/or improved stability and/or activity at low pH.

The alpha-amylases may further comprise additional substitutions, insertions or deletions known in the art to improve the properties of alpha-amylases.

For example, oxidizable amino acid residues may be substituted with a non-oxidizable amino acid residue in order to improve the stability of the enzyme under oxidizing conditions, e.g., in the presence of bleach, in accordance with the teachings of WO 94/02597 and WO 94/18314, which are incorporated herein by reference.

In addition, two amino acids in the region 179-182 (using SEQ ID NO: 27 numbering) may be deleted to improve stability/activity, as described in WO 96/23873, which is incorporated herein by reference. Two amino acids at corresponding positions in other alpha-amylases may be deleted.

Further beneficial substitutions that may be introduced are disclosed in WO 99/23211, WO 01/66712 and WO 2006/002643, which are incorporated herein by reference.

The alpha-amylases of the invention may further comprise additional substitutions, insertions or deletions in the B-domain derived from the calcium-insensitive alpha-amylase. Examples of suitable substitutions, insertions or deletions in the B-domain of a calcium-insensitive alpha-amylase are the alterations corresponding to the following alterations in *B. circulans* alpha-amylase: E179*, N180*, E185W, N186E and D189T (SEQ ID NO: 13 numbering), which correspond to E181*, N182*, E187W, N188E and D191T in SEQ ID NO: 27 numbering.

In another embodiment, the alpha-amylases of the present invention comprise the substitution Q150T.

In another embodiment, the alpha-amylases of the present invention comprise the substitution T164V.

In another embodiment, the alpha-amylases of the present invention comprise the substitution K184A.

In one embodiment the parent calcium-sensitive alpha-amylase is the alpha-amylase having the amino acid sequence of SEQ ID NO: 7, which has good performance in detergents. The B-domain of this calcium-sensitive alpha-amylase may for example be replaced with the B-domain from the calcium insensitive alpha-amylase of SEQ ID NO: 13. The hybrid may further comprise one or more of the following alterations: E183*, N184*, E189W, N190E, and D193T (SEQ ID NO: 7 numbering), which correspond to E181*, N182*, E187W, N188E, and D191T in SEQ ID NO: 27 numbering. These hybrids show good performance in detergents and have improved stability in the presence of strong chelators.

In another embodiment the calcium-sensitive alpha-amylase is the *B. stearothermophilus* alpha-amylase of SEQ ID NO: 4, which has outstanding properties for liquefaction of starches. The B-domain of this alpha-amylase may for example be replaced with the B-domain from *B. circulans* of SEQ ID NO: 13, e.g., the amino acid residues at positions 104-209 in SEQ ID NO: 4 may be replaced with the amino acids at positions 103-208 in SEQ ID NO: 13. The hybrid may optionally comprise one or more of the following modifications: E181*, G182*, E187W, N188E, D191T, S299K, G301R, A302D, D405N, D428N, and P430D (SEQ ID NO: 27 numbering).

Other examples of alpha-amylases of the present invention include:

A hybrid where the B-domain of a variant of SEQ ID NO: 5 having the alterations D183*+G184*+R118K+N195F+R320K+R458K (SEQ ID NO: 5 numbering) disclosed in WO 01/66712 is replaced with the B-domain of SEQ ID NO: 13, SEQ ID NO: 14 or SEQ ID NO: 15. For example, amino acids 107-204 of SEQ ID NO: 14 may replace amino acids 109-208 of said variant of SEQ ID NO: 5. In another example, amino acids 104-209 of SEQ ID NO: 15 may replace amino acids 106-213 of said variant of SEQ ID NO: 5.

A hybrid where part of the B-domain of a variant of SEQ ID NO: 5 having the alterations D183*+G184*+R118K+N195F+R320K+R458K (SEQ ID NO: 5 numbering) disclosed in WO 01/66712 is replaced with the B-domain of SEQ ID NO: 14. For example, amino acids 158-204 of SEQ ID NO: 14 may replace amino acids 160-208 of said variant of SEQ ID NO: 5.

A hybrid where the B-domain of the hybrid mutant alpha-amylase LE399, which has the amino acid sequence of SEQ ID NO: 2 in WO 06/066594 and the substitutions G46A+T47I+G105A (SEQ ID NO: 3 numbering), is replaced with the B-domain of SEQ ID NO: 13. For example, amino acids 107-205 of SEQ ID NO: 13 may replace amino acids 106-202 of LE399.

A hybrid where the B-domain of a variant of SEQ ID NO: 5 having the mutations M9L+K118R+G149A+G182T+D183*+G184*+G186A+N195F+M202L+T257I+Y295F+N299Y+R320K+M323T+A339S+E345R+R458K (SEQ ID NO: 5 numbering) disclosed in WO 06/002643 is replaced with the B-domain of SEQ ID NO: 13.

A hybrid where the B-domain of SP707 alpha-amylase of SEQ ID NO: 8 is replaced with the B-domain of SEQ ID NO: 13.

Polynucleotides

The present invention also relates to isolated polynucleotides encoding a polypeptide of the present invention.

Nucleic Acid Constructs

The present invention also relates to nucleic acid constructs comprising a polynucleotide of the present invention operably linked to one or more (several) control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter sequence, a polynucleotide that is recognized by a host cell for expression of a polynucleotide encoding a polypeptide of the present invention. The promoter sequence contains transcriptional control sequences that mediate the expression of the polypeptide. The promoter may be any polynucleotide that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *E. coli* lac operon, *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American*, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dada (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter including a gene encoding a neutral alpha-amylase in *Aspergilli* in which the untranslated leader has been replaced by an untranslated leader from a gene encoding triose phosphate isomerase in *Aspergilli*; non-limiting examples include modified promoters including the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, which is recognized by a host cell to terminate transcription. The terminator sequence is operably linked to the 3'-terminus of the polynucleotide encoding the polypeptide. Any terminator that is functional in the host cell of choice may be used in the present invention.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, when transcribed is a nontranslated region of an mRNA that is important for translation by the host cell. The leader sequence is operably linked to the 5'-terminus of the polynucleotide encoding the polypeptide. Any leader sequence that is functional in the host cell of choice may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell of choice may be used.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice may be used.

Effective signal peptide coding sequences for bacterial host cells are the signal peptide coding sequences obtained from the genes for Bacillus NCIB 11837 maltogenic amylase, Bacillus licheniformis subtilisin, Bacillus licheniformis beta-lactamase, Bacillus stearothermophilus alpha-amylase, Bacillus stearothermophilus neutral proteases (nprT, nprS, nprM), and Bacillus subtilis prsA. Further signal peptides are described by Simonen and Palva, 1993, Microbiological Reviews 57: 109-137.

Effective signal peptide coding sequences for filamentous fungal host cells are the signal peptide coding sequences obtained from the genes for Aspergillus niger neutral amylase, Aspergillus niger glucoamylase, Aspergillus oryzae TAKA amylase, Humicola insolens cellulase, Humicola insolens endoglucanase V, Humicola lanuginosa lipase, and Rhizomucor miehei aspartic proteinase.

Useful signal peptides for yeast host cells are obtained from the genes for Saccharomyces cerevisiae alpha-factor and Saccharomyces cerevisiae invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for Bacillus subtilis alkaline protease (aprE), Bacillus subtilis neutral protease (nprT), Myceliophthora thermophila laccase (WO 95/33836), Rhizomucor miehei aspartic proteinase, and Saccharomyces cerevisiae alpha-factor.

Where both signal peptide and propeptide sequences are present at the N-terminus of a polypeptide, the propeptide sequence is positioned next to the N-terminus of a polypeptide and the signal peptide sequence is positioned next to the N-terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the Aspergillus niger glucoamylase promoter, Aspergillus oryzae TAKA alpha-amylase promoter, and Aspergillus oryzae glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more (several) convenient restriction sites to allow for insertion or substitution of the polynucleotide encoding the polypeptide at such sites. Alternatively, the polynucleotide may be expressed by inserting the polynucleotide or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from Bacillus subtilis or Bacillus licheniformis, or markers that confer antibiotic resistance such as ampicillin, chloramphenicol, kanamycin, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an Aspergillus cell are the amdS and pyrG genes of Aspergillus nidulans or Aspergillus oryzae and the bar gene of Streptomyces hygroscopicus.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more (several) control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any gram-positive or gram-negative bacterium. Gram-positive bacteria include, but not limited to, *Bacillus*, *Clostridium*, *Enterococcus*, *Geobacillus*, *Lactobacillus*, *Lactococcus*, *Oceanobacillus*, *Staphylococcus*, *Streptococcus*, and *Streptomyces*. Gram-negative bacteria include, but not limited to, *Campylobacter*, *E. coli*, *Flavobacterium*, *Fusobacterium*, *Helicobacter*, *Ilyobacter*, *Neisseria*, *Pseudomonas*, *Salmonella*, and *Ureaplasma*.

The bacterial host cell may be any *Bacillus* cell including, but not limited to, *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis* cells.

The bacterial host cell may also be any *Streptococcus* cell including, but not limited to, *Streptococcus equisimllis*, *Streptococcus pyogenes*, *Streptococcus uberis*, and *Streptococcus equi* subsp. *Zooepidemicus* cells.

The bacterial host cell may also be any *Streptomyces* cell including, but not limited to, *Streptomyces achromogenes*, *Streptomyces avermitllis*, *Streptomyces coelicolor*, *Streptomyces griseus*, and *Streptomyces lividans* cells.

The introduction of DNA into a *Bacillus* cell may, for instance, be effected by protoplast transformation (see, e.g., Chang and Cohen, 1979, *Mol. Gen. Genet.* 168: 111-115), by using competent cells (see, e.g., Young and Spizizen, 1961, *J. Bacteriol.* 81: 823-829, or Dubnau and Davidoff-Abelson, 1971, *J. Mol. Biol.* 56: 209-221), by electroporation (see, e.g., Shigekawa and Dower, 1988, *Biotechniques* 6: 742-751), or by conjugation (see, e.g., Koehler and Thorne, 1987, *J. Bacteriol.* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol. (Praha)* 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios* 68: 189-207, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of*

*Yeast* (Skinner, F. A., Passmore, S. M., and Davenport, R. R., eds, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus etyngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023 and Yelton et al., 1984, *Proc. Natl. Acad. Sci. USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In a preferred aspect, the cell is of the genus [Genus]. In a more preferred aspect, the cell is [Genus species]. In a most preferred aspect, the cell is [Genus species deposit number].

The present invention also relates to methods of producing a polypeptide of the present invention, comprising: (a) cultivating a recombinant host cell of the present invention under conditions conducive for production of the polypeptide; and (b) recovering the polypeptide.

The host cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

In an alternative aspect, the polypeptide is not recovered, but rather a host cell of the present invention expressing a polypeptide is used as a source of the polypeptide.

Plants

The present invention also relates to plants, e.g., a transgenic plant, plant part, or plant cell, comprising an isolated polynucleotide of the present invention so as to express and produce the polypeptide in recoverable quantities. The polypeptide may be recovered from the plant or plant part. Alternatively, the plant or plant part containing the polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing a polypeptide may be constructed in accordance with methods known in the art. In short, the plant or plant cell is constructed by incorporating one or more (several) expression constructs encoding the polypeptide into the plant host genome or chloroplast genome and propagating the resulting modified plant or plant cell into a transgenic plant or plant cell.

The expression construct is conveniently a nucleic acid construct that comprises a polynucleotide encoding a polypeptide operably linked with appropriate regulatory sequences required for expression of the polynucleotide in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 12: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide in the plant. For instance, the promoter enhancer element may be an intron that is placed between the promoter and the polynucleotide encoding a polypeptide. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Mol. Biol.* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods for use in accordance with the present disclosure include those described in U.S. Pat. Nos. 6,395,966 and 7,151,204 (which are incorporated herein by reference).

Following transformation, the transformants comprising the expression construct are selected and regenerated into whole plants according to methods well known in the art. Often the transformation procedure is designed for the selective elimination of selection genes either during regeneration or in the following generations by using, for example, cotransformation with two separate T-DNA constructs or site specific excision of the selection gene by a specific recombinase.

In addition to direct transformation of a particular plant genotype with a construct prepared according to the present invention, transgenic plants may be made by crossing a plant having the construct to a second plant lacking the construct. For example, a construct encoding a polypeptide can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention, or a portion of a DNA construct prepared in accordance with the present invention. Crossing results in the introduction of a transgene into a plant line by cross pollinating a starting line with a donor plant line. Non-limiting examples of such steps are further articulated in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide of the present invention comprising: (a) cultivating a transgenic plant or a plant cell comprising a polynucleotide encoding the polypeptide under conditions conducive for production of the polypeptide; and (b) recovering the polypeptide.

Compositions

The present invention also relates to compositions comprising an alpha-amylase and at least one additional enzyme. The additional enzyme(s) may be selected from the group consisting of beta-amylase, cellulase (beta-glucosidase, cellobiohydrolase and endoglucanase), glucoamylase, hemicellulase (e.g., xylanase), isoamylase, isomerase, lipase, phytase, protease, pullulanase, and/or other enzymes useful in a commercial process in conjunction with an alpha-amylase. The additional enzyme may also be a second alpha-amylase. Such enzymes are known in the art in starch processing, sugar conversion, fermentations for alcohol and other useful end-products, commercial detergents and cleaning aids, stain removal, fabric treatment or desizing, and the like.

Methods of Using the Alpha-Amylases—Industrial Applications

The alpha-amylases of the present invention possess valuable properties allowing for a variety of industrial applications. In particular, the alpha-amylases may be used in detergents, in particular laundry detergent compositions and dishwashing detergent compositions, hard surface cleaning compositions, and for desizing textiles, fabrics or garments, production of pulp and paper, beer making, ethanol production, and starch conversion processes.

The alpha-amylases may be used for starch processes, in particular starch conversion, especially liquefaction of starch (see, e.g., U.S. Pat. No. 3,912,590, EP 063909, EP 252730, WO 96/28567 and WO 99/19467, which are incorporated herein by reference). Also contemplated are compositions for starch conversion purposes, which may besides the alpha-amylase of the invention also comprise an AMG, pullulanase, and other alpha-amylases.

Further, the alpha-amylases are particularly useful in the production of sweeteners and ethanol (see, e.g., U.S. Pat. No. 5,231,017, which is incorporated herein by reference), such as fuel, drinking and industrial ethanol, from starch or whole grains.

The alpha-amylases may also be used for desizing of textiles, fabrics, and garments (see, e.g., WO 95/21247, U.S. Pat. No. 4,643,736, and EP 119920, which are incorporated herein by reference), beer making or brewing, and in pulp and paper production or related processes.

Starch Processing

Native starch consists of microscopic granules, which are insoluble in water at room temperature. When an aqueous starch slurry is heated, the granules swell and eventually burst, dispersing the starch molecules into the solution. During this "gelatinization" process there is a dramatic increase in viscosity. As the solids level is 30-40% in a typical industrial process, the starch has to be thinned or "liquefied" so that it can be suitably processed. This reduction in viscosity is primarily attained by enzymatic degradation in current commercial practice.

Conventional starch-conversion processes, such as liquefaction and saccharification processes are described, e.g., in U.S. Pat. No. 3,912,590, EP 252730 and EP 063909, which are incorporated herein by reference.

In an embodiment, the conversion process degrading starch to lower molecular weight carbohydrate components such as sugars or fat replacers includes a debranching step.

In the case of converting starch into a sugar, the starch is depolymerized. Such a depolymerization process consists of, e.g., a pre-treatment step and two or three consecutive process steps, i.e., a liquefaction process, a saccharification process, and depending on the desired end-product, an optional isomerization process.

When the desired final sugar product is, e.g., high fructose syrup the dextrose syrup may be converted into fructose. After the saccharification process, the pH is increased to a value in the range of 6-8, preferably pH 7.5, and the calcium is removed by ion exchange. The dextrose syrup is then converted into high fructose syrup using, e.g., an immobilized glucose isomerase.

Production of Fermentation Products

In general, alcohol production (ethanol) from whole grain can be separated into 4 main steps: milling, liquefaction, saccharification, and fermentation.

The grain is milled in order to open up the structure and allow for further processing. Two processes used are wet or dry milling. In dry milling, the whole kernel is milled and used in the remaining part of the process. Wet milling gives a very good separation of germ and meal (starch granules and protein) and is with a few exceptions applied at locations where there is a parallel production of syrups.

In the liquefaction process the starch granules are solubilized by hydrolysis to maltodextrins mostly of a DP higher than 4. The hydrolysis may be carried out by acid treatment or enzymatically by an alpha-amylase. Acid hydrolysis is used on a limited basis. The raw material can be milled whole grain or a side stream from starch processing.

During a typical enzymatic liquefaction, the long-chained starch is degraded into branched and linear shorter units (maltodextrins) by an alpha-amylase. Enzymatic liquefaction is generally carried out as a three-step hot slurry process. The slurry is heated to between 60-95° C. (e.g., 77-86° C., 80-85° C., or 83-85° C.) and the enzyme(s) is (are) added. The liquefaction process is carried out at 85° C. for 1-2 hours. The pH is generally between 5.5 and 6.2. In order to ensure optimal enzyme stability under these conditions, 1 mM of calcium is added (to provide about 40 ppm free calcium ions). After such treatment, the liquefied starch will have a "dextrose equivalent" (DE) of 10-15.

The slurry is subsequently jet-cooked at between 95-140° C., e.g., 105-125° C., cooled to 60-95° C. and more enzyme(s) is (are) added to obtain the final hydrolysis. The liquefaction process is carried out at pH 4.5-6.5, typically at a pH between 5 and 6. Milled and liquefied grain is also known as mash.

Liquefied starch-containing material is saccharified in the presence of saccharifying enzymes such as glucoamylases. The saccharification process may last for 12 hours to 120 hours (e.g., 12 to 90 hours, 12 to 60 hours and 12 to 48 hours).

However, it is common to perform a pre-saccharification step for about 30 minutes to 2 hours (e.g., 30 to 90 minutes) at a temperature of 30 to 65° C., typically around 60° C. which is followed by a complete saccharification during fermentation referred to as simultaneous saccharification and fermentation (SSF). The pH is usually between 4.2-4.8, e.g., 4.5. In a simultaneous saccharification and fermentation (SSF) process, there is no holding stage for saccharification, rather, the yeast and enzymes are added together.

In a typical saccharification process, maltodextrins produced during liquefaction are converted into dextrose by adding a glucoamylase and a debranching enzyme, such as an isoamylase (U.S. Pat. No. 4,335,208) or a pullulanase. The temperature is lowered to 60° C., prior to the addition of a glucoamylase and debranching enzyme. The saccharification process proceeds for 24-72 hours.

Prior to addition of the saccharifying enzymes, the pH is reduced to below 4.5, while maintaining a high temperature (above 95° C.), to inactivate the liquefying alpha-amylase. This process reduces the formation of short oligosaccharide called "panose precursors," which cannot be hydrolyzed properly by the debranching enzyme. Normally, about 0.2-0.5% of the saccharification product is the branched trisaccharide panose (Glc p$\alpha$1-6Glc p$\alpha$1-4Glc), which cannot be degraded by a pullulanase. If active amylase from the liquefaction remains present during saccharification (i.e., no denaturing), the amount of panose can be as high as 1-2%, which is highly undesirable since it lowers the saccharification yield significantly.

Fermentable sugars (e.g., dextrins, monosaccharides, particularly glucose) are produced by enzymatic saccharification. These fermentable sugars may be further purified and/or converted to useful sugar products. In addition, the sugars may be used as a fermentation feedstock in a microbial fermentation process for producing end-products, such as alcohol (e.g., ethanol and butanol), organic acids (e.g., succinic acid and lactic acid), sugar alcohols (e.g., glycerol), ascorbic acid intermediates (e.g., gluconate, 2-keto-D-gluconate, 2,5-diketo-D-gluconate, and 2-keto-L-gulonic acid), amino acids (e.g., lysine), proteins (e.g., antibodies and fragment thereof).

In an embodiment, the fermentable sugars obtained during the liquefaction process steps are used to produce an alcohol, in particular ethanol. In ethanol production, an SSF process is commonly used wherein the saccharifying enzymes and fermenting organisms (e.g., yeast) are added together and then carried out at a temperature of 30-40° C.

The organism used in fermentation will depend on the desired end-product. Typically, if ethanol is the desired end product yeast will be used as the fermenting organism. In some preferred embodiments, the ethanol-producing microorganism is a yeast and specifically Saccharomyces such as strains of S. cerevisiae (U.S. Pat. No. 4,316,956). A variety of S. cerevisiae are commercially available and include but are not limited to FALI (Fleischmann's Yeast), SUPERSTART (Alltech), FERMIOL (DSM Specialties), RED STAR (Lesaffre) and Angel alcohol yeast (Angel Yeast Company, China). The amount of starter yeast employed in the methods is an amount effective to produce a commercially significant amount of ethanol in a suitable amount of time (e.g., to produce at least 10% ethanol from a substrate having between 25-40% DS in less than 72 hours). Yeast cells are generally supplied in amounts of about $10^4$ to about $10^{12}$, and preferably from about $10^7$ to about $10^{10}$ viable yeast count per mL of fermentation broth. After yeast is added to the mash, it is typically subjected to fermentation for about 24-96 hours, e.g., 35-60 hours. The temperature is between about 26-34° C., typically at about 32° C., and the pH is from pH 3-6, e.g., around pH 4-5.

The fermentation may include, in addition to a fermenting microorganisms (e.g., yeast), nutrients, and additional enzymes, including phytases. The use of yeast in fermentation is well known in the art.

In further embodiments, the use of appropriate fermenting microorganisms, as is known in the art, can result in a fermentation end product such as glycerol, 1,3-propanediol, gluconate, 2-keto-D-gluconate, 2,5-diketo-D-gluconate, 2-keto-L-gulonic acid, succinic acid, lactic acid, amino acids, and derivatives thereof. More specifically when lactic acid is the desired end product, a Lactobacillus sp. (L. casei) may be used; when glycerol or 1,3-propanediol is the desired end-product, E. coli may be used; and when 2-keto-D-gluconate, 2,5-diketo-D-gluconate, and 2-keto-L-gulonic acid are the desired end products, Pantoea citrea may be used as the fermenting microorganism. The above enumerated microorganisms are only examples and one skilled in the art will be aware of other fermenting microorganisms that may be used to obtain a desired end product.

Processes for Producing Fermentation Products from Ungelatinized Starch-Containing Material The invention relates to processes for producing fermentation products from starch-containing material without gelatinization (i.e., without cooking) of the starch-containing material. The fermentation product, such as ethanol, can be produced without liquefying the aqueous slurry containing the starch-containing material and water. In one embodiment a process of the invention includes saccharifying (e.g., milled) starch-containing material, e.g., granular starch, below the initial gelatinization temperature, preferably in the presence of alpha-amylase and/or carbohydrate-source generating enzyme(s) to produce sugars that can be fermented into the fermentation product by a suitable fermenting organism. In this embodiment the desired fermentation product, e.g., ethanol, is produced from ungelatinized (i.e., uncooked), preferably milled, cereal grains, such as corn. Accordingly, in the first aspect the invention relates to processes for producing fermentation products from starch-containing material comprising simultaneously saccharifying and fermenting starch-containing material using a carbohydrate-source generating enzyme and a fermenting organism at a temperature below the initial gelatinization temperature of said starch-containing material. In an embodiment a protease is also present. The protease may be any acid fungal protease or metalloprotease. The fermentation product, e.g., ethanol, may optionally be recovered after fermentation, e.g., by distillation. Typically amylase(s), such as glucoamylase(s) and/or other carbohydrate-source generating enzymes, and/or alpha-amylase(s), is(are) present during fermentation. Examples of glucoamylases and other carbohydrate-source generating enzymes include raw starch hydrolyzing glucoamylases. Examples of alpha-amylase(s) include acid alpha-amylases such as acid fungal alpha-amylases. Examples of fermenting organisms include yeast, e.g., a strain of *Saccharomyces cerevisiae*. The term "initial gelatinization temperature" means the lowest temperature at which starch gelatinization commences. In general, starch heated in water begins to gelatinize between about 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material may be determined as the temperature at which birefringence is lost in 5% of the starch granules using the method described by Gorinstein and Lii, 1992, *Starch/Stärke* 44(12): 461-466. Before initiating the process a slurry of starch-containing material, such as granular starch, having 10-55 w/w % dry solids (DS), preferably 25-45 w/w % dry solids, more preferably 30-40 w/w % dry solids of starch-containing material may be prepared. The slurry may include water and/or process waters, such as stillage (backset), scrubber water, evaporator condensate or distillate, side-stripper water from distillation, or process water from other fermentation product plants. Because the process of the invention is carried out below the initial gelatinization temperature, and thus no significant viscosity increase takes place, high levels of stillage may be used if desired. In an embodiment the aqueous slurry contains from about 1 to about 70 vol. %, preferably 15-60 vol. %, especially from about 30 to 50 vol. % water and/or process waters, such as stillage (backset), scrubber water, evaporator condensate or distillate, side-stripper water from distillation, or process water from other fermentation product plants, or combinations thereof, or the like. The starch-containing material may be prepared by reducing the particle size, preferably by dry or wet milling, to 0.05 to 3.0 mm, preferably 0.1-0.5 mm. After being subjected to a process of the invention at least 85%, at least 86%, at least 87%, at least 88%, at least 89%, at least 90%, at least 91%, at least 92%, at least 93%, at least 94%, at least 95%, at least 96%, at least 97%, at least 98%, or preferably at least 99% of the dry solids in the starch-containing material are converted into a soluble starch hydrolyzate. A process in this aspect of the invention is conducted at a temperature below the initial gelatinization temperature, which means that the temperature typically lies in the range between 30-75° C., preferably between 45-60° C. In a preferred embodiment the process is carried out at a temperature from 25° C. to 40° C., such as from 28° C. to 35° C., from 30° C. to 34° C., preferably around 32° C. In an embodiment the process is carried out so that the sugar level, such as glucose level, is kept at a low level, such as below 6 w/w %, such as below about 3 w/w %, such as below about 2 w/w %, such as below about 1 w/w %., such as below about 0.5 w/w %, or below 0.25 w/w %, such as below about 0.1 w/w %. Such low levels of sugar can be accomplished by simply employing adjusted quantities of enzyme and fermenting organism. A skilled person in the art can easily determine which doses/quantities of enzyme and fermenting organism to use. The employed quantities of enzyme and fermenting organism may also be selected to maintain low concentrations of maltose in the fermentation broth. For instance, the maltose level may be kept below about 0.5 w/w %, such as below about 0.2 w/w %. The process of the invention may be carried out at a pH from about 3 and 7, preferably from pH 3.5 to 6, or more preferably from pH 4 to 5. In an embodiment fermentation is ongoing for 6 to 120 hours, in particular 24 to 96 hours.

Processes for Producing Fermentation Products from Gelatinized Starch-Containing Material In this aspect the invention relates to processes for producing fermentation products, especially ethanol, from a starch-containing material, which process includes a liquefaction step and sequentially or simultaneously performed saccharification and fermentation steps. Consequently, the invention relates to processes for producing fermentation products from starch-containing material comprising the steps of:

(a) liquefying starch-containing material in the presence of an alpha-amylase; or (b) saccharifying the liquefied material obtained in step (a) using a carbohydrate-source generating enzyme;

(c) fermenting using a fermenting organism.

In an aspect, a pullulanase such as a family GH57 pullulanase is also used in the liquefaction step. In an embodiment a protease, such as an acid fungal protease or a metalloprotease is added before, during and/or after liquefaction. In an embodiment the metalloprotease is derived from a strain of *Thermoascus*, e.g., a strain of *Thermoascus aurantiacus*, especially *Thermoascus aurantiacus* CGMCC No. 0670. In an embodiment the carbohydrate-source generating enzyme is a glucoamylase derived from a strain of *Aspergillus*, e.g., *Aspergillus niger* or *Aspergillus awamori*, a strain of *Talaromyces*, especially *Talaromyces emersonii*; or a strain of *Athelia*, especially *Athelia rolfsii*; a strain of *Trametes*, preferably *Trametes cingulata*; a strain of *Pachykytospora*, e.g., a strain of *Pachykytospora papyracea*; or a strain of *Leucopaxillus*, e.g., *Leucopaxillus giganteus*; or a strain of *Peniophora*, e.g., a strain of the species *Peniophora rufomarginata*; or a mixture thereof. Saccharification step (b) and fermentation step (c) may be carried out either sequentially or simultaneously. A pullulanase and/or metalloprotease may be added during saccharification and/or fermentation when the process is carried out as a sequential saccharification and fermentation process and before or during fermentation when steps (b) and (c) are carried out simultaneously (SSF process). The pullulanase and/or metalloprotease may also advantageously be added before liquefaction (pre-liquefaction treatment), i.e., before or during step (a), and/or after liquefaction (post liquefaction treatment), i.e., after step (a). The pullulanase is most advantageously added before or during liquefaction, i.e., before or during step (a). The fermentation product, such as especially ethanol, may optionally be recovered after fermentation, e.g., by distillation. The fermenting organism is preferably yeast, preferably a strain of *Saccharomyces cerevisiae*. In a particular embodiment, the process of the invention further comprises, prior to step (a), the steps of:

x) reducing the particle size of the starch-containing material, preferably by milling (e.g., using a hammer mill);

y) forming a slurry comprising the starch-containing material and water.

In a preferred embodiment the particle size is smaller than a #7 screen, e.g., a #6 screen. The aqueous slurry may contain from 10-55 w/w % dry solids (DS), e.g., 25-45 or 30-40 w/w % dry solids (DS) of starch-containing material. The slurry is heated to above the gelatinization temperature and an alpha-amylase may be added to initiate liquefaction (thinning). The slurry may be jet-cooked to further gelatinize the slurry before being subjected to alpha-amylase in step (a). Liquefaction may be carried out as a three-step hot slurry process. The slurry is heated to between 60-95° C., preferably between 70-90° C., such as preferably between 80-85° C. at pH 4-6, preferably 4.5-5.5, and an alpha-amylase, optionally together with a pullulanase and/or protease, preferably metalloprotease, are added to initiate liquefaction (thinning). In an embodiment the slurry may then be jet-cooked at a temperature between 95-140° C., preferably 100-135° C., such as 105-125° C., for about 1-15 minutes, preferably for about 3-10 minutes, especially around about 5 minutes. The slurry is cooled to 60-95° C. and more alpha-amylase and optionally pullulanase and/or protease, preferably metalloprotease, is(are) added to finalize hydrolysis (secondary liquefaction). The liquefaction process is usually carried out at pH 4-6, in particular at a pH from 4.5 to 5.5. Saccharification step (b) may be carried out using conditions well known in the art. For instance, a full saccharification process may last up to from about 24 to about 72 hours, however, it is common only to do a pre-saccharification of typically 40-90 minutes at a temperature between 30-65° C., typically about 60° C., followed by complete saccharification during fermentation in a simultaneous saccharification and fermentation process (SSF process). Saccharification is typically carried out at temperatures from 20-75° C., preferably from 40-70° C., typically around 60° C., and at a pH between 4 and 5, normally at about pH 4.5. The most widely used process to produce a fermentation product, especially ethanol, is a simultaneous saccharification and fermentation (SSF) process, in which there is no holding stage for the saccharification, meaning that a fermenting organism, such as yeast, and enzyme(s), may be added together. SSF may typically be carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours.

Beer Making

The alpha-amylases may also be used in a beer-making process and similar fermentations; the alpha-amylases will typically be added during the mashing process. The process is substantially similar to the milling, liquefaction, saccharification, and fermentation processes described above.

Starch Slurry Processing with Stillage

Milled starch-containing material is combined with water and recycled thin-stillage resulting in an aqueous slurry. The slurry can comprise between 15 to 55% ds w/w (e.g., 20 to 50%, 25 to 50%, 25 to 45%, 25 to 40%, 20 to 35% and 30-36% ds). In some embodiments, the recycled thin-stillage (backset) is in the range of about 10 to 70% v/v (e.g., 10 to 60%, 10 to 50%, 10 to 40%, 10 to 30%, 10 to 20%, 20 to 60%, 20 to 50%, 20 to 40% and also 20 to 30%).

Once the milled starch-containing material is combined with water and backset, the pH is not adjusted in the slurry. Further the pH is not adjusted after the addition of a phytase and optionally an alpha-amylase to the slurry. In an embodiment, the pH of the slurry will be in the range of about 4.5 to less than about 6.0 (e.g., pH 4.5 to 5.8; 4.5 to 5.6; 4.8 to 5.8; 5.0 to 5.8; 5.0 to 5.4; 5.2 to 5.5; and 5.2 to 5.9). The pH of the slurry may be between about 4.5 and 5.2 depending on the amount of thin stillage added to the slurry and the type of material comprising the thin stillage. For example, the pH of the thin stillage may be between 3.8 and 4.5.

During ethanol production, acids can be added to lower the pH in the beer well, to reduce the risk of microbial contamination prior to distillation.

In some embodiments, a phytase is added to the slurry. In other embodiments, in addition to a phytase, an alpha-amylase is added to the slurry. In some embodiments, a phytase and alpha-amylase are added to the slurry sequentially. In other embodiments, a phytase and alpha-amylase are added simultaneously. In some embodiments, the slurry comprising a phytase and optionally, an alpha-amylase, are incubated (pretreated) for a period of about 5 minutes to about 8 hours (e.g., 5 minutes to 6 hours, 5 minutes to 4 hours, 5 minutes to 2 hours, and 15 minutes to 4 hours). In other embodiments, the slurry is incubated at a temperature in the range of about 40 to 115° C. (e.g., 45 to 80° C., 50 to 70° C., 50 to 75° C., 60 to 110° C., 60 to 95° C., 70 to 110° C., 70 to 85° C. and 77 to 86° C.).

In other embodiments, the slurry is incubated at a temperature of about 0 to about 30° C. (e.g., 0 to 25° C., 0 to 20° C., 0 to 15° C., 0 to 10° C. and 0 to 5° C.) below the starch gelatinization temperature of the starch-containing material. In some embodiments, the temperature is below about 68° C., below about 65° C., below about 62° C., below about 60° C. and below about 55° C. In some embodiments, the temperature is above about 45° C., above about 50° C., above about 55° C. and above about 60° C. In some embodiments, the incubation of the slurry comprising a phytase and an alpha-amylase at a temperature below the starch gelatinization temperature is referred to as a primary (1°) liquefaction.

In one embodiment, the milled starch-containing material is corn or milo. The slurry comprises 25 to 40% DS, the pH is in the range of 4.8 to 5.2, and the slurry is incubated with a phytase and optionally an alpha-amylase for 5 minutes to 2 hours, at a temperature range of 60 to 75° C.

Currently, it is believed that commercially-available microbial alpha-amylases used in the liquefaction process are generally not stable enough to produce liquefied starch substrate from a dry mill process using whole ground grain at a temperature above about 80° C. at a pH level that is less than pH 5.6. The stability of many commercially available alpha-amylases is reduced at a pH of less than about 4.0.

In a further liquefaction step, the incubated or pretreated starch-containing material is exposed to an increase in temperature such as about 0 to about 45° C. above the starch gelatinization temperature of the starch-containing material (e.g., 70° C. to 120° C., 70° C. to 110° C., and 70° C. to 90° C.) for a period of time of about 2 minutes to about 6 hours (e.g., 2 minutes to 4 hrs, 90 minutes, 140 minutes and 90 to 140 minutes) at a pH of about 4.0 to 5.5 more preferably between 1 hour to 2 hours. The temperature can be increased by a conventional high temperature jet cooking system for a short period of time, for example, for 1 to 15 minutes. Then the starch may be further hydrolyzed at a temperature in the range of about 75° C. to 95° C. (e.g., 80° C. to 90° C. and 80° C. to 85° C.) for a period of about 15 to 150 minutes (e.g., 30 to 120 minutes). In a preferred embodiment, the pH is not adjusted during these process steps and the pH of the liquefied mash is in the range of about pH 4.0 to pH 5.8 (e.g., pH 4.5 to 5.8; 4.8 to 5.4; and 5.0 to 5.2). In some embodiments, a second dose of thermostable alpha-amylase is added to the secondary liquefaction step, but in other embodiments there is no additional dosage of alpha-amylase.

The incubation and liquefaction steps may be followed by saccharification and fermentation steps well known in the art.

Distillation

Optionally, following fermentation, an alcohol (e.g., ethanol) may be extracted by, for example, distillation and optionally followed by one or more process steps.

In some embodiments, the yield of ethanol produced by the methods provided herein is at least 8%, at least 10%, at least 12%, at least 14%, at least 15%, at least 16%, at least 17% and at least 18% (v/v) and at least 23% v/v. The ethanol obtained according to the process provided herein may be used as, for example, fuel ethanol, drinking ethanol, i.e., potable neutral spirits, or industrial ethanol.

By-Products

Left over from the fermentation is the grain, which is typically used for animal feed either in liquid or dried form. In further embodiments, the end product may include the fermentation co-products such as distiller's dried grains (DDG) and distiller's dried grain plus solubles (DDGS), which may be used, for example, as an animal feed.

Further details on how to carry out liquefaction, saccharification, fermentation, distillation, and recovery of ethanol are well known to the skilled person.

According to the process provided herein, the saccharification and fermentation may be carried out simultaneously or separately.

Pulp and Paper Production

The alpha-amylases may also be used in the production of lignocellulosic materials, such as pulp, paper and cardboard, from starch reinforced waste paper and cardboard, especially where re-pulping occurs at pH above 7 and where amylases facilitate the disintegration of the waste material through degradation of the reinforcing starch. The alpha-amylases are especially useful in a process for producing a papermaking pulp from starch-coated printed-paper. The process may be performed as described in WO 95/14807, comprising the following steps:

a) disintegrating the paper to produce a pulp,
b) treating with a starch-degrading enzyme before, during or after step a), and
c) separating ink particles from the pulp after steps a) and b).

The alpha-amylases may also be very useful in modifying starch where enzymatically modified starch is used in papermaking together with alkaline fillers such as calcium carbonate, kaolin and clays. With the alpha-amylases it is possible to modify the starch in the presence of the filler thus allowing for a simpler integrated process.

Desizing of Textiles, Fabrics and Garments

The alpha-amylases may also be useful in textile, fabric or garment desizing. In the textile processing industry, alpha-amylases are traditionally used as auxiliaries in the desizing process to facilitate the removal of starch-containing size, which has served as a protective coating on weft yarns during weaving. Complete removal of the size coating after weaving is important to ensure optimum results in the subsequent processes, in which the fabric is scoured, bleached and dyed. Enzymatic starch breakdown is preferred because it does not involve any harmful effect on the fiber material. In order to reduce processing cost and increase mill throughput, the desizing process is sometimes combined with the scouring and bleaching steps. In such cases, non-enzymatic auxiliaries such as alkali or oxidation agents are typically used to break down the starch, because traditional alpha-amylases are not very compatible with high pH levels and bleaching agents. The non-enzymatic breakdown of the starch size leads to some fiber damage because of the rather aggressive chemicals used. Accordingly, it would be desirable to use the alpha-amylases as they have an improved performance in alkaline solutions. The alpha-amylases may be used alone or in combination with a cellulase when desizing cellulose-containing fabric or textile.

Desizing and bleaching processes are well known in the art. For instance, such processes are described in, e.g., WO 95/21247, U.S. Pat. No. 4,643,736, and EP 119920, which are incorporated herein by reference.

Cleaning Processes and Detergent Compositions

The alpha-amylases may be added as a component of a detergent composition for various cleaning or washing processes, including laundry and dishwashing. For example, the alpha-amylases may be used in the detergent compositions described in WO 96/23874 and WO 97/07202.

The alpha-amylases may be incorporated in detergents at conventionally employed concentrations. For example, an alpha-amylase of the invention may be incorporated in an amount corresponding to 0.00001-10 mg (calculated as pure, active enzyme protein) of alpha-amylase per liter of wash/dishwash liquor using conventional dosing levels of detergent.

The detergent composition may for example be formulated as a hand or machine laundry detergent composition, including a laundry additive composition suitable for pretreatment of stained fabrics and a rinse added fabric softener composition or be formulated as a detergent composition for use in general household hard surface cleaning operations, or be formulated for hand or machine dishwashing operations.

The detergent composition may further comprise one or more other enzymes, such as a lipase, peroxidase, protease, another amylolytic enzyme, e.g., another alpha-amylase, glucoamylase, maltogenic amylase, CGTase, cellulase, mannanase (such as Mannaway™ from Novozymes, Denmark)), pectinase, pectin lyase, cutinase, and/or laccase.

In general the properties of the chosen enzyme(s) should be compatible with the selected detergent (i.e., pH-optimum, compatibility with other enzymatic and non-enzymatic ingredients, etc.), and the enzyme(s) should be present in effective amounts.

The detergent enzyme(s) may be included in a detergent composition by adding separate additives containing one or more enzymes, or by adding a combined additive comprising all of these enzymes. A detergent additive, e.g., a separate additive or a combined additive, can be formulated, e.g., granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonyl-phenols having from 16 to 50 ethylene oxide units; ethoxylated fatty alcohols in which the alcohol contains from 12 to 20 carbon atoms and in which there are 15 to 80 ethylene oxide units; fatty alcohols, fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238216.

The detergent composition may be in any convenient form, e.g., a bar, a tablet, a powder, a granule, a paste or a liquid. A liquid detergent may be aqueous, typically containing up to about 70% water and 0 to about 30% organic solvent, or non-aqueous.

The detergent composition comprises one or more surfactants, which may be non-ionic including semi-polar and/or anionic and/or cationic and/or zwitterionic. The surfactants are typically present at a level of from about 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonyl-phenol ethoxylate, alkylpolyglycoside, alkyldimethylamine-oxide, ethoxylated fatty acid monoethanol-amide, fatty acid monoethanolamide, polyhydroxy alkyl fatty acid amide, or N-acyl N-alkyl derivatives of glucosamine ("glucamides").

The detergent may contain 0 to about 65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g., SKS-6 from Hoechst).

The detergent may comprise one or more polymers. Examples are carboxymethylcellulose, poly(vinyl-pyrrolidone), poly(ethylene glycol), poly(vinyl alcohol), poly(vinylpyridine-N-oxide), poly(vinylimidazole), polycarboxylates such as polyacrylates, maleiclacrylic acid copolymers and lauryl methacrylate/acrylic acid co-polymers.

The detergent may contain a bleaching system, which may comprise a $H_2O_2$ source such as perborate or percarbonate which may be combined with a peracid-forming bleach activator such as tetraacetylethylenediamine or nonanoyloxyben-zenesul-fonate. Alternatively, the bleaching system may comprise peroxy acids of, e.g., the amide, imide, or sulfone type.

The enzyme(s) of the detergent composition may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, e.g., WO 92/19708 and WO 92/19709.

The detergent may also contain other conventional detergent ingredients such as, e.g., fabric conditioners including clays, foam boosters, suds suppressors, anti-corrosion agents, soil-suspending agents, anti-soil re-deposition agents, dyes, bactericides, optical brighteners, hydrotropes, tarnish inhibitors, or perfumes.

The detergent compositions may comprise any enzyme in an amount corresponding to 0.01-100 mg of enzyme protein per liter of wash liquor, preferably 0.055 mg of enzyme protein per liter of wash liquor, in particular 0.1-1 mg of enzyme protein per liter of wash liquor.

One or more of the alpha-amylases described herein may additionally be incorporated in the detergent formulations disclosed in WO 97/07202, which is incorporated herein by reference.

This disclosure includes further detail in the following examples, which are not in any way intended to limit the scope of what is claimed. The following examples are thus offered to illustrate, but not to limit what is claimed.

EXAMPLES

Materials and Methods

Fermentation of Alpha-Amylases and Variants

Fermentation may be performed by methods well known in the art or as follows:

A *B. subtilis* strain harboring the relevant expression plasmid is streaked on a LB-agar plate with a relevant antibiotic, and grown overnight at 37° C.

The colonies are transferred to 100 ml BPX media supplemented with a relevant antibiotic (for instance 10 mg/l chloroamphinicol) in a 500 ml shaking flask.

Composition of BPX Medium:

| | |
|---|---|
| Potato starch | 100 g/l |
| Barley flour | 50 g/l |
| BAN 5000 SKB | 0.1 g/l |
| Sodium caseinate | 10 g/l |
| Soy Bean Meal | 20 g/l |
| $Na_2HPO_4$, 12 $H_2O$ | 9 g/l |
| Pluronic ™ | 0.1 g/l |

BAN is a *Bacillus amyloliquefaciens* alpha-amylase product sold by Novozymes.

The culture is shaken at 37° C. at 270 rpm for 4 to 5 days.

Cells and cell debris are removed from the fermentation broth by centrifugation at 4500 rpm in 20-25 minutes. Afterwards the supernatant is filtered to obtain a completely clear solution. The filtrate is concentrated and washed on an UF-filter (10000 cut off membrane) and the buffer is changed to 20 mM acetate pH 5.5. The UF-filtrate is applied on an S-sepharose F.F. and elution is carried out by step elution with 0.2 M NaCl in the same buffer. The eluate is dialyzed against 10 mM Tris, pH 9.0 and applied on a Q-sepharose F.F. and eluted with a linear gradient from 0-0.3 M NaCl over 6 column volumes. The fractions, which contain the activity (measured by the Phadebas assay) are pooled, pH is adjusted to 7.5 and remaining color is removed by a treatment with 0.5% w/vol active coal in 5 minutes.

Phadebas Assay

Alpha-amylase activity is determined by a method employing Phadebas® tablets as substrate. Phadebas tablets (Phadebas® Amylase Test, supplied by Magle Life Sciences, Lund, Sweden) contain a cross-linked insoluble blue-colored starch polymer, which has been mixed with bovine serum albumin and a buffer substance and tabletted.

For every single measurement one tablet is suspended in a tube containing 5 mL 50 mM Britton-Robinson buffer (50 mM acetic acid, 50 mM phosphoric acid, 50 mM boric acid, 0.1 mM $CaCl_2$, 0.01% TRITON® X100, pH adjusted to the value of interest with NaOH). This is the substrate solution. The alpha-amylase to be tested is diluted in 50 mM Britton-Robinson buffer. This is the amylase solution. The test is performed at constant temperature, e.g., at room temperature, 37° C. or 50° C. The insoluble blue-colored starch polymer is hydrolyzed by the alpha-amylase giving soluble blue fragments. The absorbance of the resulting blue solution, measured spectrophotometrically at 620 nm, is a function of the alpha-amylase activity.

575 microliters substrate solution is equilibrated at the selected temperature for 5 minutes. The hydrolysis is started by adding 25 microliters amylase solution to the substrate solution and incubating the sample under gentle mixing for 15 minutes at the selected temperature. The reaction is stopped by adding 100 microliters 1 M NaOH and immediately cooling on an ice bath after mixing. After centrifugation at 500 $g_{av}$ for 3 minutes, 200 microliters of the supernatant is transferred to a microtiter plate, and the absorbance at 620 nm is read ($A_{amyl}$). The blind is prepared as described but where the 25 microliters amylase solution is replaced by 25 microliters 50 mM Britton-Robison buffer. The absorbance of the blind at 620 nm is $A_b$. The standard curve is prepared similarly by making a dilution series of Termamyl with a known activity and measuring the release of blue color to the solution as described above. The absorbance of the standards at 620 nm is $A_s$. The standard curve is a plot of $A_s$-$A_b$ against the Termamyl activity in the sample. The activity of the amylase of interest can be determined by comparing $A_{amyl}$-$A_b$ to the Termamyl standard curve.

It is important that the measured 620 nm absorbance after 15 minutes of incubation (testing time) is in the range of 0.2 to 2.0 absorbance units at 620 nm. In this absorbance range there is linearity between activity and absorbance (Lambert-Beer law). The dilution of the enzyme (both amylase of interest and standard) must therefore be adjusted to fit this criterion. Under a specified set of conditions (temperature, pH, reaction time, buffer conditions), 1 mg of a given alpha-amylase will hydrolyze a certain amount of substrate and a blue color will be produced.

G7-pNP Amylase Assay

Alpha-amylase activity may also be determined by a method employing the PNP-G7 substrate. PNP-G7 which is an abbreviation for p-nitrophenyl-alpha-D-maltoheptaoside, is a blocked oligosaccharide which can be cleaved by an endo-amylase. Following the cleavage, the alpha-glucosidase included in the kit digests the substrate to liberate a free PNP molecule which has a yellow color and thus can be measured by visible spectophometry at λ=405 nm (400-420 nm). Kits containing PNP-G7 substrate and alpha-glucosidase is manufactured by Roche/Hitachi (cat. no. 11876473). The G7-PNP substrate from this kit contains 22 mmol/L 4,6-ethylidene-G7-PNP and 52.4 mmol/L HEPES (2-[4-(2-hydroxyethyl)-1-piperazinyl]-ethanesulfonic acid), pH 7.0) and the alpha-glucosidase contains 52.4 mmol/L HEPES, 87 mmol/L NaCl, 12.6 mmol/L $MgCl_2$, 0.075 mmol/L $CaCl_2$, ≧4 kU/L alpha-glucosidase).

The amylase sample to be analyzed is diluted in 50 mM EPPS (4-(2-hydroxyethyl)-1-piperazinepropanesulfonic acid (Sigma, E9502)), 0.01% TRITON® X100, 1 mM $CaCl_2$, pH 7.0. Before use substrate working solution was made by mixing 1 mL of the alpha-glucosidase containing reagent with 0.2 mL 4,6-ethylidene-G7-PNP containing reagent from kit. Immediately after incubation of samples in PCR machine the samples are diluted 10 times in residual activity buffer (50 mM EPPS, 0.01% TRITON® X100, 1 mM $CaCl_2$, pH7.0). The assay is performed by transferring 20 microliters diluted enzyme samples to a 96 well microtiter plate and adding 80 microliters substrate working solution. The solution is mixed and pre-incubated 1 minute at room temperature and absorption is measured every 20 sec. over 5 minutes at OD 405 nm.

The slope (absorbance per minute) of the time dependent absorption-curve is directly proportional to the specific activity (activity per mg enzyme) of the alpha-amylase in question under the given set of conditions. The amylase sample should be diluted to a level where the slope is below 0.4 absorbance units per minute.

Enzchek® Amylase Activity Assay

Alpha-amylase activity may also be determined by a method employing the EnzChek® substrate. The substrate in the EnzChek® Ultra Amylase Assay Kit (E33651, Invitrogen, La Jolla, Calif., USA) is a corn starch derivative, DQ™ starch, which is corn starch labeled with BODIPY® FL dye to such a degree that fluorescence is quenched.

One vial containing approx. 1 mg lyophilized substrate is dissolved in 100 microliters of 50 mM sodium acetate (pH 4.0). The vial is vortexed for 20 seconds and left at room temperature, in the dark, with occasional mixing until dissolved. Then 900 microliters of 100 mM acetate, 0.01% (w/v) TRITON® X100, 0.12 mM $CaCl_2$, pH 5.5 is added, vortexed thoroughly and stored at room temperature, in the dark until ready to use. The substrate working solution is prepared by diluting 10-fold in residual activity buffer (100 mM acetate, 0.01% (w/v) TRITON® X100, 0.12 mM $CaCl_2$, pH 5.5) giving a substrate concentration of 100 micrograms/ml. Immediately after incubation the enzyme is diluted to a concentration of 20 ng enzyme protein/mL in 100 mM acetate, 0.01% (W/v) TRITON® X100, 0.12 mM $CaCl_2$, pH 5.5.

For the assay, 25 microliters of the substrate working solution is mixed for 10 second with 25 microliters of the diluted enzyme in a black 384 well microtiter plate. The fluorescence intensity is measured (excitation: 485 nm, emission: 555 nm) once every minute for 15 minutes in each well at 25° C. and the $V_{max}$ is calculated as the slope of the plot of fluorescence intensity against time. The plot should be linear and the residual activity assay has been adjusted so that the diluted reference enzyme solution is within the linear range of the activity assay.

Example 1

Preparation of Hybrids

The following hybrids of the calcium-sensitive alpha-amylase having the sequence shown in SEQ ID NO: 7 and the calcium-insensitive alpha-amylase having the sequence shown in SEQ ID NO: 13 were prepared.

Hybrid 1: the amino acid residues 106-215 of SEQ ID NO: 7 were removed and replaced with the amino acid residues 103-211 of SEQ ID NO: 13, which results in SEQ ID NO: 17, and the following alterations were introduced: E182*, N183*, E188W, N189E and D192T (using SEQ ID NO: 17 numbering), which correspond to E181*, N182*, E187W, N188E and D191T using SEQ ID NO: 27 numbering. The sequence of this hybrid is shown in SEQ ID NO: 18.

Hybrid 2: the amino acid residues 106-214 of SEQ ID NO: 7 were removed and replaced with the amino acid residues 103-210 of SEQ ID NO: 13, which results in SEQ ID NO: 19, and the following alterations were introduced: E182*, N183*, E188W, N189E and D192T (using SEQ ID NO: 19 numbering), which correspond to E181*, N182*, E187W, N188E and D191T using SEQ ID NO: 27 numbering. The sequence of this hybrid is shown in SEQ ID NO: 20.

Hybrid 3: the amino acid residues 106-213 of SEQ ID NO: 7 were removed and replaced with the amino acid residues 103-209 of SEQ ID NO: 13, which results in SEQ ID NO: 21, and the following alterations were introduced: E182*, N183*, E188W, N189E and D192T (using SEQ ID NO: 21 numbering), which correspond to E181*, N182*, E187W, N188E and D191T using SEQ ID NO: 27 numbering. The sequence of this hybrid is shown in SEQ ID NO: 22.

Example 2

Stability in the Presence of Chelator

Enzyme samples were incubated in buffer pH 8.0 (50 mM EPPS, 0.01% TRITON® X100, pH 8.0) with 1.5% final concentration of DTPA at 49° C. for 1 hour and reference samples were incubated at 4° C. for 1 hour. In addition, enzyme samples were incubated in buffer pH 10.0 (50 mM EPPS, 0.01% TRITON® X100, pH 10.0) with 1.5% final concentration of DTPA at 42° C. for 1 hour and reference samples were incubated at 4° C. for 1 hour.

For the determination of amylase stability in buffer pH 8 and pH 10 with DTPA the enzymes to be tested were adjusted to 0.25 and 0.5 mg enzyme protein/mL by diluting in 5 mM EPPS, 0.01% TRITON® X100, pH 8.0.

160 microliters stability buffer (50 mM EPPS, 0.01% TRITON® X100, 1.875% DTPA, pH 8.0 or pH 10.0) and 40 microliters of the amylase solution were transferred to a 96-well PCR microtiter plate in duplicate and the content was mixed for 1 minute. Final concentration of DTPA was 1.5% in each well. 20 microliters from each well was transferred to a new PCR microtiter plate, which was placed at 4° C. (reference sample). The PCR MTP was incubated in PCR machine for 1 hour at 49° C. when buffer had pH 8.0 (pH 8, 49° C. samples) and for 1 hour at 42° C. when buffer had pH 10.0 (pH 10, 42° C. samples).

Immediately after incubation, the samples on PCR plates were analyzed for amylase activity as described in the G7-pNP Amylase assay. It should be noted that in order to reduce interference from DTPA on the assay, both reference and pH 8, 49° C. samples/pH 10, 42° C. samples were diluted to the same concentration before being analyzed for residual activity. The activity of both the reference samples and the pH 8, 49° C. samples or pH 10, 42° C. samples were determined on the same 96 well plate. The residual activity was calculated as $100*V_{max}$(pH 8, 42° C. or pH 10, 49° C. sample)/$V_{max}$ (reference sample).

| Enzyme | Residual activity in % after 1 hour 49° C., pH 8.0 and 1.5% DTPA | Residual activity in % after 1 hour 42° C., pH 10.0 and 1.5% DTPA |
| --- | --- | --- |
| SEQ ID NO: 7 with the deletions D183* + T184* (SEQ ID NO: 7 numbering) | 20 | 18 |
| SEQ ID NO: 7 | 1 | 9 |
| SP707 (SEQ ID NO: 8) | 1 | 3 |
| Hybrid 1 | 100 | 102 |
| Hybrid 2 | 102 | 102 |
| Hybrid 3 | 103 | 103 |

Hybrids 1, 2 and 3 are highly stable and have 100% residual activity after incubation for 1 hour at both pH 8, 49° C. and pH 10, 42° C. In comparison SEQ ID NO: 7 with the deletions D183*+T184* has less than 20% residual activity at these conditions and SEQ ID NO: 7 and SP707 have even less residual activity.

Example 3

Additional Alpha-Amylases

The following alpha-amylases were prepared:
Hybrid 4: the amino acid residues 106-212 of SEQ ID NO: 5 were removed and replaced with the amino acid residues 103-208 of SEQ ID NO: 13, which results in SEQ ID NO: 23, and the following alterations were introduced: E182*, N183*, E188W, N189E and D192T (using SEQ ID NO: 23 numbering), which correspond to E181*, N182*, E187W, N188E and D191T in SEQ ID NO: 27 numbering. The sequence of this hybrid is shown in SEQ ID NO: 24.
Hybrid 5: the amino acid residues 106-212 of SEQ ID NO: 8 were removed and replaced with the amino acid residues 103-208 of SEQ ID NO: 13, which results in SEQ ID NO: 25, and the following alterations were introduced: E182*, N183*, E188W, N189E and D192T (using SEQ ID NO: 25 numbering), which correspond to E181*, N182*, E187W, N188E and D191T in SEQ ID NO: 27 numbering. The sequence of this hybrid is shown in SEQ ID NO: 26.

Hybrids 4 and 5 (SEQ ID NOS: 24 and 26), a variant of SEQ ID NO: 5 with the alterations E182*, N183*, E188W, N189E and D192T (using SEQ ID NO: 5 numbering), which correspond to E181*, N182*, E187W, N188E and D191T in SEQ ID NO: 27 numbering, and the alpha-amylase of SEQ ID NO: 8 were incubated with DTPA as described in Example 2. The results show that hybrids 4 and 5 had almost 100% residual activity after the incubations, whereas the other alpha-amylases lost most of their activity during the incubations.

Example 4

Stability of Alpha-Amylase Variants

The stability of a reference alpha-amylase with the amino acid sequence of SEQ ID NO: 28 (a hybrid of *Bacillus stearothermophilus* and *Bacillus circulans* alpha-amylases (SEQ ID NO: 27) with the alterations E181*+G182*+E187W+N188E+D191T+D407N+D430N+P432D) and alpha-amylase variants thereof was determined by incubating the reference alpha-amylase and variants at pH 4.5 and 5.5 and temperatures of 75° C. and 85° C. with 0.12 mM $CaCl_2$ followed by residual activity determination using the EnzChek® substrate (EnzChek® Ultra Amylase assay kit, E33651, Molecular Probes, Invitrogen, La Jolla, Calif., USA).

Purified enzyme samples were diluted to working concentrations of 0.5 and 1 or 5 and 10 ppm (micrograms/ml) in enzyme dilution buffer (10 mM acetate, 0.01% TRITON® X100, 0.12 mM $CaCl_2$, pH 5.0). Twenty microliters enzyme sample was transferred to 48-well PCR MTP and 180 microliters stability buffer (150 mM acetate, 150 mM MES, 0.01% TRITON® X100, 0.12 mM $CaCl_2$, pH 4.5 or 5.5) was added to each well and mixed. The assay was performed using two concentrations of enzyme in duplicates. Before incubation at 75° C. or 85° C., 40 microliters was withdrawn and stored on ice as reference samples. Incubation was performed in a PCR machine for 30/45 minutes (pH 4.5 and 75° C.), 45/60 minutes (pH 5.5 and 75° C.), 5/10 minutes (pH 4.5 and 85° C.) and 10 minutes (pH 5.5 and 85° C.).

After incubation, the reference samples and samples from the PCR machine were diluted to 20 ng/ml in residual activity buffer (100 mM acetate, 0.01% TRITON® X100, 0.12 mM $CaCl_2$, pH 5.5) and 25 microliters diluted enzyme was transferred to black 384-MTP. Residual activity was determined using the EnzChek® substrate as described in the section for the Enzchek® amylase activity assay. In brief, 25 microliters substrate working solution (100 micrograms/ml) is added to each well with diluted enzyme. Fluorescence was determined every minute for 15 minutes using excitation filter at 485-P nm and emission filter at 555 nm (fluorescence reader is Polarstar, BMG). The residual activity was normalized to control samples for each setup.

Assuming logarithmic decay the half life time (T½(min)) was calculated using the equation: T½(min)=T(min)*LN(0.5)/LN(% RA/100), where T is the assay incubation time in minutes, and % RA is the % residual activity determined in the assay.

Using this assay setup the half life time was determined for the reference alpha-amylase and variants thereof as shown in Table 1.

TABLE 1

| Mutations (SEQ ID NO: 27 numbering) | T½ (min) (pH 4.5, 75° C., 0.12 mM CaCl$_2$) | T½ (min) (pH 5.5, 75° C., 0.12 mM CaCl$_2$) | T½ (min) (pH 4.5, 85° C., 0.12 mM CaCl$_2$) | T½ (min) (pH 5.5, 85° C., 0.12 mM CaCl$_2$) |
|---|---|---|---|---|
| Reference Alpha-Amylase | 14 ± 2 | 33 ± 4 | 1.8 ± 0.2 | 4.5 ± 0.2 |
| Reference Alpha-Amylase with the substitutions M8L + N105D + K184A | 49 | | 4.2 | 13 |
| Reference Alpha-Amylase with the substitutions A27Q + Q86S + A90S + N105D + K184A | 58 | | 4.7 | 15 |
| Reference Alpha-Amylase with the substitutions S34K + N105D + K184A + S242Q | 59 | | 6.8 | 28 |
| Reference Alpha-Amylase with the substitutions R52G + S53Y + N105D + K184A | 50 | | 5.2 | 15 |
| Reference Alpha-Amylase with the substitutions V59A + A100G + N105D + T164V + K184A + M307L | 91 | | 11.3 | 29 |
| Reference Alpha-Amylase with the substitutions V59A + N105D + Q150T + T164V + K184A + S242Q + M307L | >120 | | 14.1 | 39 |
| Reference Alpha-Amylase with the substitutions T80D + N105D + T164V + K184A + M307L | 108 | | 9.4 | 24 |
| Reference Alpha-Amylase with the substitutions A91L + N105D + K184A | 51 | | 6.3 | 19 |
| Reference Alpha-Amylase with the substitutions A100L + N105D + T164V + K184A + Y222V + M307L | 69 | | 7.3 | 25 |
| Reference Alpha-Amylase with the substitution N105D | 32 | 129 | 4 | <15 |
| Reference Alpha-Amylase with the substitutions N105D + K117D + Q150T + K184A + S301K + G303R + A304D | 45 | | 5.5 | 21 |
| Reference Alpha-Amylase with the substitutions N105D + E129V + R177L + A179E | 20 | | 3 | 6 |
| Reference Alpha-Amylase with the substitutions N105D + E132D + K184A | 64 | | 5 | 19 |
| Reference Alpha-Amylase with the substitutions N105D + F134E + K184A | 33 | | 3.3 | 9 |
| Reference Alpha-Amylase with the substitutions N105D + E135N + A179N + K184A | 44 | | 3.9 | 16 |
| Reference Alpha-Amylase with the substitutions N105D + Q150T | 27 | 117 | 4 | 10 |
| Reference Alpha-Amylase with the substitutions N105D + Q150T + T164V + F166W + A168E + E171K + K184A + N407D + N430D + D432P | 59 | | 7.3 | 20 |
| Reference Alpha-Amylase with the substitutions N105D + Q150T + T164V + K184A + S242Q + M284T + M307L | >120 | | 13.6 | >40 |
| Reference Alpha-Amylase with the substitutions N105D + Q150T + T164V + | 114 | | 13.4 | >40 |

TABLE 1-continued

| Mutations (SEQ ID NO: 27 numbering) | T½ (min) (pH 4.5, 75° C., 0.12 mM CaCl₂) | T½ (min) (pH 5.5, 75° C., 0.12 mM CaCl₂) | T½ (min) (pH 4.5, 85° C., 0.12 mM CaCl₂) | T½ (min) (pH 5.5, 85° C., 0.12 mM CaCl₂) |
|---|---|---|---|---|
| K184A + S242Q + M284T + N407D | | | | |
| Reference Alpha-Amylase with the substitutions N105D + Q150T + F166W + A168E + E171K | 37 | 141 | 5 | 13 |
| Reference Alpha-Amylase with the substitutions N105D + Q150T + F166W + A168E + E171K + K184A | 68 | | 7.9 | 21 |
| Reference Alpha-Amylase with the substitutions N105D + Q150T + K184A | 46 | 207 | 5.1 | 15 |
| Reference Alpha-Amylase with the substitutions N105D + Q150T + K184A + Y206M | 42 | | 4.7 | 14 |
| Reference Alpha-Amylase with the substitutions N105D + Q150T + K184A + S301K + G303R + A304D | 41 | 111 | 4.6 | 16 |
| Reference Alpha-Amylase with the substitutions N105D + N157Y + E159Y + H160Y + K184A + H208Y + D210Y | 50 | | 5.2 | 15 |
| Reference Alpha-Amylase with the substitutions N105D + H160Y + K184A | 38 | | 4.3 | 13 |
| Reference Alpha-Amylase with the substitutions N105D + T164V + K184A + Y222V + M307L | 71 | | 7.5 | 18 |
| Reference Alpha-Amylase with the substitutions N105D + T164V + K184A + S242Q + M284T + M307L | >120 | | 11.7 | 39 |
| Reference Alpha-Amylase with the substitutions N105D + T164V + K184A + F244Y + M284T + M307L | 68 | | 5.7 | 19 |
| Reference Alpha-Amylase with the substitutions N105D + T164V + K184A + M284Q + M307L | 105 | | 12 | >40 |
| Reference Alpha-Amylase with the substitutions N105D + T164V + K184A + M284V + M307L | >120 | | 14.6 | >40 |
| Reference Alpha-Amylase with the substitutions N105D + T164V + K184A + M307L | 70 | 230 | 8.7 | 23 |
| Reference Alpha-Amylase with the substitutions N105D + F166W + A168E + E171K | 49 | 140 | 4 | 13 |
| Reference Alpha-Amylase with the substitutions N105D + F166W + A168E + E171K + S301K + G303R + A304D | 33 | 112 | 4.8 | 14 |
| Reference Alpha-Amylase with the substitutions N105D + A179D + K184A | 68 | | 5.8 | 19 |
| Reference Alpha-Amylase with the substitutions N105D + A179N + K184A | 56 | | 5.3 | >40 |
| Reference Alpha-Amylase with the substitutions N105D + A179Q + K184A | 56 | | 6 | 28 |
| Reference Alpha-Amylase with the substitutions N105D + K184A | 40 | 153 | 5.6 | 14 |

TABLE 1-continued

| Mutations (SEQ ID NO: 27 numbering) | T½ (min) (pH 4.5, 75° C., 0.12 mM CaCl$_2$) | T½ (min) (pH 5.5, 75° C., 0.12 mM CaCl$_2$) | T½ (min) (pH 4.5, 85° C., 0.12 mM CaCl$_2$) | T½ (min) (pH 5.5, 85° C., 0.12 mM CaCl$_2$) |
|---|---|---|---|---|
| Reference Alpha-Amylase with the substitutions N105D + K184A + D210V | 55 | | 5.8 | 15 |
| Reference Alpha-Amylase with the substitutions N105D + K184A + A235T | 14 | 37 | 1.4 | 4 |
| Reference Alpha-Amylase with the substitutions N105D + K184A + S242E | 24 | 83 | 2.9 | 9 |
| Reference Alpha-Amylase with the substitutions N105D + K184A + S242Q | 60 | 183 | 7 | 19 |
| Reference Alpha-Amylase with the substitutions N105D + K184A + S242Q + A235W | 91 | | 10.8 | 30 |
| Reference Alpha-Amylase with the substitutions N105D + K184A + S242Q + G282W | 91 | | 11 | 30 |
| Reference Alpha-Amylase with the substitutions N105D + K184A + P245A | 64 | | 5.2 | 16 |
| Reference Alpha-Amylase with the substitutions N105D + K184A + P245K | 46 | | 5.5 | 16 |
| Reference Alpha-Amylase with the substitutions N105D + K184A + S301K + G303R + A304D | 38 | 110 | 4.7 | 15 |
| Reference Alpha-Amylase with the substitutions N105D + K184A + P348T | 46 | | 5.5 | 16 |
| Reference Alpha-Amylase with the substitutions N105D + K184A + P386E | 47 | | 5.2 | 18 |
| Reference Alpha-Amylase with the substitutions N105D + K184A + P386Q | 46 | | 5.4 | 18 |
| Reference Alpha-Amylase with the substitutions N105D + K184A + P386T | 49 | | 5.5 | 17 |
| Reference Alpha-Amylase with the substitutions N105D + K184A + P386V | 44 | | 3.9 | 16 |
| Reference Alpha-Amylase with the substitutions N105D + K184A + L388I | 52 | | 5.7 | 17 |
| Reference Alpha-Amylase with the substitutions N105D + K184A + L388V | 64 | | 5.2 | 16 |
| Reference Alpha-Amylase with the substitutions N105D + K184A + N407D + N430D + D432P | 45 | | 5.6 | 17 |
| Reference Alpha-Amylase with the substitutions N105D + K184A + D432P | 52 | | 5.5 | 17 |
| Reference Alpha-Amylase with the substitutions N105D + K184A + T459P | 47 | | 5.2 | 18 |
| Reference Alpha-Amylase with the substitutions N105D + Y206K | 8 | 27 | | 4 |
| Reference Alpha-Amylase with the substitutions N105D + Y206M | 18 | 81 | 2.2 | 11 |
| Reference Alpha-Amylase with the substitutions N105D + K220P + N224L | 37 | | 4.1 | 11 |
| Reference Alpha-Amylase with the substitutions N105D + S301K + G303R + A304D | 23 | 116 | 2.9 | 10 |

TABLE 1-continued

| Mutations (SEQ ID NO: 27 numbering) | T½ (min) (pH 4.5, 75° C., 0.12 mM CaCl$_2$) | T½ (min) (pH 5.5, 75° C., 0.12 mM CaCl$_2$) | T½ (min) (pH 4.5, 85° C., 0.12 mM CaCl$_2$) | T½ (min) (pH 5.5, 85° C., 0.12 mM CaCl$_2$) |
|---|---|---|---|---|
| Reference Alpha-Amylase with the substitutions V115W + F134Y + E135Q + K169S + G170R + R172L + G174R + F176Y | 23 | | 2 | 6 |
| Reference Alpha-Amylase with the substitution K117D | 17 | 37 | 2 | 5 |
| Reference Alpha-Amylase with the substitutions E129V + Q150T | 9 | 21 | | |
| Reference Alpha-Amylase with the substitutions F134Y + E135Q + K169S + G170R + R172L + G174R + F176Y | 21 | 78 | 2.2 | 7 |
| Reference Alpha-Amylase with the substitution Q150T | 32 | 90 | 4 | 10 |
| Reference Alpha-Amylase with the substitution T164V | 21 | 49 | 3 | 7 |
| Reference Alpha-Amylase with the substitution K184A | 30 | 52 | 3.7 | <15 |
| Reference Alpha-Amylase with the substitutions K184A + I204L | | | | |
| Reference Alpha-Amylase with the substitutions K184A + I270L | 8 | | | |
| Reference Alpha-Amylase with the substitution Y206M | 23 | 74 | 3 | 9 |
| Reference Alpha-Amylase with the substitution S242E | 8 | 18 | | 3 |
| Reference Alpha-Amylase with the substitutions S301K + G303R + A304D | 8 | 18 | | 3 |
| Reference Alpha-Amylase with the substitution G475K | 8 | 20 | | 3 |
| Reference Alpha-Amylase with the substitution G475Q | | 15 | | |

The results demonstrate that the alpha-amylase variants have a significantly greater half-life and stability than the reference alpha-amylase.

Example 5

Production of Ethanol Using Alpha-Amylase Variants

Three small scale mashes of a *Bacillus stearothermophilus* alpha-amylase variant sold by Novozymes under the name LIQUOZYME SC® and two alpha-amylase variants described in Example 4 were prepared as follows: about 54 g corn ground, about 51 g tap water, and about 45 g backset were mixed in a 250 mL plastic bottle to a total slurry weight of 150 g. The pH of the corn slurry was adjusted to 4.5. The enzymes were added to the mashes at 2 micrograms of amylase per gram of dry solids. For liquefaction, the alpha-amylases were added to the bottles and the bottles were mixed thoroughly and placed into a preheated 85° C. water bath. The samples were held in the water bath for 2 hours at pH 4.5 while being shaken every 10 minutes for the first 30 minutes and every 30 minutes thereafter for the remainder of the 2 hour liquefaction. The samples were then cooled in an ice bath; pH was adjusted to 5.0, and 0.75 mL urea and 0.45 mL penicillin were added to reach final concentrations of 1000 and 3 ppm in the mashes, respectively. The samples were then subjected to simultaneous saccharification and fermentation (SSF) with Spirizyme Fuel® (a glucoamylase product sold by Novozymes).

Five gram aliquots of the mashes were transferred into pre-weighed conical centrifuge tubes, using 5 replicates per mash. SSF was then performed on these mashes in a 32° C. water bath for 54 hours using Spirizyme Fuel®. The glucoamylase dose was 0.50 AGU/g DS for all fermentations. The $CO_2$ weight loss during SSF was measured and ethanol was quantified using HPLC after 54 hours of SSF. The average 54 hour HPLC SSF data are provided in Table 2 below.

TABLE 2

Ethanol Yields After 54 Hours Fermentation

| Alpha-Amylase | Ethanol, g/L | Std dev. |
|---|---|---|
| LIQUOZYME SC ® | 105.5946 | 0.3708 |
| Reference Alpha-Amylase disclosed in Example 4 with the substitution N105D | 115.6339 | 0.5562 |
| Reference Alpha-Amylase disclosed in Example 4 with the substitution K184A | 116.7224 | 0.8226 |

The results demonstrate that the use of the alpha-amylase variants resulted in a significantly greater yield of ethanol relative to LIQUOZYME SC®.

Example 6

Wash Performance in a Detergent

In order to assess the wash performance of alpha-amylases in a detergent, washing experiments were performed. The performance of hybrids 1, 2 and 3 of Example 1 was tested using the Mini Wash Assay and compared to the alpha-amylase having the amino acid sequence of SEQ ID NO: 7 with the deletions D183*+T184* (SEQ ID NO: 7 numbering). In this test, the wash performance of enzyme-detergent solutions can be examined at several enzyme dosages simultaneously.

Description of the Mini Wash Assay

The Mini Wash has a number of beakers with each beaker able to hold up to 80 ml enzyme-detergent solution. Water hardness is adjusted to 10° dH by addition of $CaCl_2$, $MgCl_2$, and $NaHCO_3$ to the test system. A textile sample, in this case CS-28, is attached to a frame designed to dip the textile into the enzyme-detergent solution with a frequency of 40 submersions per min. The temperature of the enzyme-detergent solution is controlled during wash. After wash the textile is rinsed in running tap water and subsequently dried in the dark. The wash performance of the enzyme-detergent solution is evaluated by measuring the remission at 460 nm with a ZEISS MCS 521 VIS Spectrophotometer.

Textiles:

CS-28 is a technical rice starch stained cotton textile that can be obtained from Center For Test materials BV, P.O. Box 120, 3133 KT Vlaardingen, the Netherlands.

The experiment was conducted under the experimental conditions specified below:

| | |
|---|---|
| Detergent | Commercial Tide 2X Ultra, inactivated by boiling for 15 minutes |
| Detergent dosage | 0.78 g/L |
| Test solution volume | 60 mL |
| pH | After wash pH was measured to 8.3 |
| Wash time | 20 minutes followed by 5 minutes rinse |
| Temperature | 40° C. |
| Water hardness | 10°dH, Ca/Mg 3:1 |
| Enzyme concentration in test solution | 0; 0.03; 0.06; 0.12; 0.20; 1.0 mg purified enzyme protein/L |
| Enzymes | SEQ ID NO: 7 with the deletions D183* + T184* Hybrid 1 Hybrid 2 Hybrid 3 |
| Test material | CS-28 (Rice starch on cotton) |

Results and Discussion:

The wash performance of the alpha-amylases was normalized to the wash performance of the alpha-amylase having the amino acid sequence of SEQ ID NO: 7 with the deletions D183*+T184*.

| Dose (mg enzyme protein/L) | SEQ ID NO: 7 with the deletions D183* + T184* | Hybrid 1 | Hybrid 2 | Hybrid 3 |
|---|---|---|---|---|
| 0 | 100.0 | 100.0 | 100.0 | 100.0 |
| 0.03 | 100.0 | 108.8 | 105.6 | 93.7 |
| 0.06 | 100.0 | 109.4 | 103.4 | 92.9 |
| 0.12 | 100.0 | 108.7 | 104.5 | 90.4 |
| 0.2 | 100.0 | 106.2 | 99.6 | 94.4 |
| 1 | 100.0 | 101.2 | 99.2 | 96.7 |

Example 7

Preparation of Hybrids

The following hybrids were prepared.

Hybrid 6: the amino acid residues 106-213 in a variant of SEQ ID NO: 5 having the substitutions M9L+R118K+G149A+G182T+G186A+D183*+G184*+N195F+M202L+V214V+T257I+Y295F+N299Y+R320K+M323T+A339S+E345R+R458K (using SEQ ID NO: 5 numbering) were removed and replaced with the amino acid residues 103-209 of SEQ ID NO: 13, and the following alterations were introduced: E182*, N183*, E188W, N189E and D192T, which correspond to E181*, N182*, E187W, N188E and D191T using SEQ ID NO: 27 numbering. The sequence of this hybrid is shown in SEQ ID NO: 32.

Hybrid 7: the amino acid residues 106-213 in a variant of SEQ ID NO: 8 (using SEQ ID NO: 8 numbering) were removed and replaced with the amino acid residues 103-209 of SEQ ID NO: 13. The sequence of this hybrid is shown in SEQ ID NO: 33.

Hybrid 8: the amino acid residues 104-208 in a variant of SEQ ID NO: 3 having amino acids 1-35 replaced by amino acids 1-33 of SEQ ID NO: 1 and having the substitutions G48A+T49I+G107A+H156Y+A181T+N190F+I201F+A209V+Q264S (using SEQ ID NO: 3 numbering) were removed and replaced with the amino acid residues 103-209 of SEQ ID NO: 13, and the following alterations were introduced: N102D, Q147T, E178*, N179*, K181A, E184W, N185E and D188T, which correspond to N105D, Q150T, E181*, N182*, K184A, E187W, N188E and D191T using SEQ ID NO: 27 numbering. The sequence of this hybrid is shown in SEQ ID NO: 34.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention is further defined in the following paragraphs:

Paragraph 1. An isolated alpha-amylase comprising an amino acid sequence having at least 80% sequence identity to the B-domain of a parent calcium-insensitive alpha-amylase, further having a higher ratio of activity measured by the Phadebas assay to the activity measured by the G7-pNG assay of more than 0.1, preferably of more than 0.2, even more preferred more than 0.5, and most preferred more than 1.

Paragraph 2. The alpha-amylase of paragraph 1, with at least 80% sequence identity to the sequence of amino acids 105-210 of SEQ ID NO: 13.

Paragraph 3. An isolated alpha-amylase comprising the A- and C-domains of a calcium-sensitive alpha-amylase and the B-domain of a calcium-insensitive alpha-amylase.

Paragraph 4. The alpha-amylase of any of the preceding paragraphs, further comprising one or more substitutions, insertions or deletions.

Paragraph 5. The alpha-amylase of paragraph 3, wherein the calcium-sensitive alpha-amylase is SEQ ID NO: 7 and the calcium-insensitive alpha-amylase is SEQ ID NO: 13, and the alpha-amylase optionally further comprises one or more of the following alterations: D183*+G184*, E189W, N190E, D193T, E189W+N190E+D193T, L217E, Y208M, R119D and W189E+L217E.

Paragraph 6. The alpha-amylase of paragraph 3, wherein the calcium-sensitive alpha-amylase is SEQ ID NO: 4 and the calcium-insensitive alpha-amylase is SEQ ID NO: 13, and the alpha-amylase optionally further comprises one or more of the following alterations: D181*+G182*, E187W, E187W+ N188E+D191T, N188E, D191T, S299K, S299K+G301R+ A302D+D405N+D428N+P430D, G301R, A302D, D405N+ D428N, and P430D.

Paragraph 7. An isolated alpha-amylase, comprising an A-domain with at least 60% sequence identity with the A-domain of any of SEQ ID NOS: 1-12, 29, and 30, a B-domain with at least 60% sequence identity with the B-domain of any of SEQ ID NOS: 13-16 and 31, and a C-domain with at least 60% sequence identity with the C-domain of any of SEQ ID NOS: 1-12, 29, and 30.

Paragraph 8. The alpha-amylase of paragraph 7, wherein the A-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the A-domain of SEQ ID NO: 1.

Paragraph 9. The alpha-amylase of paragraph 7, wherein the A-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the A-domain of SEQ ID NO: 2.

Paragraph 10. The alpha-amylase of paragraph 7, wherein the A-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the A-domain of SEQ ID NO: 3.

Paragraph 11. The alpha-amylase of paragraph 7, wherein the A-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the A-domain of SEQ ID NO: 4.

Paragraph 12. The alpha-amylase of paragraph 7, wherein the A-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the A-domain of SEQ ID NO: 5.

Paragraph 13. The alpha-amylase of paragraph 7, wherein the A-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the A-domain of SEQ ID NO: 6.

Paragraph 14. The alpha-amylase of paragraph 7, wherein the A-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the A-domain of SEQ ID NO: 7.

Paragraph 15. The alpha-amylase of paragraph 7, wherein the A-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the A-domain of SEQ ID NO: 8.

Paragraph 16. The alpha-amylase of paragraph 7, wherein the A-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the A-domain of SEQ ID NO: 9.

Paragraph 17. The alpha-amylase of paragraph 7, wherein the A-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the A-domain of SEQ ID NO: 10.

Paragraph 18. The alpha-amylase of paragraph 7, wherein the A-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the A-domain of SEQ ID NO: 11.

Paragraph 19. The alpha-amylase of paragraph 7, wherein the A-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the A-domain of SEQ ID NO: 12.

Paragraph 20. The alpha-amylase of paragraph 7, wherein the A-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the A-domain of SEQ ID NO: 29.

Paragraph 21. The alpha-amylase of paragraph 7, wherein the A-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the A-domain of SEQ ID NO: 30.

Paragraph 22. The alpha-amylase of any of paragraphs 7-21, wherein the A1-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the sequence starting at a position in the range of positions 1-5 and ending a position in the range of positions 91-111, e.g., starting at a position in the range of positions 1-3 and ending at a position in the range of positions 96-101 or starting at a position in the range of positions 1-3 and ending at a position in the range of positions 101-106, in particular positions 1-101 of SEQ ID NO: 1.

Paragraph 23. The alpha-amylase of any of paragraphs 7-21, wherein the A1-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the sequence starting at a position in the range of positions 1-5 and ending a position in the range of positions 95-115, e.g., starting at a position in the range of positions 1-3 and ending at a position in the range of positions 100-105 or starting at a position in the range of positions 1-3 and ending at a position in the range of positions 105-110, in particular positions 1-105 of SEQ ID NO: 2.

Paragraph 24. The alpha-amylase of any of paragraphs 7-21, wherein the A1-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the sequence starting at a position in the range of positions 1-5 and ending a position in the range of positions 93-113, e.g., starting at a position in the range of positions 1-3 and ending at a position in the range of positions 98-103 or starting at a position in the range of positions 1-3 and ending at a position in the range of positions 103-108, in particular positions 1-103 of SEQ ID NO: 3.

Paragraph 25. The alpha-amylase of any of paragraphs 7-21, wherein the A1-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the sequence starting at a position in the range of positions 1-5 and ending a position in the range of positions 94-114, e.g., starting at a position in the range of positions 1-3 and ending at a position in the range of positions 99-104 or starting at a position in the range of positions 1-3 and ending at a position in the range of positions 104-109, in particular positions 1-104 of SEQ ID NO: 4.

Paragraph 26. The alpha-amylase of any of paragraphs 7-21, wherein the A1-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the sequence starting at a position in the range of positions 1-5 and ending a position in the range of positions 95-115, e.g., starting at a position in the range of positions 1-3 and ending at a position in the range of positions 100-105 or starting at a position in the range of positions 1-3 and ending at a position in the range of positions 105-110, in particular positions 1-105 of SEQ ID NO: 5.

Paragraph 27. The alpha-amylase of any of paragraphs 7-21, wherein the A1-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the sequence starting at a position in the range of positions 1-5 and ending a position in the range of positions 95-115, e.g., starting at a position in the range of positions 1-3 and ending at a position in the range of positions 100-105 or starting at a position in the range of positions 1-3 and ending at a position in the range of positions 105-110, in particular positions 1-105 of SEQ ID NO: 6.

Paragraph 28. The alpha-amylase of any of paragraphs 7-21, wherein the A1-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the sequence starting at a position in the range of positions 1-5 and ending a position in the range of positions 95-115, e.g., starting at a position in the range of positions 1-3 and ending at a position in the range of positions 100-105 or starting at a position in the range of positions 1-3 and ending at a position in the range of positions 105-110, in particular positions 1-105 of SEQ ID NO: 7.

Paragraph 29. The alpha-amylase of any of paragraphs 7-21, wherein the A1-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the sequence starting at a position in the range of positions 1-5 and ending a position in the range of positions 95-115, e.g., starting at a position in the range of positions 1-3 and ending at a position in the range of positions 100-105 or starting at a position in the range of positions 1-3 and ending at a position in the range of positions 105-110, in particular positions 1-105 of SEQ ID NO: 8.

Paragraph 30. The alpha-amylase of any of paragraphs 7-21, wherein the A1-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the sequence starting at a position in the range of positions 1-5 and ending a position in the range of positions 95-115, e.g., starting at a position in the range of positions 1-3 and ending at a position in the range of positions 100-105 or starting at a position in the range of positions 1-3 and ending at a position in the range of positions 105-110, in particular positions 1-105 of SEQ ID NO: 9.

Paragraph 31. The alpha-amylase of any of paragraphs 7-21, wherein the A1-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the sequence starting at a position in the range of positions 1-5 and ending a position in the range of positions 95-115, e.g., starting at a position in the range of positions 1-3 and ending at a position in the range of positions 100-105 or starting at a position in the range of positions 1-3 and ending at a position in the range of positions 105-110, in particular positions 1-105 of SEQ ID NO: 10.

Paragraph 32. The alpha-amylase of any of paragraphs 7-21, wherein the A1-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the sequence starting at a position in the range of positions 1-5 and ending a position in the range of positions 95-115, e.g., starting at a position in the range of positions 1-3 and ending at a position in the range of positions 100-105 or starting at a position in the range of positions 1-3 and ending at a position in the range of positions 105-110, in particular positions 1-105 of SEQ ID NO: 11.

Paragraph 33. The alpha-amylase of any of paragraphs 7-21, wherein the A1-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the sequence starting at a position in the range of positions 1-5 and ending a position in the range of positions 95-115, e.g., starting at a position in the range of positions 1-3 and ending at a position in the range of positions 100-105 or starting at a position in the range of positions 1-3 and ending at a position in the range of positions 105-110, in particular positions 1-105 of SEQ ID NO: 12.

Paragraph 34. The alpha-amylase of any of paragraphs 7-21, wherein the A1-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the sequence starting at a position in the range of positions 1-5 and ending a position in the range of positions 94-114, e.g., starting at a position in the range of positions 1-3 and ending at a position in the range of positions 99-104 or starting at a position in the range of positions 1-3 and ending at a position in the range of positions 104-109, in particular positions 1-104 of SEQ ID NO: 29.

Paragraph 35. The alpha-amylase of any of paragraphs 7-21, wherein the A1-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the sequence starting at a position in the range of positions 1-5 and ending a position in the range of positions 92-112, e.g., starting at a position in the range of positions 1-3 and ending at a position in the range of positions 97-102 or starting at a position in the range of positions 1-3 and ending at a position in the range of positions 102-107, in particular positions 1-102 of SEQ ID NO: 30.

Paragraph 36. The alpha-amylase of any of paragraphs 7-35, wherein the B-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the sequence starting at a position in the range of positions 93-113 and ending at a position in the range of positions 195-215, e.g., starting at a position in the range of positions 97-109 and ending at a position in the range of positions 199-211 or starting at a position in the range of positions 100-106 and ending at a position in the range of positions 202-208, in particular positions 103-208 of SEQ ID NO: 13.

Paragraph 37. The alpha-amylase of any of paragraphs 7-35, wherein the B-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the sequence starting at a position in the range of positions 93-113 and ending at a position in the range of positions 195-215, e.g., starting at a position in the range of positions 97-109 and ending at a position in the range of positions 199-211 or starting at a position in the range of positions 100-106 and ending at a position in the range of positions 202-208, in particular positions 104-207 of SEQ ID NO: 14.

Paragraph 38. The alpha-amylase of any of paragraphs 7-35, wherein the B-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the sequence starting at a position in the range of positions 93-113 and ending at a position in the range of positions 195-215, e.g., starting at a position in the range of positions 97-109 and ending at a position in the range of positions 199-211 or starting at a position in the range of positions 100-106 and ending at a position in the range of positions 202-208, in particular positions 104-207 of SEQ ID NO: 15.

Paragraph 39. The alpha-amylase of any of paragraphs 7-35, wherein the B-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the sequence starting at a position in the range of positions 100-120 and ending at a position in the range of positions 161-181, e.g., starting at a position in the range of positions 105-115 and ending at a position in the range of positions 166-171 or starting at a position in the range of positions 107-113 and ending at a position in the range of positions 171-176, in particular positions 110-171 of SEQ ID NO: 16.

Paragraph 40. The alpha-amylase of any of paragraphs 7-35, wherein the B-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the sequence starting at a position in the range of positions 100-120 and ending at a position in the range of positions 161-181, e.g., starting at a position in the range of positions 105-115 and ending at a position in the range of positions 166-171 or starting at a position in the range of positions 107-113 and ending at a position in the range of positions 171-176, in particular positions 110-171 of SEQ ID NO: 31.

Paragraph 41. The alpha-amylase of any of paragraphs 7-40, wherein the C-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the C-domain of SEQ ID NO: 1.

Paragraph 42. The alpha-amylase of any of paragraphs 7-40, wherein the C-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the C-domain of SEQ ID NO: 2.

Paragraph 43. The alpha-amylase of any of paragraphs 7-40, wherein the C-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the C-domain of SEQ ID NO: 3.

Paragraph 44. The alpha-amylase of any of paragraphs 7-40, wherein the C-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the C-domain of SEQ ID NO: 4.

Paragraph 45. The alpha-amylase of any of paragraphs 7-40, wherein the C-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the C-domain of SEQ ID NO: 5.

Paragraph 46. The alpha-amylase of any of paragraphs 7-40, wherein the C-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the C-domain of SEQ ID NO: 6.

Paragraph 47. The alpha-amylase of any of paragraphs 7-40, wherein the C-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the C-domain of SEQ ID NO: 7.

Paragraph 48. The alpha-amylase of any of paragraphs 7-40, wherein the C-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the C-domain of SEQ ID NO: 8.

Paragraph 49. The alpha-amylase of any of paragraphs 7-40, wherein the C-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the C-domain of SEQ ID NO: 9.

Paragraph 50. The alpha-amylase of any of paragraphs 7-40, wherein the C-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the C-domain of SEQ ID NO: 10.

Paragraph 51. The alpha-amylase of any of paragraphs 7-40, wherein the C-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the C-domain of SEQ ID NO: 11.

Paragraph 52. The alpha-amylase of any of paragraphs 7-40, wherein the C-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the C-domain of SEQ ID NO: 12.

Paragraph 53. The alpha-amylase of any of paragraphs 7-40, wherein the C-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the C-domain of SEQ ID NO: 29.

Paragraph 54. The alpha-amylase of any of paragraphs 7-40, wherein the C-domain has at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the C-domain of SEQ ID NO: 30.

Paragraph 55. The alpha-amylase of any of paragraphs 7-54, wherein the A2 and C-domains have at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the sequence starting at a position in the range of positions 198-218 and ending at a position in the range of positions 478-483, e.g., starting at a position in the range of positions 203-208 and ending at a position in the range of positions 480-483 or starting at a position in the range of positions 208-213 and ending at a position in the range of positions 480-483, in particular positions 208-483 of SEQ ID NO: 1.

Paragraph 56. The alpha-amylase of any of paragraphs 7-54, wherein the A2 and C-domains have at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the sequence starting at a position in the range of positions 202-222 and ending at a position in the range of positions 479-484, e.g., starting at a position in the range of positions 207-212 and ending at a position in the range of positions 481-484 or starting at a position in the range of positions 212-217 and ending at a position in the range of positions 481-484, in particular positions 212-484 of SEQ ID NO: 2.

Paragraph 57. The alpha-amylase of any of paragraphs 7-54, wherein the A2 and C-domains have at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the sequence starting at a position in the range of positions 198-218 and ending at a position in the range of positions 478-483, e.g., starting at a position in the range of positions 203-208 and ending at a position in the range of positions 480-483 or starting at a position in the range of positions 208-213 and ending at a position in the range of positions 480-483, in particular positions 208-483 of SEQ ID NO: 3.

Paragraph 58. The alpha-amylase of any of paragraphs 7-54, wherein the A2 and C-domains have at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the sequence starting at a position in the range of positions 201-221 and ending at a position in the range of positions 478-483, e.g., starting at a position in the range of positions 206-211 and ending at a position in the range of positions 480-483 or starting at a position in the range of positions 211-216 and ending at a position in the range of positions 480-483, in particular positions 211-483 of SEQ ID NO: 4.

Paragraph 59. The alpha-amylase of any of paragraphs 7-54, wherein the A2 and C-domains have at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the sequence starting at a position in the range of positions 193-223 and ending at a position in the range of positions 482-485, e.g., starting at a position in the range of positions 208-213 and ending at a position in the range of positions 482-485 or starting at a position in the range of positions 213-218 and ending at a position in the range of positions 482-485, in particular positions 213-485 of SEQ ID NO: 5.

Paragraph 60. The alpha-amylase of any of paragraphs 7-54, wherein the A2 and C-domains have at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the sequence starting at a position in the range of positions 203-223 and ending at a position in the range of positions 482-485, e.g., starting at a position in the range of positions 208-213 and ending at a position in the range of positions 482-485 or starting at a position in the range of positions 213-218 and ending at a position in the range of positions 482-485, in particular positions 213-485 of SEQ ID NO: 6.

Paragraph 61. The alpha-amylase of any of paragraphs 7-54, wherein the A2 and C-domains have at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the sequence starting at a position in the range of positions 203-223 and ending at a position in the range of positions 482-485, e.g., starting at a position in the range of positions 208-213 and ending at a position in the range of positions 482-485 or starting at a position in the range of positions 213-218 and ending at a position in the range of positions 482-485, in particular positions 213-485 of SEQ ID NO: 7.

Paragraph 62. The alpha-amylase of any of paragraphs 7-54, wherein the A2 and C-domains have at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the sequence starting at a position in the range of positions 203-223 and ending at a position in the range of positions 482-485, e.g., starting at a position in the range of positions 208-213 and ending at a position in the range of positions 482-485 or starting at a position in the range of positions 213-218 and ending at a position in the range of positions 482-485, in particular positions 213-485 of SEQ ID NO: 8.

Paragraph 63. The alpha-amylase of any of paragraphs 7-54, wherein the A2 and C-domains have at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the sequence starting at a position in the range of positions 203-223 and ending at a position in the range of positions 481-484, e.g., starting at a position in the range of positions 208-213 and ending at a position in the range of positions 482-484 or starting at a position in the range of positions 213-218 and ending at a position in the range of positions 482-484, in particular positions 213-484 of SEQ ID NO: 9.

Paragraph 64. The alpha-amylase of any of paragraphs 7-54, wherein the A2 and C-domains have at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the sequence starting at a position in the range of positions 203-223 and ending at a position in the range of positions 482-484, e.g., starting at a position in the range of positions 208-213 and ending at a position in the range of positions 482-484 or starting at a position in the range of positions 213-218 and ending at a position in the range of positions 482-484, in particular positions 213-484 of SEQ ID NO: 10.

Paragraph 65. The alpha-amylase of any of paragraphs 7-54, wherein the A2 and C-domains have at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the sequence starting at a position in the range of positions 203-223 and ending at a position in the range of positions 482-485, e.g., starting at a position in the range of positions 208-213 and ending at a position in the range of positions 482-485 or starting at a position in the range of positions 213-218 and ending at a position in the range of positions 482-485, in particular positions 213-485 of SEQ ID NO: 11.

Paragraph 66. The alpha-amylase of any of paragraphs 7-54, wherein the A2 and C-domains have at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the sequence starting at a position in the range of positions 203-223 and ending at a position in the range of positions 482-485, e.g., starting at a position in the range of positions 208-213 and ending at a position in the range of positions 482-485 or starting at a position in the range of positions 213-218 and ending at a position in the range of positions 482-485, in particular positions 213-485 of SEQ ID NO: 12.

Paragraph 67. The alpha-amylase of any of paragraphs 7-54, wherein the A2 and C-domains have at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the sequence starting at a position in the range of positions 201-221 and ending at a position in the range of positions 478-483, e.g., starting at a position in the range of positions 206-211 and ending at a position in the range of positions 480-483 or starting at a position in the range of positions 211-216 and ending at a position in the range of positions 480-483, in particular positions 211-483 of SEQ ID NO: 29.

Paragraph 68. The alpha-amylase of any of paragraphs 7-54, wherein the A2 and C-domains have at least 60% sequence identity, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity with the sequence starting at a position in the range of positions 199-219 and ending at a position in the range of positions 479-484, e.g., starting at a position in the range of positions 204-209 and ending at a position in the range of positions 481-484 or starting at a position in the range of positions 209-214 and ending at a position in the range of positions 481-484, in particular positions 209-484 of SEQ ID NO: 30.

Paragraph 69. The alpha-amylase of any of paragraphs 1-68, which is more thermostable than the alpha-amylase of any of SEQ ID NOS: 1-12, 29 and 30.

Paragraph 70. The alpha-amylase of any of paragraphs 1-69, which has reduced calcium sensitivity than the alpha-amylase of any of SEQ ID NOS: 1-12, 29 and 30.

Paragraph 71. A detergent composition comprising an alpha-amylase of any of paragraphs 1-70 and a surfactant.

Paragraph 72. A composition comprising an alpha-amylase of any of paragraphs 1-70 and one or more enzymes selected from the group consisting of beta-amylase, cellulase (beta-glucosidase, cellobiohydrolase, and endoglucanase) glucoamylase, hemicellulase (e.g., xylanase), isoamylase, isomerase, lipase, phytase, protease, and pullulanase.

Paragraph 73. Use of an alpha-amylase of any of paragraphs 1-70 for washing and/or dishwashing.

Paragraph 74. Use of an alpha-amylase of any of paragraphs 1-70 for desizing a textile.

Paragraph 75. Paragraph 89. Use of an alpha-amylase of any of paragraphs 1-70 for producing a baked product.

Paragraph 76. Use of an alpha-amylase of any of paragraphs 1-70 for liquefying a starch-containing material.

Paragraph 77. A method of producing liquefied starch, comprising liquefying a starch-containing material with an alpha-amylase of any of paragraphs 1-70.

Paragraph 78. A process of producing a fermentation product, comprising (a) liquefying a starch-containing material with an alpha-amylase of any of paragraphs 1-70 to produce a liquefied mash;

(b) saccharifying the liquefied mash to produce fermentable sugars; and (c) fermenting the fermentable sugars in the presence of a fermenting organism.

Paragraph 79. The process of paragraph 78, wherein the starch-containing material is liquefied with the alpha-amylase and a pullulanase, e.g., a GH57 pullulanase.

Paragraph 80. The process of paragraph 79, wherein the pullulanase is obtained from a strain of *Thermococcus*, including *Thermococcus* sp. AM4, *Thermococcus* sp. HJ21, *Thermococcus barophilus*, *Thermococcus gammatolerans*, *Thermococcus hydrothermalis*; *Thermococcus kodakarensis*, *Thermococcus litoralis*, and *Thermococcus onnurineus*; or from a strain of *Pyrococcus*, such as *Pyrococcus abyssi* and *Pyrococcus furiosus*.

Paragraph 81. The process of any of paragraphs 78-80, further comprising adding a protease, such as an acid fungal protease or a metalloprotease before, during and/or after liquefaction.

Paragraph 82. The process of paragraph 81, wherein the metalloprotease is obtained from a strain of *Thermoascus*, preferably a strain of *Thermoascus aurantiacus*, especially *Thermoascus aurantiacus* CGMCC No. 0670.

Paragraph 83. A process of producing a fermentation product, comprising contacting a starch substrate with an alpha-amylase of any of paragraphs 1-70, a glucoamylase, and a fermenting organism.

Paragraph 84. The process of any of paragraphs 78-83, wherein the fermentation product is selected from the group consisting of alcohol (e.g., ethanol and butanol), organic acids (e.g., succinic acid and lactic acid), sugar alcohols (e.g., glycerol), ascorbic acid intermediates (e.g., gluconate, 2-keto-D-gluconate, 2,5-diketo-D-gluconate, and 2-keto-L-gulonic acid), amino acids (e.g., lysine), proteins (e.g., antibodies and fragment thereof).

Paragraph 85. A nucleic acid sequence encoding an alpha-amylase of any of paragraphs 1-70.

Paragraph 86. A plasmid comprising the nucleic acid sequence of paragraph 85.

Paragraph 87. A host cell comprising the nucleic acid sequence of paragraph 85 or a plasmid of paragraph 86.

Paragraph 88. A transgenic plant, plant part or plant cell transformed with the nucleic acid sequence of paragraph 85.

Paragraph 89. A method for preparing an alpha-amylase of any of paragraphs 1-70, comprising the following steps:

(a) growing the host cell of paragraph 87 under conditions leading to expression of the hybrid alpha-amylase; and (b) recovering the hybrid alpha-amylase.

The invention claimed is:

1. An isolated alpha-amylase comprising A-, B- and C-domains, wherein the A-domain has at least 90% sequence identity to the sequence of amino acids 1-105 and 213-398 of SEQ ID NO: 7, the B-domain has at least 90% sequence identity to the sequence of amino acids 103-208 of SEQ ID NO: 13, and the C-domain has at least 90% sequence identity to the sequence of amino acids 399-485 of SEQ ID NO: 7.

2. The alpha-amylase of claim 1, wherein the A-domain has at least 95% sequence identity to the sequence of amino acids 1-105 and 213-398 of SEQ ID NO: 7.

3. The alpha-amylase of claim 1, wherein the B-domain has at least 95% sequence identity to the sequence of amino acids 103-208 of SEQ ID NO: 13.

4. The alpha-amylase of claim 2, wherein the B-domain has at least 95% sequence identity to the sequence of amino acids 103-208 of SEQ ID NO: 13.

5. The alpha-amylase of claim 1, wherein the C-domain has at least 95% sequence identity to the sequence of amino acids 399-485 of SEQ ID NO: 7.

6. The alpha-amylase of claim 2, wherein the C-domain has at least 95% sequence identity to the sequence of amino acids 399-485 of SEQ ID NO: 7.

7. The alpha-amylase of claim 3, wherein the C-domain has at least 95% sequence identity to the sequence of amino acids 399-485 of SEQ ID NO: 7.

8. The alpha-amylase of claim 4, wherein the C-domain has at least 95% sequence identity to the sequence of amino acids 399-485 of SEQ ID NO: 7.

9. The alpha-amylase of claim 4, which comprises the sequence of SEQ ID NO: 21.

10. A detergent composition comprising an alpha-amylase of claim 1 and a surfactant.

11. A composition comprising an alpha-amylase of claim 1 and one or more enzymes selected from the group consisting of beta-amylase, cellulase (beta-glucosidase, cellobiohydrolase, and endoglucanase) glucoamylase, hemicellulase (e.g., xylanase), isoamylase, isomerase, lipase, phytase, protease, and pullulanase.

12. A method of producing liquefied starch, comprising liquefying a starch-containing material with an alpha-amylase of claim 1.

13. A process of producing a fermentation product, comprising
  (a) liquefying a starch-containing material with an alpha-amylase of claim 1 to produce a liquefied mash;
  (b) saccharifying the liquefied mash to produce fermentable sugars; and
  (c) fermenting the fermentable sugars in the presence of a fermenting organism.

14. The process of claim 13, wherein the fermentation product is selected from the group consisting of alcohols, organic acids, sugar alcohols, ascorbic acid intermediates, amino acids, and proteins.

15. A process of producing a fermentation product, comprising contacting a starch substrate with an alpha-amylase of claim 1, a glucoamylase, and a fermenting organism.

16. The process of claim 15, wherein the fermentation product is selected from the group consisting of alcohols, organic acids, sugar alcohols, ascorbic acid intermediates, amino acids, and proteins.

* * * * *